US008197951B2

(12) United States Patent
Kim et al.

(10) Patent No.: US 8,197,951 B2
(45) Date of Patent: Jun. 12, 2012

(54) EMITTING MATERIAL AND ORGANIC LIGHT EMITTING DIODE USING THE SAME

(75) Inventors: Kong Kyeom Kim, Daejeon (KR); Hye Young Jang, Daejeon (KR); Sung Kil Hong, Daejeon (KR); Sung Jin Yeo, Daejeon (KR); So-Yeon Choi, legal representative, Daejeon (KR); Sang Young Jeon, Daejeon (KR)

(73) Assignee: LG Chem, Ltd., Seoul (KR)

(*) Notice: Subject to any disclaimer, the term of this patent is extended or adjusted under 35 U.S.C. 154(b) by 827 days.

(21) Appl. No.: 11/600,819

(22) Filed: Nov. 17, 2006

(65) Prior Publication Data

US 2007/0202355 A1 Aug. 30, 2007

(30) Foreign Application Priority Data

Nov. 18, 2005 (KR) ........................ 10-2005-0111004
May 17, 2006 (KR) ........................ 10-2006-0044097

(51) Int. Cl.
*H01L 51/54* (2006.01)
*C09K 11/06* (2006.01)

(52) U.S. Cl. ............ 428/690; 585/26; 548/440; 549/29; 564/433; 564/434; 428/917; 313/504; 313/506

(58) Field of Classification Search .................. 428/690, 428/917, 411.1, 336; 313/502–509; 257/40, 257/88, 104, E51; 532/1; 548/440; 549/29; 564/433, 434

See application file for complete search history.

(56) References Cited

U.S. PATENT DOCUMENTS

| | | | | |
|---|---|---|---|---|
| 6,203,933 | B1 | 3/2001 | Nakaya et al. | |
| 6,251,531 | B1 * | 6/2001 | Enokida et al. | 428/690 |
| 7,164,155 | B2 * | 1/2007 | Yamazaki et al. | 257/84 |
| 2002/0048687 | A1 * | 4/2002 | Hosokawa et al. | 428/690 |
| 2003/0118866 | A1 | 6/2003 | Oh et al. | |
| 2004/0016907 | A1 * | 1/2004 | Shi | 252/301.16 |
| 2004/0161633 | A1 * | 8/2004 | Seo et al. | 428/690 |
| 2005/0089715 | A1 | 4/2005 | Cosimbescu et al. | |
| 2005/0099115 | A1 | 5/2005 | Saitoh et al. | |

FOREIGN PATENT DOCUMENTS

| | | | |
|---|---|---|---|
| EP | 0786926 | A2 | 7/1997 |
| EP | 1 009 044 | | 6/2000 |
| EP | 1317005 | | 6/2003 |
| EP | 1 440 959 | | 7/2004 |
| EP | 1 491 609 | | 12/2004 |
| JP | 07-138561 | | 5/1995 |
| JP | 08-333569 | | 12/1996 |
| JP | 2000-273056 | | 10/2000 |
| JP | 2001-110571 | A | 4/2001 |
| JP | 2001-131541 | | 5/2001 |
| JP | 2001-288377 | | 10/2001 |

(Continued)

*Primary Examiner* — Jennifer Chriss
*Assistant Examiner* — J. L. Yang
(74) *Attorney, Agent, or Firm* — McKenna Long & Aldridge LLP

(57) ABSTRACT

The present invention provides novel structure of light emitting material and an organic light emitting diode using the same. The light emitting material can serve as a light emitting material alone, and can also serve as a light emitting host in combination with a proper light emitting dopant, or a light emitting dopant in combination with a proper light emitting host, particularly in an organic emitting diode.

4 Claims, 1 Drawing Sheet

FOREIGN PATENT DOCUMENTS

| | | | |
|---|---|---|---|
| JP | 2002-012861 | | 1/2002 |
| JP | 2002-134276 | A | 5/2002 |
| JP | 2005-008559 | | 1/2005 |
| JP | 2005-015420 | | 1/2005 |
| KR | 10-2002-0070333 | | 9/2002 |
| KR | 10-2003-0014927 | | 2/2003 |
| KR | 10-2005-0000520 | | 1/2005 |
| WO | WO 01/72673 | | 10/2001 |
| WO | WO 03/012890 | | 2/2003 |
| WO | WO 03/095445 | | 11/2003 |

* cited by examiner

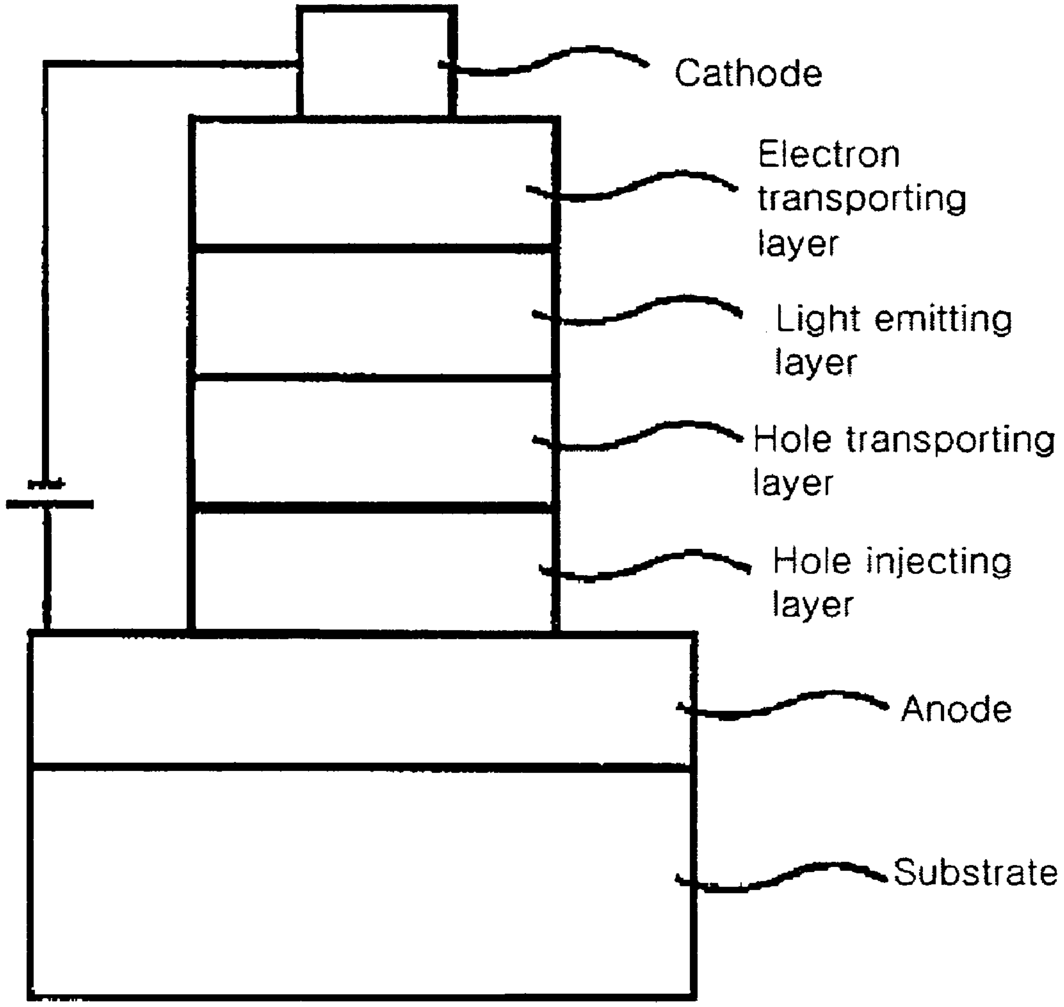
Cathode
Electron transporting layer
Light emitting layer
Hole transporting layer
Hole injecting layer
Anode
Substrate

EMITTING MATERIAL AND ORGANIC LIGHT EMITTING DIODE USING THE SAME

TECHNICAL FIELD

The present invention relates to a novel structure of a light emitting material and an organic light emitting device using the same.

This application claims priority benefits from Korean Patent Application No. 10-2005-111004, filed on Nov. 18, 2005 and Korean Patent Application No. 10-2006-0044097, filed on May 17, 2006, the entire contents of which are fully incorporated herein by reference.

BACKGROUND ART

In general, the term "organic light emitting phenomenon" refers to a phenomenon in which electric energy is converted to light energy by means of an organic material. The organic light emitting diode using the organic light emitting phenomenon has a structure usually comprising an anode, a cathode and an organic material layer interposed there between. Herein, the organic material layer may be mostly formed in a multilayer structure comprising layers of different materials, for example, the hole injecting layer, the hole transporting layer, the light emitting layer, the electron transporting layer, the electron injecting layer and the like, in order to improve efficiency and stability of the organic light emitting diode. In the organic light emitting diode having such a structure, when a voltage is applied between two electrodes, holes from the anode and electrons from a cathode are injected into the organic material layer, the holes and the electrons injected are combined together to form excitons. Further, when the excitons drop to a ground state, lights are emitted. Such the organic light emitting diode is known to have characteristics such as self-luminescence, high brightness, high efficiency, low drive voltage, wide viewing angle, high contrast and high-speed response.

The materials used for the organic material layer of the organic light emitting diode can be classified into a light emitting material and a charge-transporting material, for example, a hole injecting material, a hole transporting material, an electron transporting material and an electron injecting material, according to their functions. Further, the light emitting material can be divided into a high molecular weight type light emitting material or a low molecular weight type light emitting material according to the molecular weights, which ranges from a fluorescent material derived from the electron in the singlet excitation state to a phosphorescent material derived from the in electron in the triplet excitation state according to the light emitting mechanism. Further, the light emitting material can be divided into a blue, green or red light emitting material and a yellow or orange light emitting material required for giving more natural color, according to a light emitting color.

On the other hand, an efficiency of a device is lowered owing to maximum luminescence wavelength moved to a longer wavelength due to the interaction between the molecules, the deterioration of color purity and the reduction in light emitting efficiency when only one material is used for the light emitting material, and therefore a host/dopant system can be used as the light emitting material for the purpose of enhancing the color purity and the light emitting efficiency through energy transfer. It is based on the principle that if a small amount of a dopant having a smaller energy band gap than a host which forms a light emitting layer, excitons which are generated in the light emitting layer are transported to the dopant, thus emitting a light having a high efficiency. Here, since the wavelength of the host is moved according to the wavelength of the dopant, a light having a desired wavelength can be obtained according the kind of the dopant.

In order to allow the organic light emitting diode to fully exhibit the above-mentioned excellent characteristics, a material constituting the organic material layer in the device, for example, a hole injecting material, a hole transporting material, a light emitting material, an electron transporting material and an electron injecting material should be essentially composed of a stable and efficient material. However, the development of a stable and efficient organic material layer material for the organic light emitting diode has not yet been fully realized. Accordingly, the development of new materials is continuously desired.

DISCLOSURE

Technical Problem

The present inventors have discovered a novel structure of a light emitting material, and have found out that this light emitting material can serve as materials for an organic material layer, and in particular as a light emitting material, in an organic light emitting diode.

Technical Solution

Therefore, it is an object of the present invention to provide a novel structure of a light emitting material and an organic light emitting diode using the same.

Advantageous Effects

The compound of the present invention is a novel structure of a light emitting material, which can not only serve as a light emitting material alone, but also serve as a light emitting host in combination with a proper light emitting dopant, or a light emitting dopant in combination with a proper light emitting host, particularly in an organic light emitting diode.

DESCRIPTION OF DRAWINGS

FIG. 1 is a diagram illustrating a structure of an organic light emitting diode according to one embodiment of the present invention.

BEST MODE

The present invention provides a compound represented by the following formula 1:

[Formula 1]

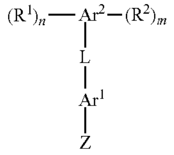

wherein $Ar^1$ is a $C_5$-$C_{20}$ arylene group which is unsubstituted or substituted with at least one group selected from the group consisting of a $C_1$-$C_{20}$ alkyl group, a $C_2$-$C_{20}$ alkenyl group, a $C_2$-$C_{20}$ alkynyl group, a $C_3$-$C_{20}$ cycloalkyl group, a $C_3$-$C_{20}$ heterocycloalkyl group, a $C_6$-$C_{20}$ aryl group, a $C_5$-$C_{20}$ heteroaryl group and an arylamine group, $Ar^2$ is a $C_6$-$C_{20}$ aryl group, which contains hydrogen atoms at the positions other than the positions bonded with —$(R^1)_n$, —$(R^2)_m$ and L, L is a direct bond; a $C_5$-$C_{20}$ arylene group which is unsubstituted or substituted with at least one group selected from the group consisting of a $C_1$-$C_{20}$ alkyl group, a $C_2$-$C_{20}$ alkenyl group, a $C_2$-$C_{20}$ alkynyl group, a $C_3$-$C_{20}$ cycloalkyl group, a $C_3$-$C_{20}$ heterocycloalkyl group, a $C_6$-$C_{20}$ aryl group and a $C_5$-$C_{20}$ heteroaryl group; or a $C_5$-$C_{20}$ heteroarylene group which is unsubstituted or substituted with at least one group selected from the group consisting of a $C_1$-$C_{20}$ alkyl group, a $C_2$-$C_{20}$ alkenyl group, a $C_2$-$C_{20}$ alkynyl group, a $C_3$-$C_{20}$ cycloalkyl group, a $C_3$-$C_{20}$ heterocycloalkyl group, a $C_6$-$C_{20}$ aryl group and a $C_5$-$C_{20}$ heteroaryl group, $R^1$ and $R^2$ are each independently

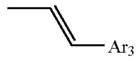

or

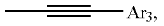

and in the case where $Ar^2$ is a $C_6$ aryl group, are not present at a para position relative to L, wherein $Ar^3$ is a $C_6$-$C_{20}$ aryl group which is unsubstituted or substituted with at least one group selected from the group consisting of a $C_1$-$C_{20}$ alkyl group, a $C_2$-$C_{20}$ alkenyl group, a $C_2$-$C_{20}$ alkynyl group, a $C_3$-$C_{20}$ cycloalkyl group, a $C_3$-$C_{20}$ heterocycloalkyl group, a $C_6$-$C_{20}$ aryl group, a $C_5$-$C_{20}$ heteroaryl group and an arylamine group; or a $C_5$-$C_{20}$ heteroaryl group which is unsubstituted or substituted with at least one group selected from the group consisting of a $C_1$-$C_{20}$ alkyl group, a $C_2$-$C_{20}$ alkenyl group, a $C_2$-$C_{20}$ alkynyl group, a $C_3$-$C_{20}$ cycloalkyl group, a $C_3$-$C_{20}$ heterocycloalkyl group, a $C_6$-$C_{20}$ aryl group and a $C_5$-$C_{20}$ heteroaryl group, Z is a hydrogen atom,

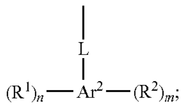

a $C_1$-$C_{20}$ alkyl group which is unsubstituted or substituted with at least one group selected from the group consisting of a $C_1$-$C_{20}$ alkyl group, a $C_2$-$C_{20}$ alkenyl group, a $C_2$-$C_{20}$ alkynyl group, a $C_3$-$C_{20}$ cycloalkyl group, a $C_3$-$C_{20}$ heterocycloalkyl group, a $C_6$-$C_{20}$ aryl group and a $C_5$-$C_{20}$ heteroaryl group; a $C_2$-$C_{20}$ alkenyl group which is unsubstituted or substituted with at least one group selected from the group consisting of a $C_1$-$C_{20}$ alkyl group, a $C_2$-$C_{20}$ alkenyl group, a $C_2$-$C_{20}$ alkynyl group, a $C_3$-$C_{20}$ cycloalkyl group, a $C_3$-$C_{20}$ heterocycloalkyl group, a $C_6$-$C_{20}$ aryl group and a $C_5$-$C_{20}$ heteroaryl group; a $C_2$-$C_{20}$ alkynyl group which is unsubstituted or substituted with at least one group selected from the group consisting of a $C_1$-$C_{20}$ alkyl group, a $C_2$-$C_{20}$ alkenyl group, a $C_2$-$C_{20}$ alkynyl group, a $C_3$-$C_{20}$ cycloalkyl group, a $C_3$-$C_{20}$ heterocycloalkyl group, a $C_6$-$C_{20}$ aryl group and a $C_5$-$C_{20}$ heteroaryl group; a $C_6$-$C_{20}$ aryl group which is unsubstituted or substituted with at least one group selected from the group consisting of a $C_1$-$C_{20}$ alkyl group, a $C_2$-$C_{20}$ alkenyl group, a $C_2$-$C_{20}$ alkynyl group, a $C_3$-$C_{20}$ cycloalkyl group, a $C_3$-$C_{20}$ heterocycloalkyl group, a $C_6$-$C_{20}$ aryl group and a $C_5$-$C_{20}$ heteroaryl group; or a $C_5$-$C_{20}$ heteroaryl group which is unsubstituted or substituted with at least one group selected from the group consisting of a $C_1$-$C_{20}$ alkyl group, a $C_2$-$C_{20}$ alkenyl group, a $C_2$-$C_{20}$ alkynyl group, a $C_3$-$C_{20}$ cycloalkyl group, a $C_3$-$C_{20}$ heterocycloalkyl group, a $C_6$-$C_{20}$ aryl group and a $C_5$-$C_{20}$ heteroaryl group, and n and m are each an integer of 0 to 3, provided that n+m≧1.

In the compound of the formula 1, $Ar^1$ is preferably a group selected from the group consisting of:

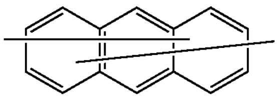

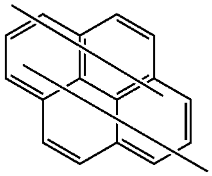

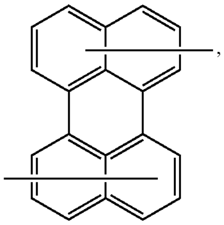

, and these groups may be substituted with at least one group selected from the group consisting of a $C_1$-$C_{20}$ alkyl group, a $C_2$-$C_{20}$ alkenyl group, a $C_2$-$C_{20}$ alkynyl group, a $C_3$-$C_{20}$ cycloalkyl group, a $C_3$-$C_{20}$ heterocycloalkyl group, a $C_6$-$C_{20}$ aryl group and a $C_5$-$C_{20}$ heteroaryl group.

In the compound of the formula 1, $Ar^2$ is preferably a phenyl group, a biphenyl group, a naphthalene group or an anthracene group.

In the compound of the formula 1, L is preferably a direct bond, or is selected from the group consisting of arylene groups such as a phenylene group, a biphenylene group and a naphthalene group, or from the group consisting of heteroarylene groups such as a pyridylene group, a bipyridylene group, a carbazolene group, a thiophenylene group, a quinolylene group and an isoquinolylene group.

In the compound of the formula 1, $Ar^3$ is preferably selected from the group consisting of aryl groups such as a phenyl group, a biphenyl group, a naphthyl group, an anthryl group, a pyrenyl group and a perylenyl group, or from the group consisting of heteroaryl groups such as a pyridyl group, a bipyridyl group, a carbazol group, a thiophenyl group, a quinolinyl group and an isoquinolinyl group.

In the compound of the formula 1, Z is preferably selected from the group consisting of a hydrogen atom,

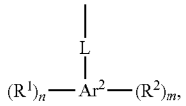

aryl groups such as a phenyl group, a biphenyl group, a naphthyl group, an anthryl group, a pyrenyl group, and a perylenyl group, or from the group consisting of heteroaryl groups such as a pyridyl group, a bipyridyl group, a carbazol group, a thiophenyl group, a quinolinyl group and an isoquinolinyl group.

In the compound of the formula 1, $Ar^1$ is more preferably selected from the anthracenylene groups represented by the following structural formulas, and these groups may be substituted with at least one group selected from the group consisting of a $C_1$-$C_{20}$ alkyl group, a $C_2$-$C_{20}$ alkenyl group, a $C_2$-$C_{20}$ alkynyl group, a $C_3$-$C_{20}$ cycloalkyl group, a $C_3$-$C_{20}$ heterocycloalkyl group, a $C_6$-$C_{20}$ aryl group and a $C_5$-$C_{20}$ heteroaryl group.

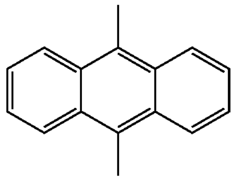

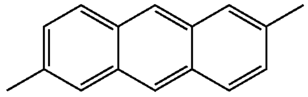

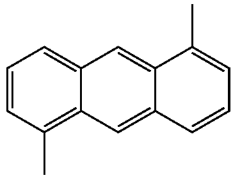

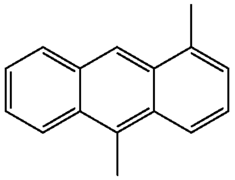

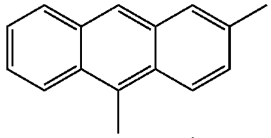

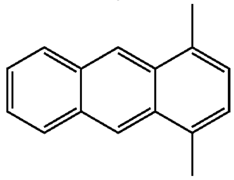

The definition of the substituents as used in the present invention is as follows.

The alkyl group preferably has 1 to 20 carbon atoms. Specific examples thereof include a methyl group, an ethyl group, a propyl group, an isopropyl group, a butyl group, a t-butyl group, a pentyl group, a hexyl group and a heptyl group, but are not limited thereto.

The alkenyl group preferably has 2 to 20 carbon atoms. Specific examples thereof include a methenyl group, an ethenyl group and a propylenyl group, but are not limited thereto.

The cycloalkyl group preferably has 3 to 20 carbon atoms, and does not give steric hindrance. Specific examples thereof more preferably include a cyclopentyl group or a cyclohexyl group, but are not limited thereto.

The aryl group includes those selected from the group consisting of a phenyl group, a naphthyl group, an anthracenyl group, a biphenyl group, a pyrenyl group and a perylene group, but is not limited thereto.

The heteroaryl group includes those selected from the group consisting of a pyridyl group, a bipyridyl group, an acridyl group, a thiophene group, an imidazole group, an oxazole group, a thiazole group and a quinolinyl group, but is not limited thereto.

The arylamine group is preferably an amine group which is substituted with a $C_6$-$C_{20}$ aryl group, and the aryl group may be substituted with an arylalkenyl group, but is not limited thereto.

The compound of the formula 1 can be a compound represented by the following formula 2.

[Formula 2]

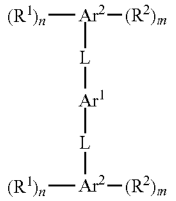

wherein $Ar^1$, $Ar^2$, L, $R^1$, $R^2$, n and m have the same meanings as defined in the formula 1.

Further, the compound of the formula 1 can be a compound represented by the following formula 3.

[Formula 3]

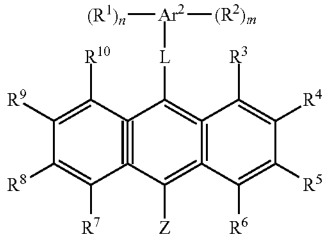

wherein $Ar^2$, L, $R^1$, $R^2$, n, m and Z have the same meanings as defined in the formula 1, $R^3$ to $R^{10}$ are the same or different from each other, are independently selected from the group consisting of a hydrogen atom, a substituted or unsubstituted $C_1$-$C_{20}$ alkyl group, a substituted or unsubstituted $C_2$-$C_{20}$ alkenyl group, a substituted or unsubstituted $C_2$-$C_{20}$ alkynyl group, a substituted or unsubstituted $C_3$-$C_{20}$ cycloalkyl group, a substituted or unsubstituted $C_3$-$C_{20}$ heterocycloalkyl group, a substituted or unsubstituted $C_6$-$C_{20}$ aryl group, a substituted or unsubstituted $C_5$-$C_{20}$ heteroaryl group, and a substituted or unsubstituted arylamine group.

In the formula 3, $R^3$, $R^5$ to $R^7$, $R^9$ and $R^{10}$ are hydrogen atoms, $R^4$ and $R^8$ are the same or different from each other, are preferably independently selected from the group consisting of a substituted or unsubstituted $C_1$-$C_{20}$ alkyl group, a substituted or unsubstituted $C_2$-$C_{20}$ alkenyl group, a substituted or unsubstituted $C_2$-$C_{20}$ alkynyl group, a substituted or unsubstituted $C_3$-$C_{20}$ cycloalkyl group, a substituted or unsubstituted $C_3$-$C_{20}$ heterocycloalkyl group, a substituted or unsubstituted $C_6$-$C_{20}$ aryl group, a substituted or unsubstituted $C_5$-$C_{20}$ heteroaryl group, and a substituted or unsubstituted arylamine group.

Further, the compound of the formula 1 can be a compound represented by the following formula 4.

[Formula 4]

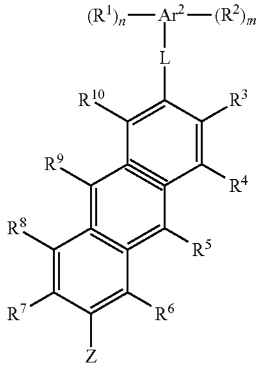

wherein $Ar^2$, L, $R^1$, $R^2$, n, m and Z have the same meanings as defined in the formula 1, $R^3$ to $R^{10}$ are the same or different from each other, are independently selected from the group consisting of a hydrogen atom, a substituted or unsubstituted $C_1$-$C_{20}$ alkyl group, a substituted or unsubstituted $C_2$-$C_{20}$ alkenyl group, a substituted or unsubstituted $C_2$-$C_{20}$ alkynyl group, a substituted or unsubstituted $C_3$-$C_{20}$ cycloalkyl group, a substituted or unsubstituted $C_3$-$C_{20}$ heterocycloalkyl group, a substituted or unsubstituted $C_6$-$C_{20}$ aryl group, a substituted or unsubstituted $C_5$-$C_{20}$ heteroaryl group, and a substituted or unsubstituted arylamine group.

In the formula 4, $R^3$, $R^4$, $R^6$ to $R^8$ and $R^{10}$ are hydrogen atoms, and $R^5$ and $R^9$ are the same or different from each other, are preferably independently selected from the group consisting of a substituted or unsubstituted $C_1$-$C_{20}$ alkyl group, a substituted or unsubstituted $C_2$-$C_{20}$ alkenyl group, a substituted or unsubstituted $C_2$-$C_{20}$ alkynyl group, a substituted or unsubstituted $C_3$-$C_{20}$ cycloalkyl group, a substituted or unsubstituted $C_3$-$C_{20}$ heterocycloalkyl group, a substituted or unsubstituted $C_6$-$C_{20}$ aryl group, a substituted or unsubstituted $C_5$-$C_{20}$ heteroaryl group, and a substituted or unsubstituted arylamine group.

Specific examples of the compound of the formula 1 are presented in the following Tables 1 to 6, but are not limited thereto.

The following Table 1 presents specific examples of the compound having an asymmetric structure, wherein in the formula l, m is equal to 0.

TABLE 1

| | $Ar^1$ | L | $Ar^2$ | $R^1$ |
|---|---|---|---|---|
| 1 | 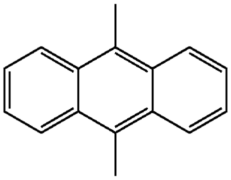 | Direct bond | 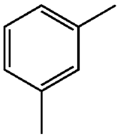 | 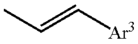 |
| 2 | 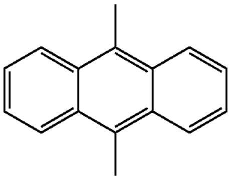 | Direct bond | 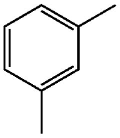 | 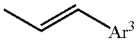 |
| 3 | 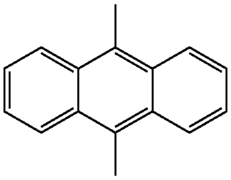 | Direct bond | 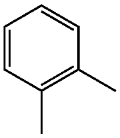 | 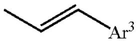 |
| 4 | 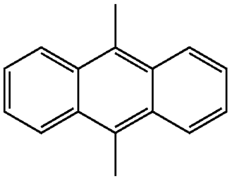 | Direct bond | 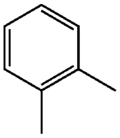 | 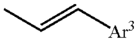 |
| 5 | 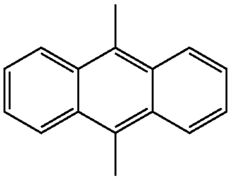 | Direct bond | 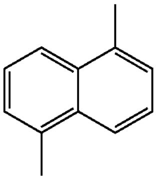 | 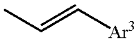 |
| 6 | 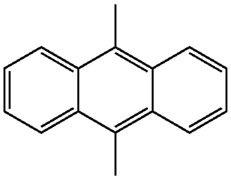 | Direct bond | 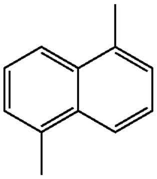 | 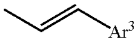 |

TABLE 1-continued
| | | | | |
|---|---|---|---|---|
| 7 | 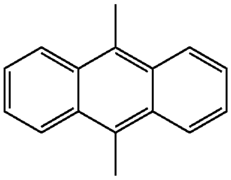 | Direct bond | 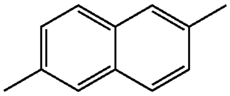 | 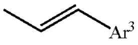 |
| 8 | 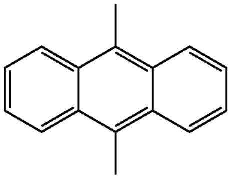 | Direct bond | 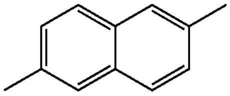 | 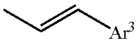 |
| 9 | 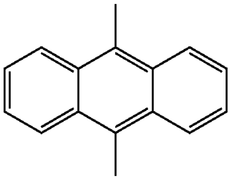 | Direct bond | 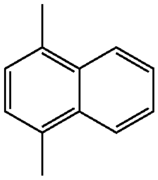 | 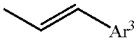 |
| 10 | 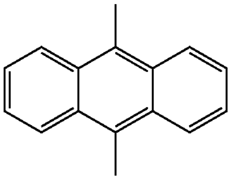 | Direct bond | 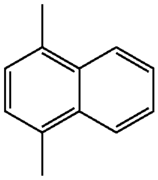 | 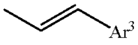 |
| 11 | 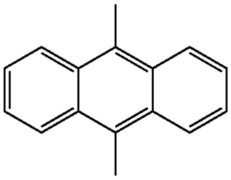 | Direct bond | 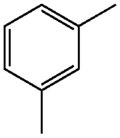 | 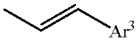 |
| 12 | 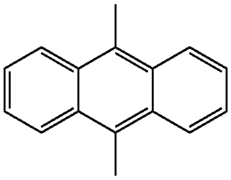 | 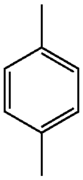 | 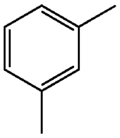 | 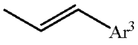 |
| 13 | 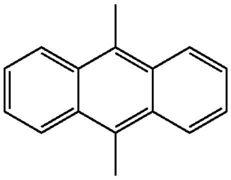 | 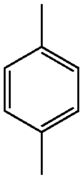 | 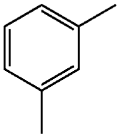 | 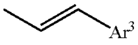 |
| 14 | 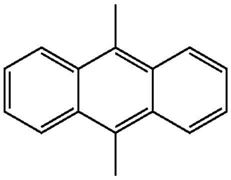 | 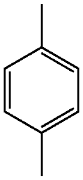 | 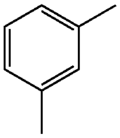 | 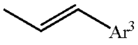 |

TABLE 1-continued
| | | | | |
|---|---|---|---|---|
| 15 | 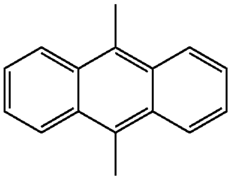 | 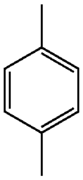 | 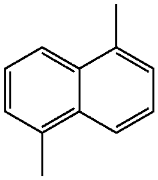 | 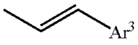 |
| 16 | 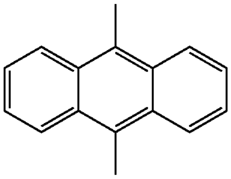 | 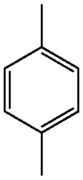 | 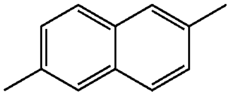 | 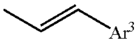 |
| 17 | 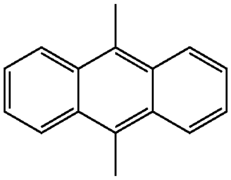 | 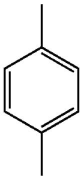 | 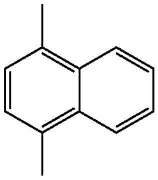 | 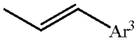 |
| 18 | 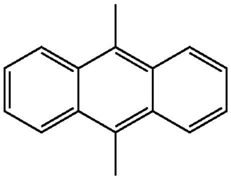 | 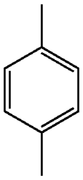 | 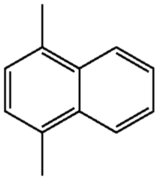 | 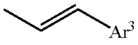 |
| 19 | 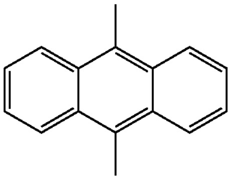 | 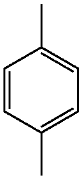 | 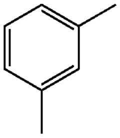 | 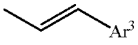 |
| 20 | 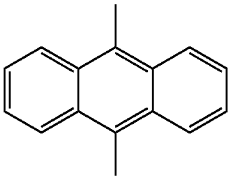 | 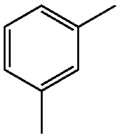 | 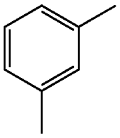 | 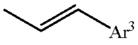 |
| 21 | 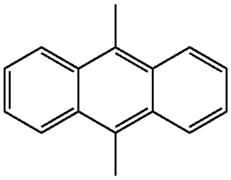 | 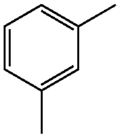 | 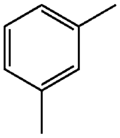 | 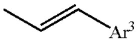 |
| 22 | 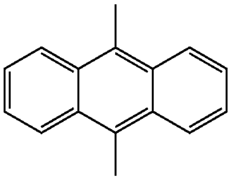 | 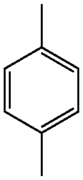 | 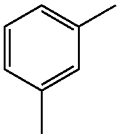 | 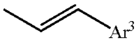 |

TABLE 1-continued
| | | | | |
|---|---|---|---|---|
| 23 | 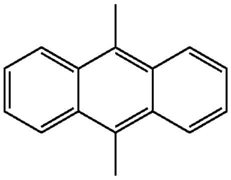 | 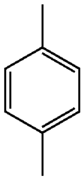 | 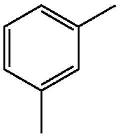 | 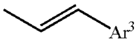 |
| 24 | 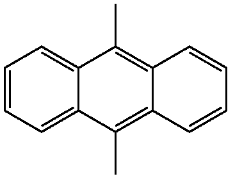 | 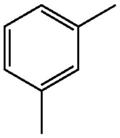 | 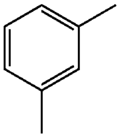 | 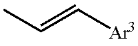 |
| 25 | 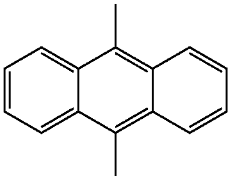 | 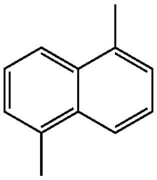 | 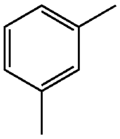 | 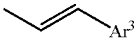 |
| 26 | 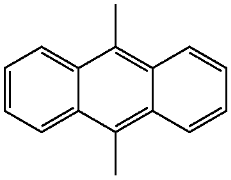 | 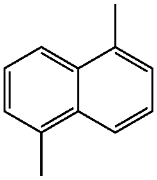 | 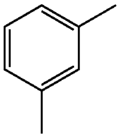 | 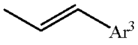 |
| 27 | 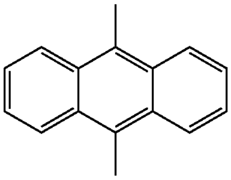 | 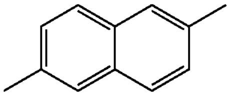 | 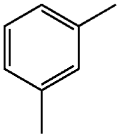 | 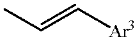 |
| 28 | 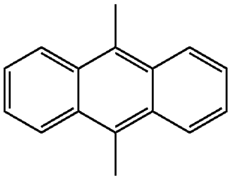 | 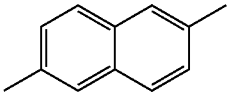 | 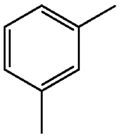 | 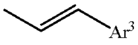 |
| 29 | 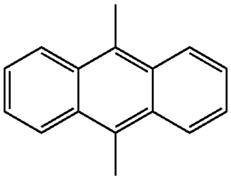 | 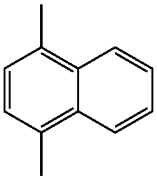 | 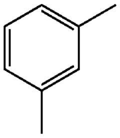 | 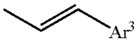 |
| 30 | 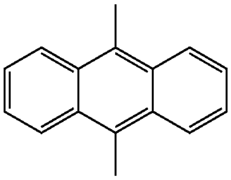 | 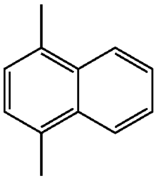 | 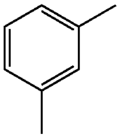 | 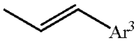 |

TABLE 1-continued
| | | | | |
|---|---|---|---|---|
| 31 | 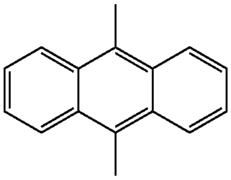 | 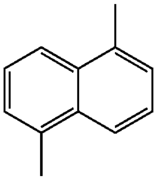 | 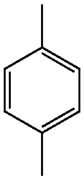 | 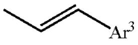 |
| 32 | 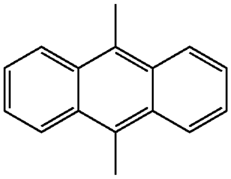 | 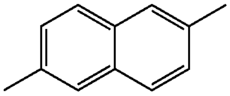 | 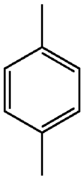 | 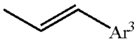 |
| 33 | 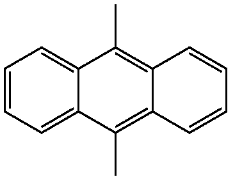 | 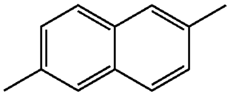 | 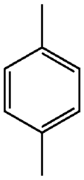 | 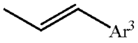 |
| 34 | 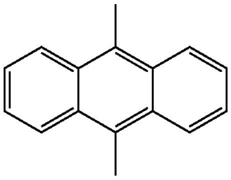 | 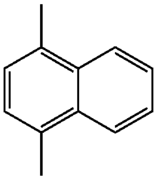 | 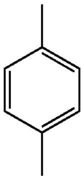 | 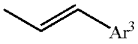 |
| 35 | 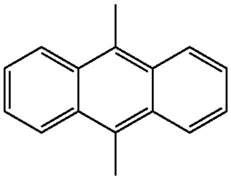 | 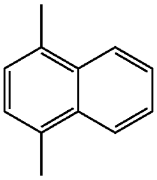 | 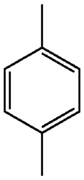 | 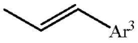 |
| 36 | 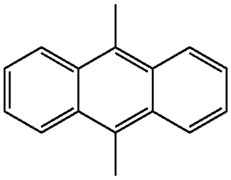 | 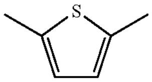 | 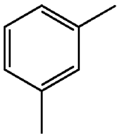 | 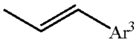 |
| 37 | 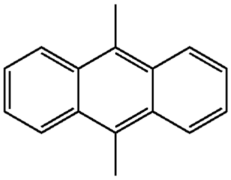 | 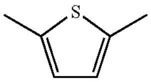 | 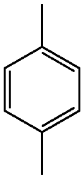 | 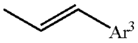 |
| 38 | 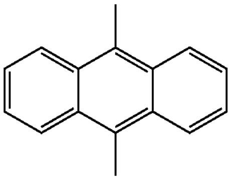 | 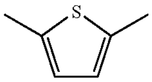 | 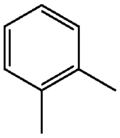 | 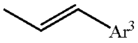 |

TABLE 1-continued
| | | | | |
|---|---|---|---|---|
| 39 | 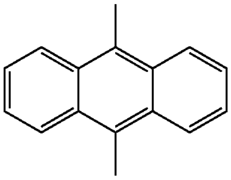 | 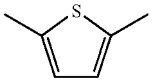 | 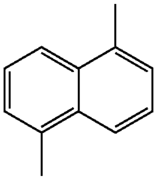 | 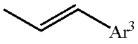 |
| 40 | 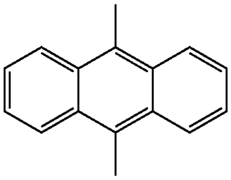 | 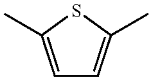 | 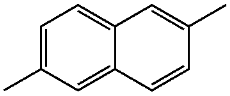 | 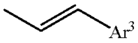 |
| 41 | 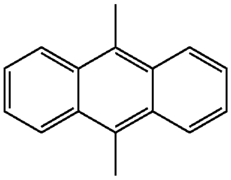 | 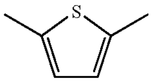 | 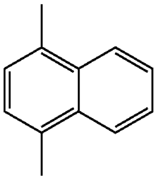 | 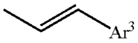 |
| 42 | 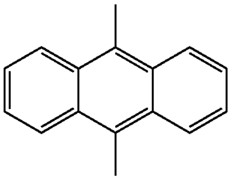 | 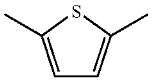 | 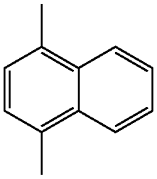 | 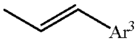 |
| 43 | 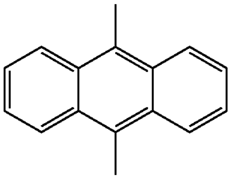 | 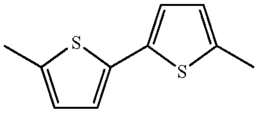 | 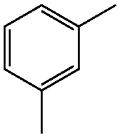 | 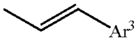 |
| 44 | 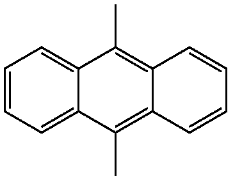 | 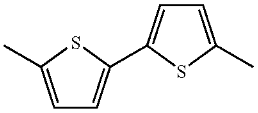 | 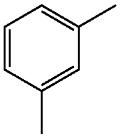 | 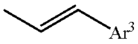 |
| 45 | 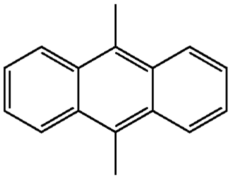 | 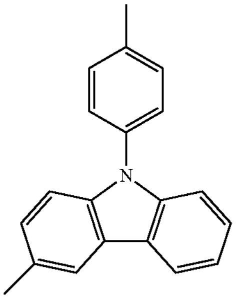 | 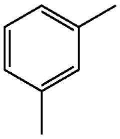 | 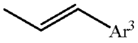 |

TABLE 1-continued
| | | | | |
|---|---|---|---|---|
| 46 | 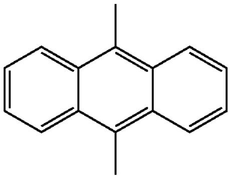 | 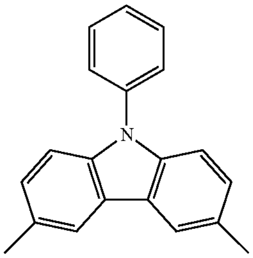 | 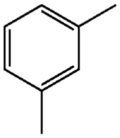 | 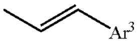 |
| 47 | 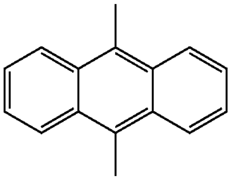 | 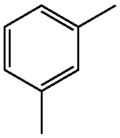 | 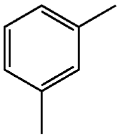 | 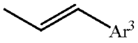 |
| 48 | 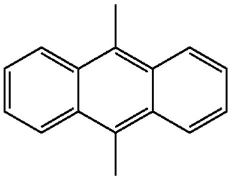 | 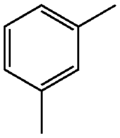 | 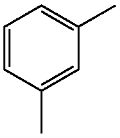 | 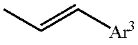 |
| 49 | 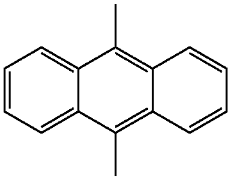 | 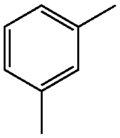 | 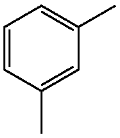 | 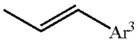 |
| 50 | 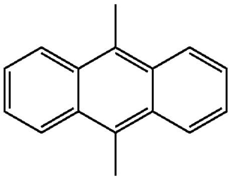 | Direct bond | 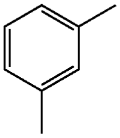 | 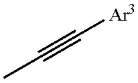 |
| 51 | 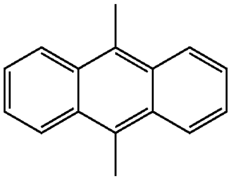 | Direct bond | 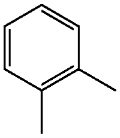 | 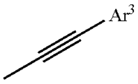 |
| 52 | 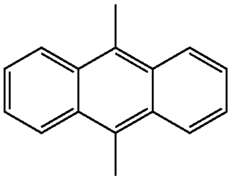 | Direct bond | 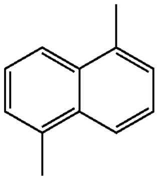 | 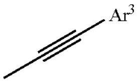 |
| 53 | 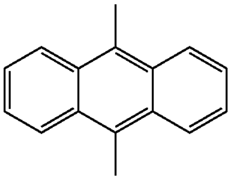 | Direct bond | 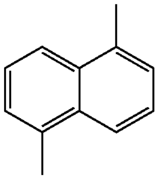 | 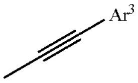 |

TABLE 1-continued
| | | | | |
|---|---|---|---|---|
| 54 | 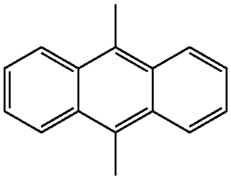 | Direct bond | 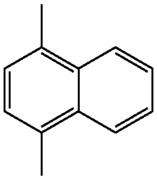 | 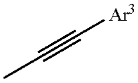 |
| 55 | 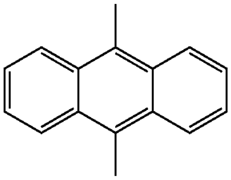 | Direct bond | 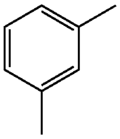 | 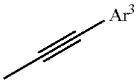 |
| 56 | 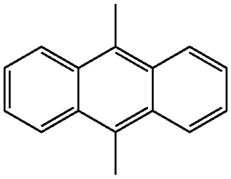 | 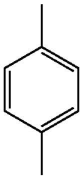 | 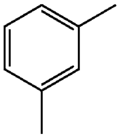 | 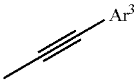 |
| 57 | 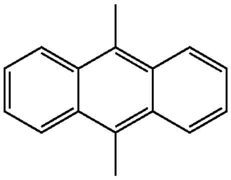 | 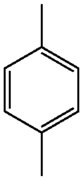 | 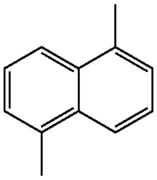 | 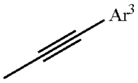 |
| 58 | 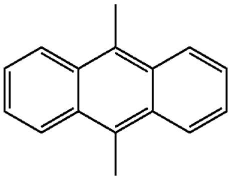 | Direct bond | 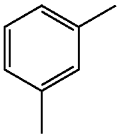 | 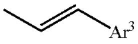 |
| 59 | 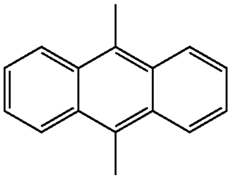 | Direct bond | 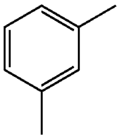 | 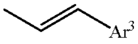 |
| 60 | 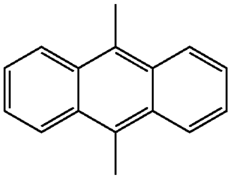 | Direct bond | 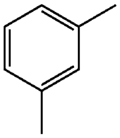 | 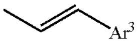 |
| | $Ar^3$ | Z |
|---|---|---|
| 1 | 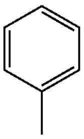 | 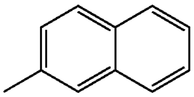 |

TABLE 1-continued
| | | |
|---|---|---|
| 2 | 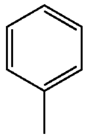 | 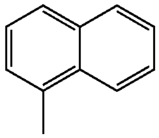 |
| 3 | 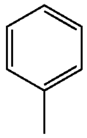 | 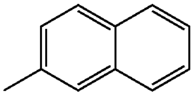 |
| 4 | 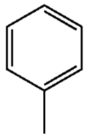 | 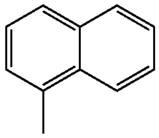 |
| 5 | 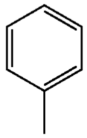 | 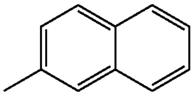 |
| 6 | 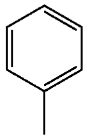 | 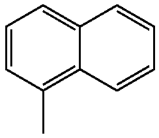 |
| 7 | 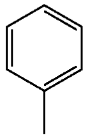 | 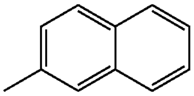 |
| 8 | 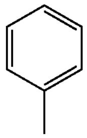 | 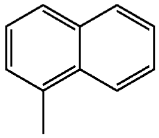 |
| 9 | 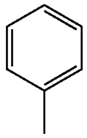 | 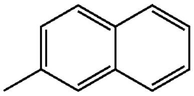 |
| 10 | 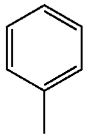 | 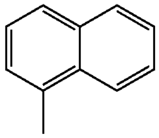 |
| 11 | 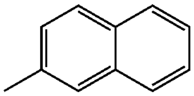 | 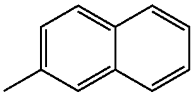 |
| 12 | 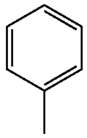 | 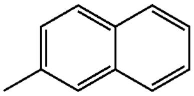 |

TABLE 1-continued
| | | |
|---|---|---|
| 13 | 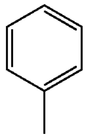 | 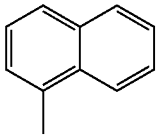 |
| 14 | 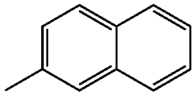 | 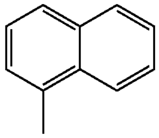 |
| 15 | 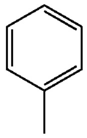 | 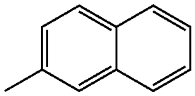 |
| 16 | 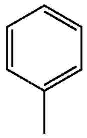 | 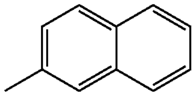 |
| 17 | 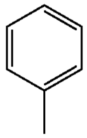 | 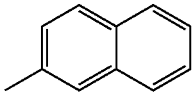 |
| 18 | 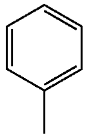 | 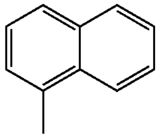 |
| 19 | 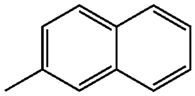 | 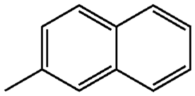 |
| 20 | 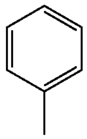 | 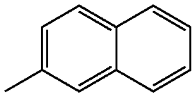 |
| 21 | 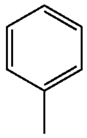 | 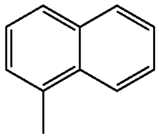 |
| 22 | 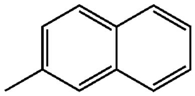 | 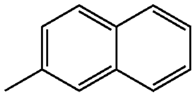 |
| 23 | 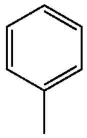 | 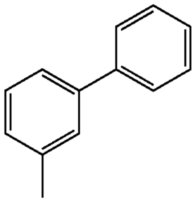 |

TABLE 1-continued
| | | |
|---|---|---|
| 24 | 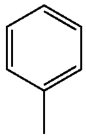 | 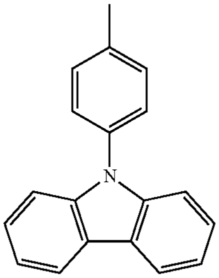 |
| 25 | 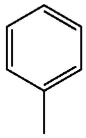 | 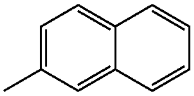 |
| 26 | 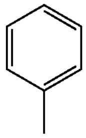 | 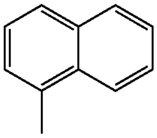 |
| 27 | 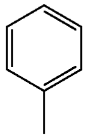 | 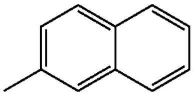 |
| 28 | 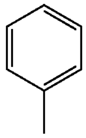 | 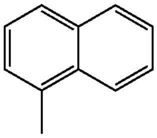 |
| 29 | 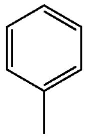 | 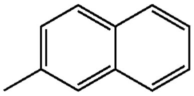 |
| 30 | 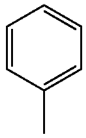 | 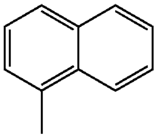 |
| 31 | 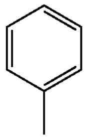 | 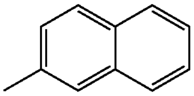 |
| 32 | 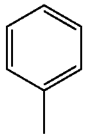 | 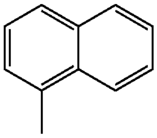 |

TABLE 1-continued
| | | |
|---|---|---|
| 33 | 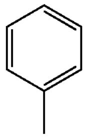 | 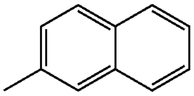 |
| 34 | 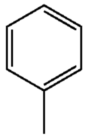 | 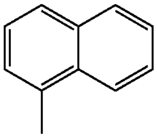 |
| 35 | 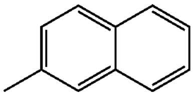 | 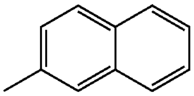 |
| 36 | 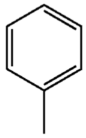 | 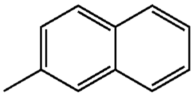 |
| 37 | 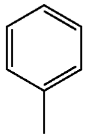 | 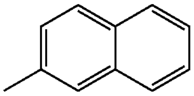 |
| 38 | 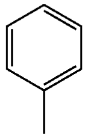 | 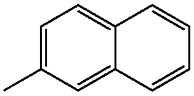 |
| 39 | 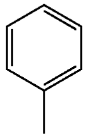 | 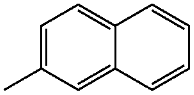 |
| 40 | 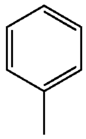 | 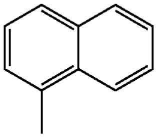 |
| 41 | 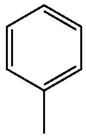 | 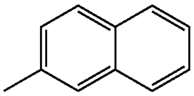 |
| 42 | 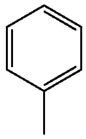 | 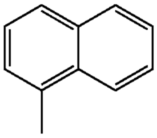 |
| 43 | 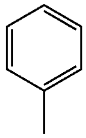 | 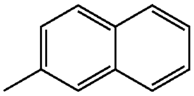 |

TABLE 1-continued
| | | |
|---|---|---|
| 44 | 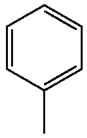 | 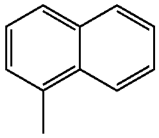 |
| 45 | 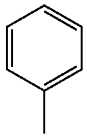 | 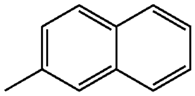 |
| 46 | 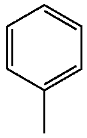 | 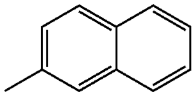 |
| 47 | 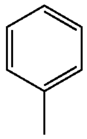 | 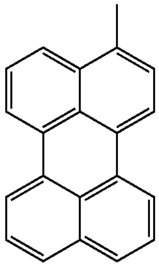 |
| 48 | 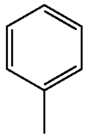 | 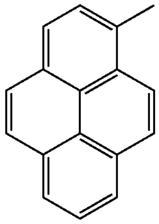 |
| 49 | 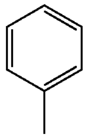 | 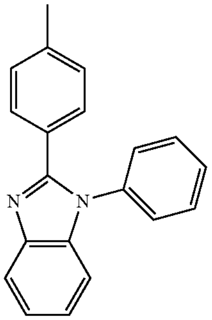 |
| 50 | 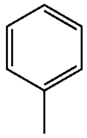 | 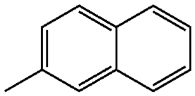 |
| 51 | 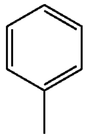 | 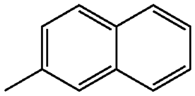 |

TABLE 1-continued
| | | |
|---|---|---|
| 52 | 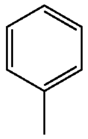 | 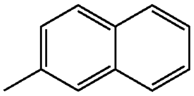 |
| 53 | 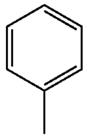 | 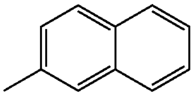 |
| 54 | 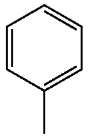 | 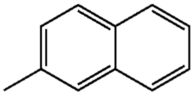 |
| 55 | 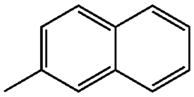 | 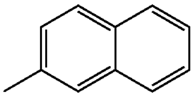 |
| 56 | 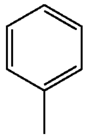 | 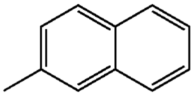 |
| 57 | 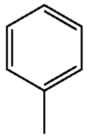 | 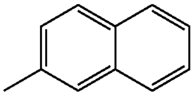 |
| 58 | 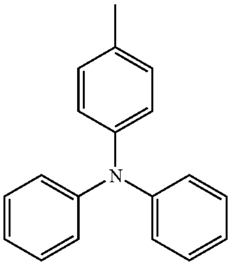 | 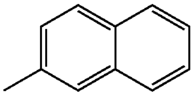 |
| 59 | 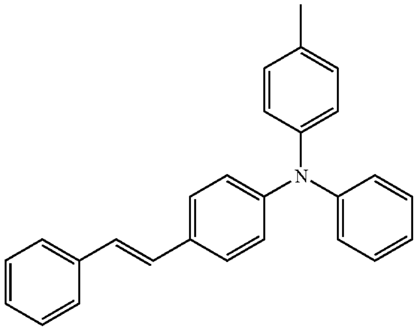 | 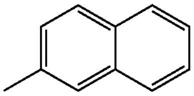 |

TABLE 1-continued
| | | |
|---|---|---|
| 60 | 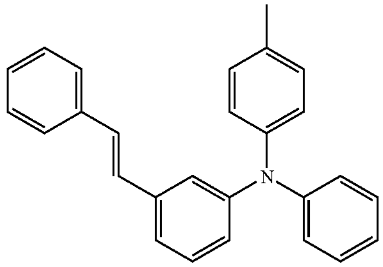 | 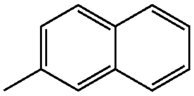 |
The following Table 2 presents specific examples of the compound having an asymmetric structure, wherein in the formula 1, neither n nor m is not 0.
TABLE 2
| | $Ar^1$ | L | $Ar^2$ | $R^1$ and $R^2$ | $Ar^3$ | Z |
|---|---|---|---|---|---|---|
| 61 | 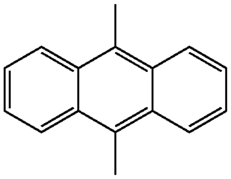 | Direct bond | 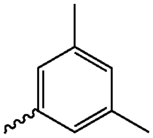 | 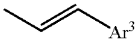 | 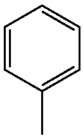 | 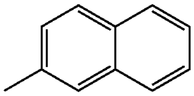 |
| 62 | 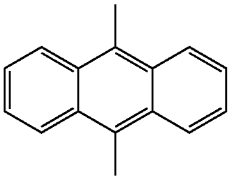 | Direct bond | 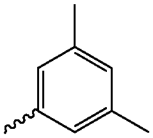 | 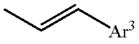 | 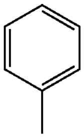 | 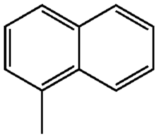 |
| 63 | 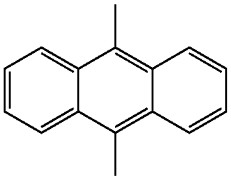 | Direct bond | 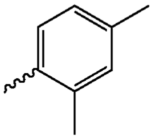 | 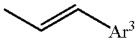 | 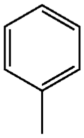 | 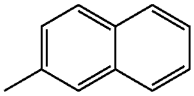 |
| 64 | 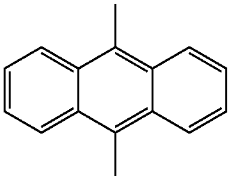 | Direct bond | 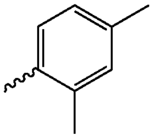 | 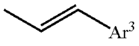 | 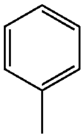 | 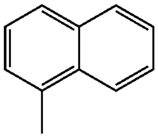 |
| 65 | 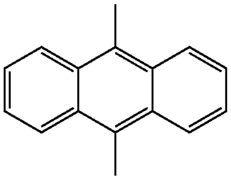 | Direct bond | 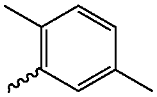 | 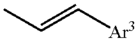 | 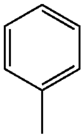 | 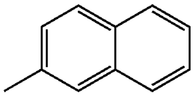 |
| 66 | 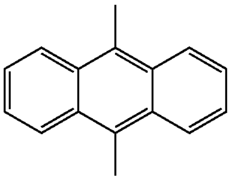 | Direct bond | 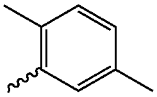 | 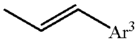 | 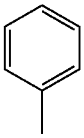 | 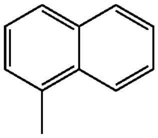 |

TABLE 2-continued
| | Ar[1] | L | Ar[2] | $R^1$ and $R^2$ | Ar[3] | Z |
|---|---|---|---|---|---|---|
| 67 | 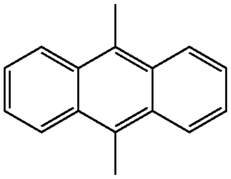 | Direct bond | 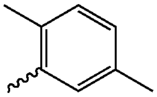 | 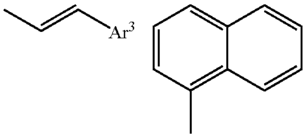 | | 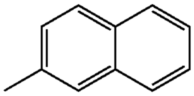 |
| 68 | 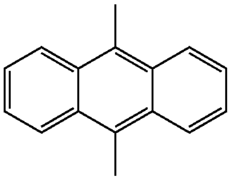 | 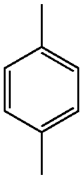 | 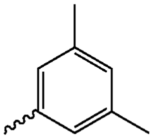 | 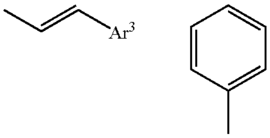 | | 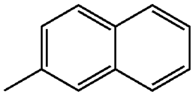 |
| 69 | 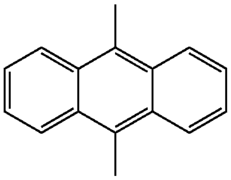 | 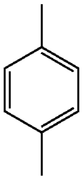 | 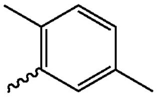 | 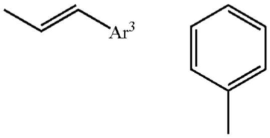 | | 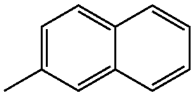 |
| 70 | 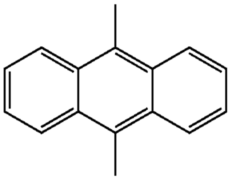 | 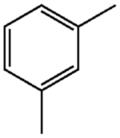 | 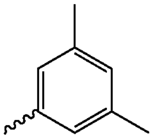 | 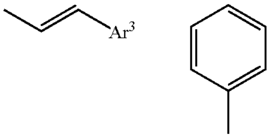 | | 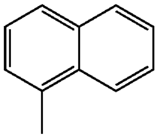 |
| 71 | 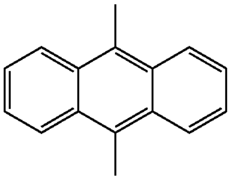 | 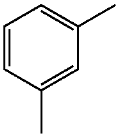 | 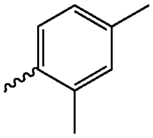 | 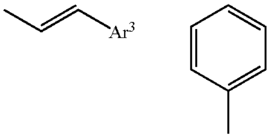 | | 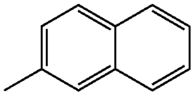 |
| 72 | 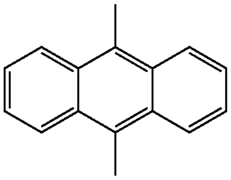 | 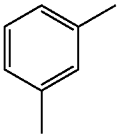 | 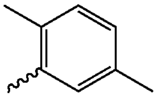 | 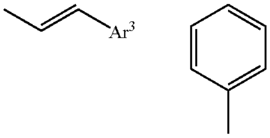 | | 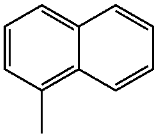 |
| 73 | 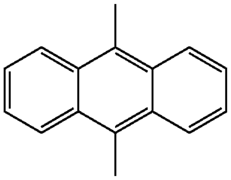 | 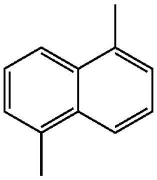 | 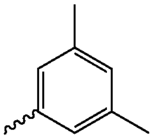 | 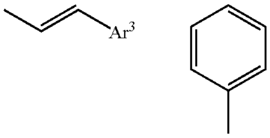 | | 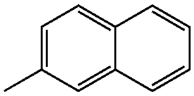 |
| 74 | 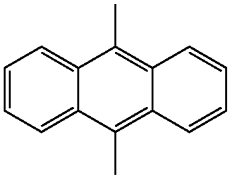 | 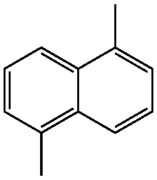 | 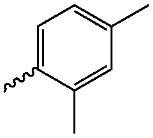 | 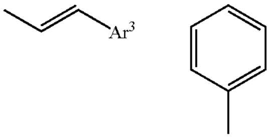 | | 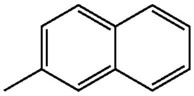 |

TABLE 2-continued
| | $Ar^1$ | L | $Ar^2$ | $R^1$ and $R^2$ | $Ar^3$ | Z |
|---|---|---|---|---|---|---|
| 75 | 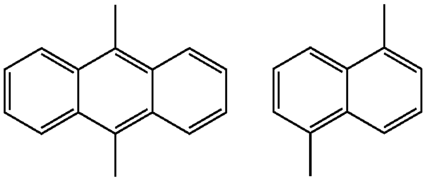 | | 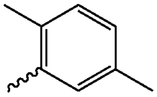 | 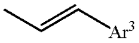 | 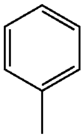 | 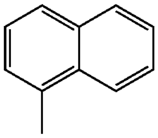 |
| 76 | 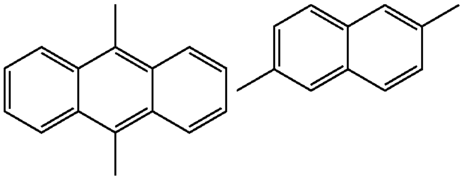 | | 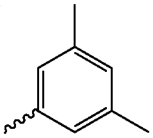 | 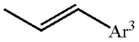 | 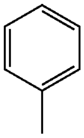 | 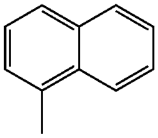 |
| 77 | 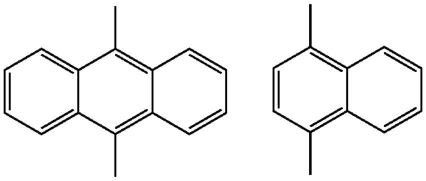 | | 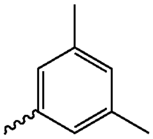 | 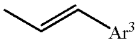 | 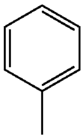 | 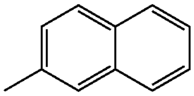 |
| 78 | 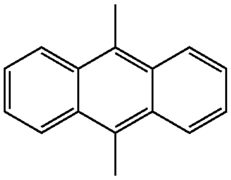 | Direct bond | 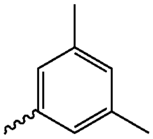 | 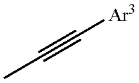 | 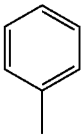 | 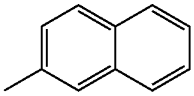 |
| 79 | 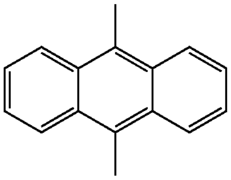 | Direct bond | 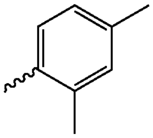 | 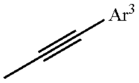 | 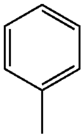 | 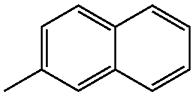 |
| 80 | 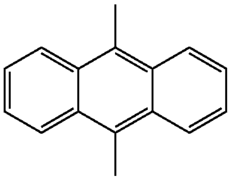 | Direct bond | 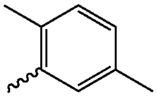 | 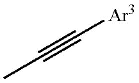 | 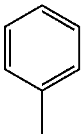 | 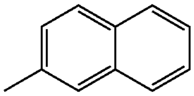 |
| 81 | 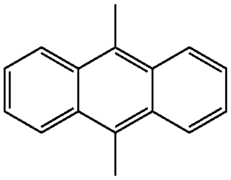 | Direct bond | 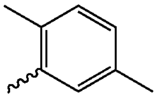 | 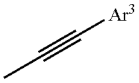 | 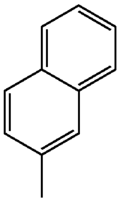 | 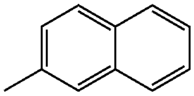 |
| 82 | 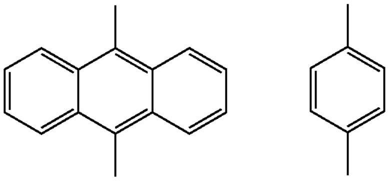 | | 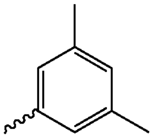 | 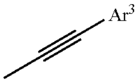 | 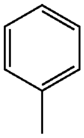 | 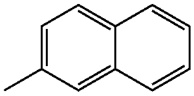 |

TABLE 2-continued
| | $Ar^1$ | L | $Ar^2$ | $R^1$ and $R^2$ | $Ar^3$ | Z |
|---|---|---|---|---|---|---|
| 83 | 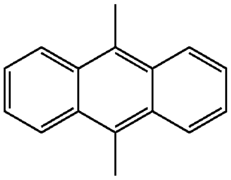 | 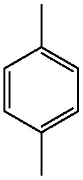 | 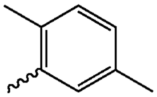 | 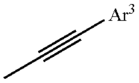 | 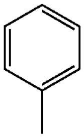 | 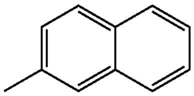 |
| 84 | 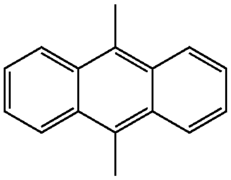 | 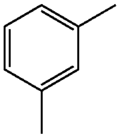 | 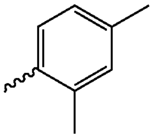 | 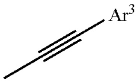 | 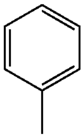 | 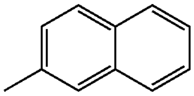 |
| 85 | 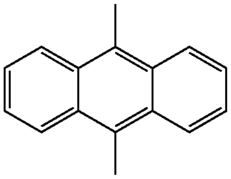 | 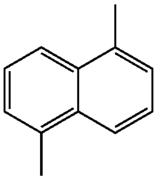 | 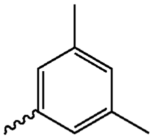 | 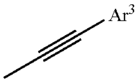 | 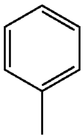 | 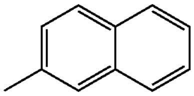 |
| 86 | 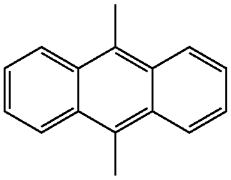 | 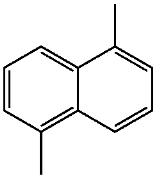 | 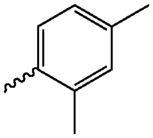 | 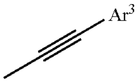 | 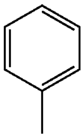 | 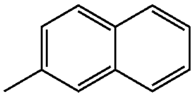 |
| 87 | 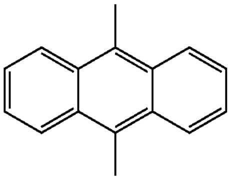 | 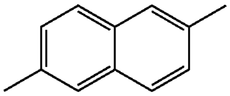 | 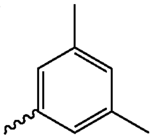 | 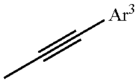 | 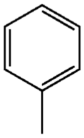 | 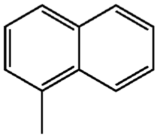 |
| 88 | 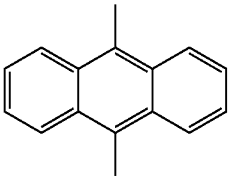 | 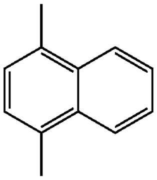 | 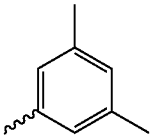 | 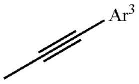 | 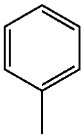 | 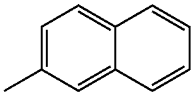 |
Wherein in $Ar^2$ represents a portion to which L is bonded.
The following Table 3 presents specific examples of the compound having a symmetric structure, wherein in the formula 2, n+m is equal to 1.
TABLE 3
| | $Ar^1$ | L | $Ar^2$ | $R^1$ or $R^2$ | $Ar^3$ |
|---|---|---|---|---|---|
| 89 | 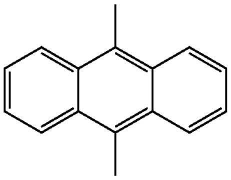 | Direct bond | 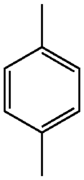 | 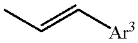 | 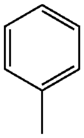 |

TABLE 3-continued
| | $Ar^1$ | L | $Ar^2$ | $R^1$ or $R^2$ | $Ar^3$ |
|---|---|---|---|---|---|
| 90 | 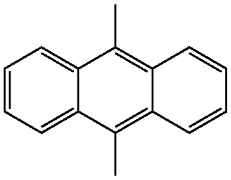 | Direct bond | 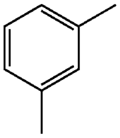 | 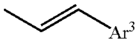 | 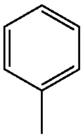 |
| 91 | 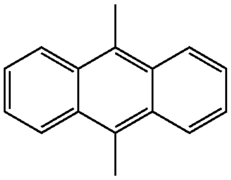 | Direct bond | 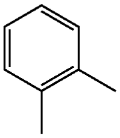 | 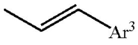 | 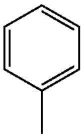 |
| 92 | 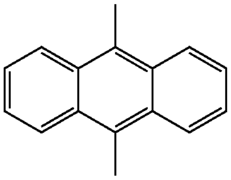 | Direct bond | 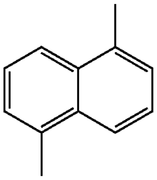 | 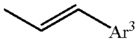 | 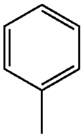 |
| 93 | 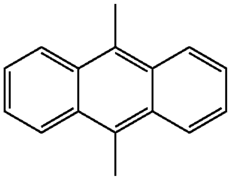 | Direct bond | 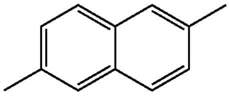 | 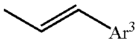 | 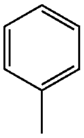 |
| 94 | 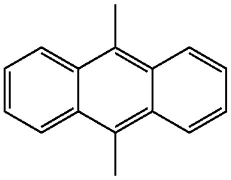 | Direct bond | 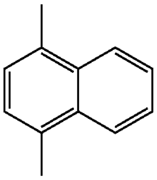 | 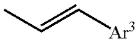 | 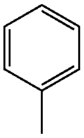 |
| 95 | 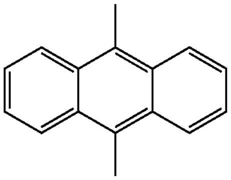 | 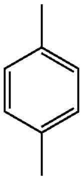 | 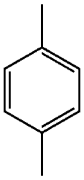 | 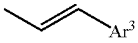 | 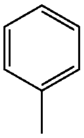 |
| 96 | 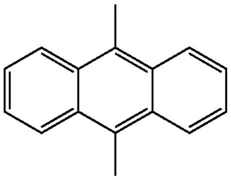 | 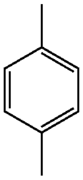 | 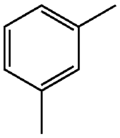 | 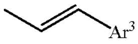 | 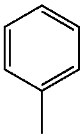 |
| 97 | 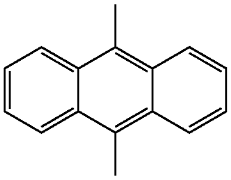 | 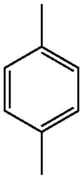 | 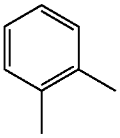 | 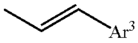 | 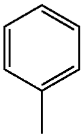 |

TABLE 3-continued
| | Ar[1] | L | Ar[2] | R[1] or R[2] | Ar[3] |
|---|---|---|---|---|---|
| 98 | 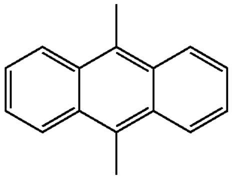 | 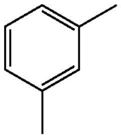 | 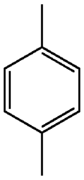 | 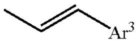 | 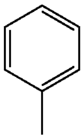 |
| 99 | 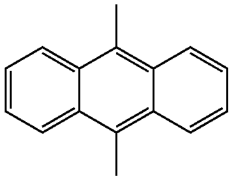 | 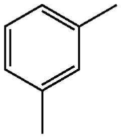 | 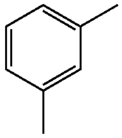 | 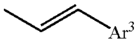 | 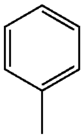 |
| 100 | 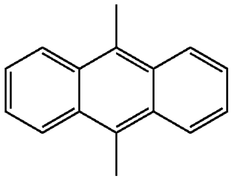 | 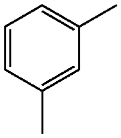 | 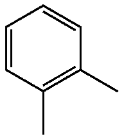 | 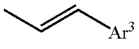 | 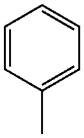 |
| 101 | 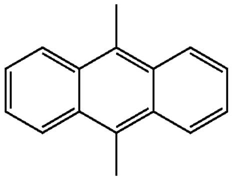 | 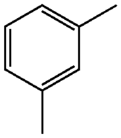 | 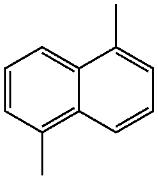 | 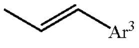 | 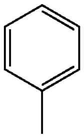 |
| 102 | 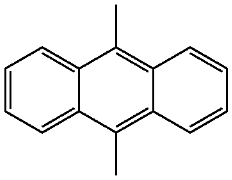 | 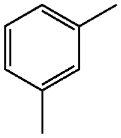 | 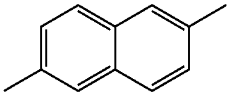 | 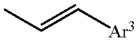 | 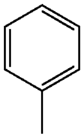 |
| 103 | 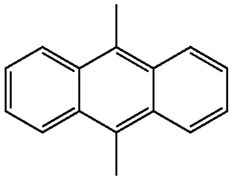 | 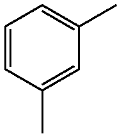 | 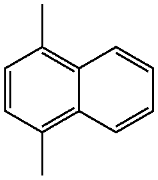 | 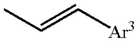 | 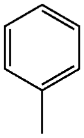 |
| 104 | 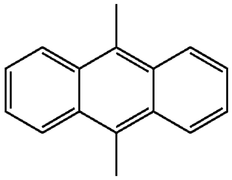 | 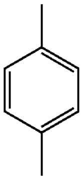 | 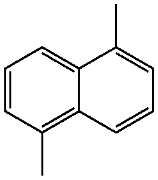 | 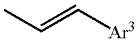 | 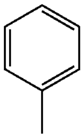 |
| 105 | 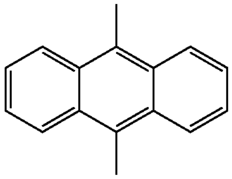 | 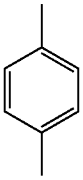 | 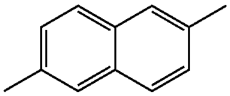 | 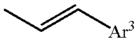 | 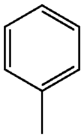 |

TABLE 3-continued
| | $Ar^1$ | L | $Ar^2$ | $R^1$ or $R^2$ | $Ar^3$ |
|---|---|---|---|---|---|
| 106 | 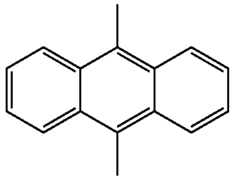 | 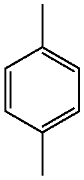 | 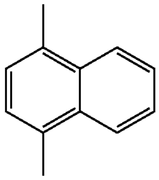 | 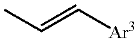 | 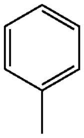 |
| 107 | 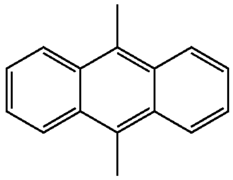 | 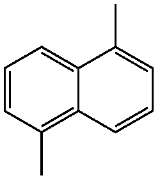 | 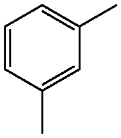 | 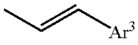 | 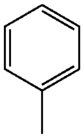 |
| 108 | 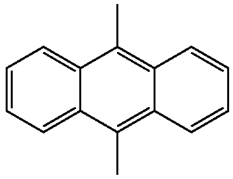 | 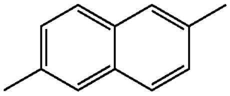 | 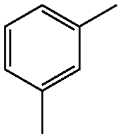 | 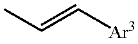 | 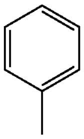 |
| 109 | 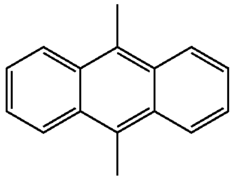 | 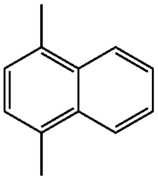 | 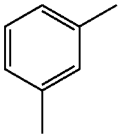 | 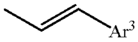 | 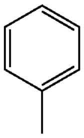 |
The following Table 4 presents specific examples of the compound having a symmetric structure, wherein in the formula 2, n is equal to 1 and m is equal to 1.
TABLE 4
| | $Ar^1$ | L | $Ar_2$ | $R^1$ and $R^2$ | $Ar^3$ |
|---|---|---|---|---|---|
| 110 | 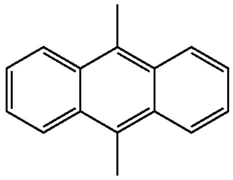 | Direct bond | 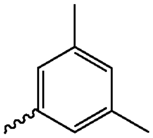 | 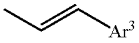 | 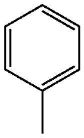 |
| 111 | 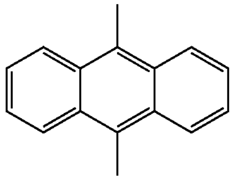 | Direct bond | 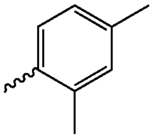 | 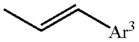 | 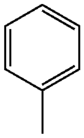 |
| 112 | 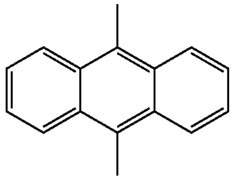 | Direct bond | 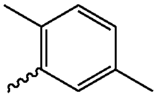 | 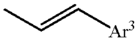 | 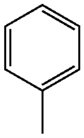 |

TABLE 4-continued
| | $Ar^1$ | L | $Ar_2$ | $R^1$ and $R^2$ | $Ar^3$ |
|---|---|---|---|---|---|
| 113 | 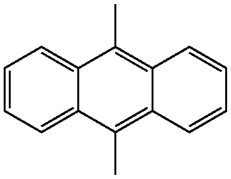 | 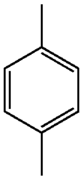 | 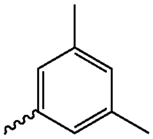 | 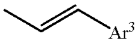 | 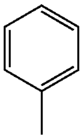 |
| 114 | 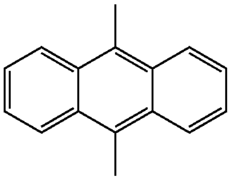 | 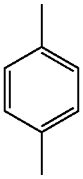 | 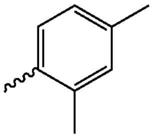 | 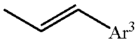 | 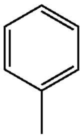 |
| 115 | 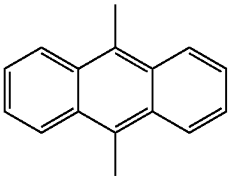 | 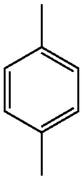 | 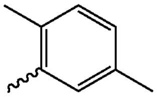 | 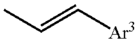 | 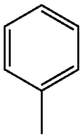 |
| 116 | 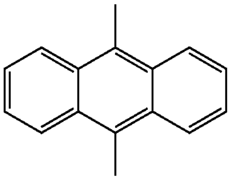 | 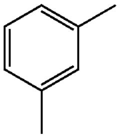 | 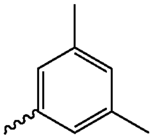 | 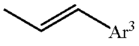 | 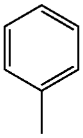 |
| 117 | 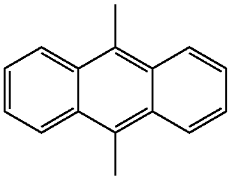 | 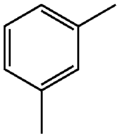 | 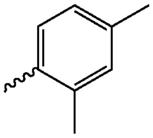 | 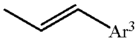 | 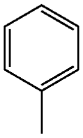 |
| 118 | 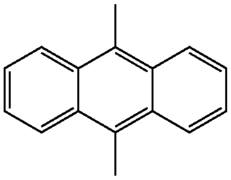 | 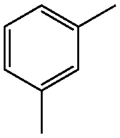 | 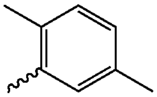 | 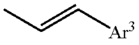 | 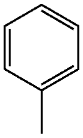 |
| 119 | 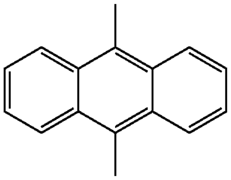 | 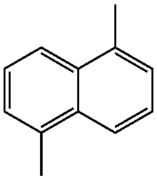 | 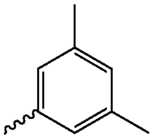 | 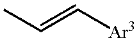 | 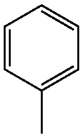 |
| 120 | 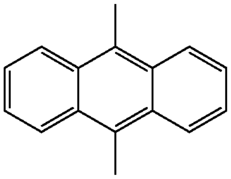 | 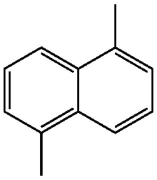 | 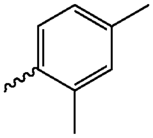 | 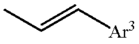 | 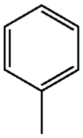 |

TABLE 4-continued
| | Ar[1] | L | $Ar_2$ | $R^1$ and $R^2$ | $Ar^3$ |
|---|---|---|---|---|---|
| 121 | 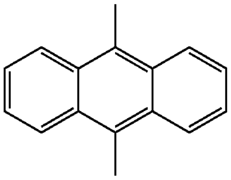 | 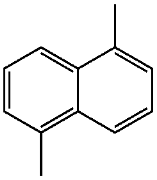 | 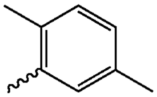 | 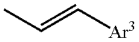 | 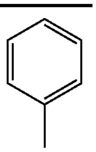 |
| 122 | 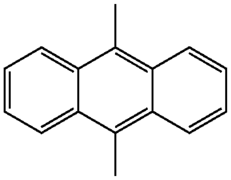 | 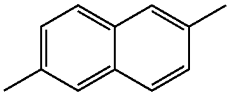 | 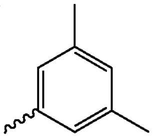 | 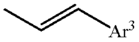 | 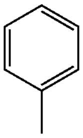 |
| 123 | 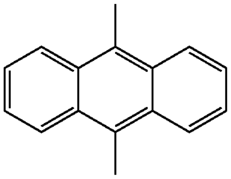 | 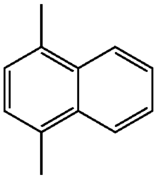 | 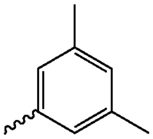 | 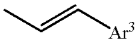 | 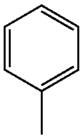 |
Wherein  in $Ar^2$ represents a portion to which L is bonded.
The following Table 5 presents specific examples of the compound having an asymmetric structure, wherein in the formula l, m is equal to 0, and Ar1 has a substituent.
TABLE 5
| | $Ar^1$ | L | $Ar^2$ |
|---|---|---|---|
| 124 | 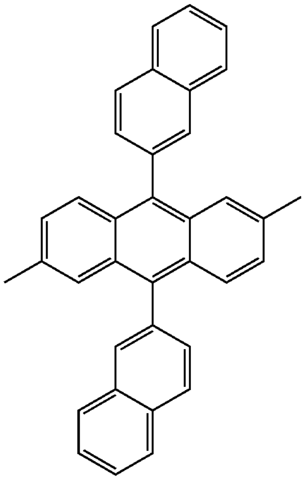 | Direct bond | 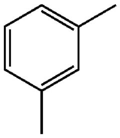 |

TABLE 5-continued
| | | | |
|---|---|---|---|
| 125 | 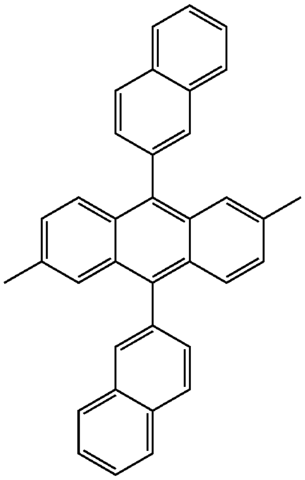 | Direct bond | 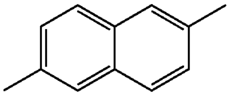 |
| 126 | 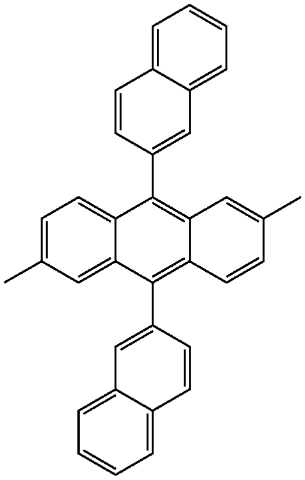 | Direct bond | 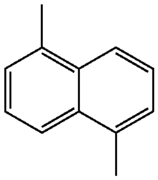 |
| 127 | 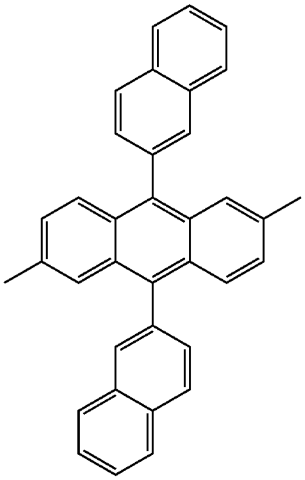 | Direct bond | 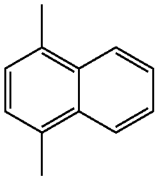 |

TABLE 5-continued
| | | | |
|---|---|---|---|
| 128 | 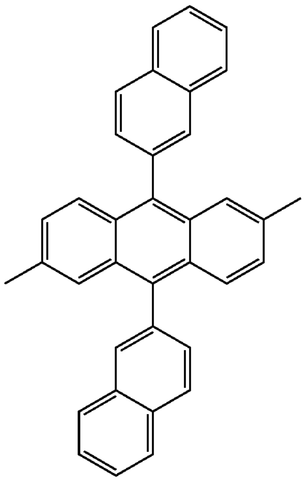 | Direct bond | 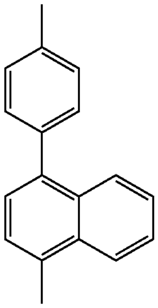 |
| 129 | 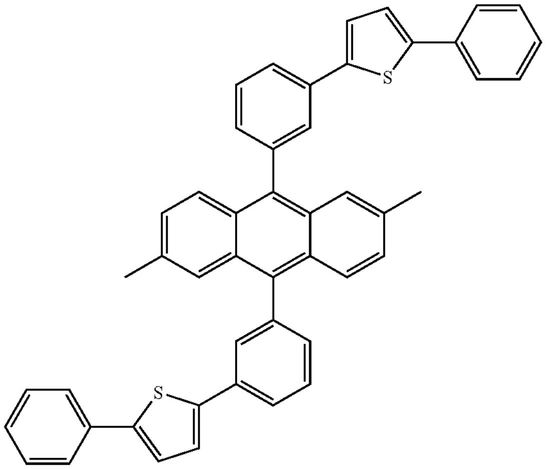 | Direct bond | 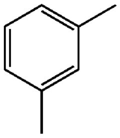 |
| 130 | 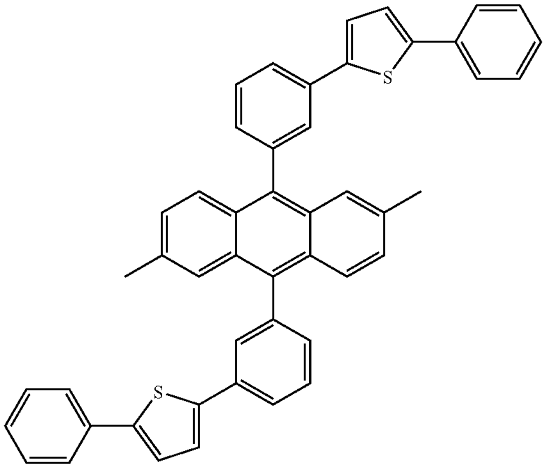 | Direct bond | 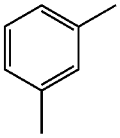 |

TABLE 5-continued
| | | | |
|---|---|---|---|
| 131 | 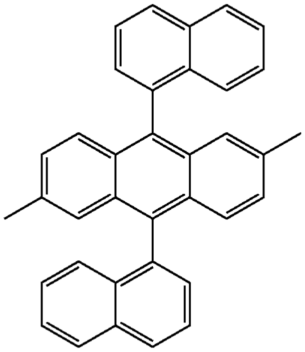 | Direct bond | 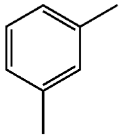 |
| 132 | 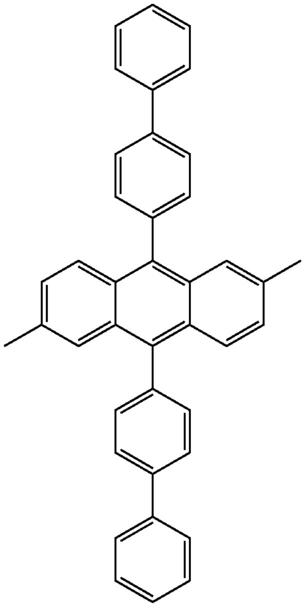 | Direct bond | 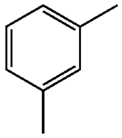 |
| 133 | 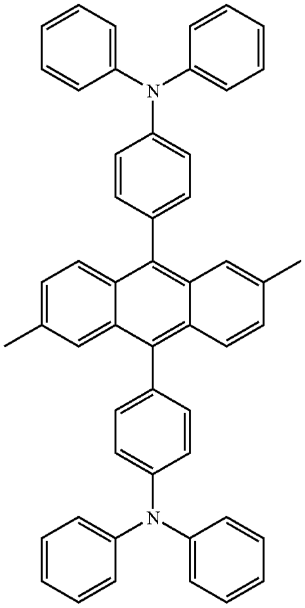 | Direct bond | 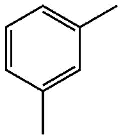 |

TABLE 5-continued
| | | | |
|---|---|---|---|
| 134 | 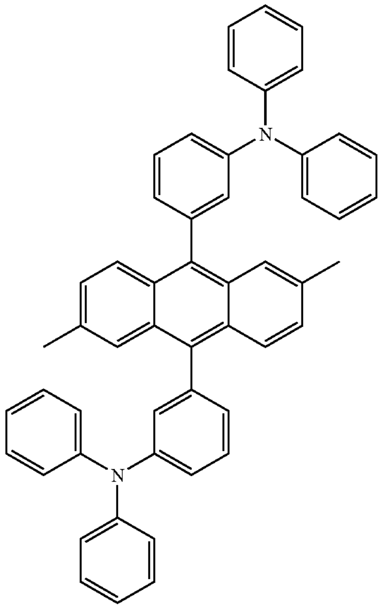 | Direct bond | 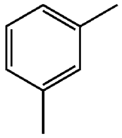 |
| 135 | 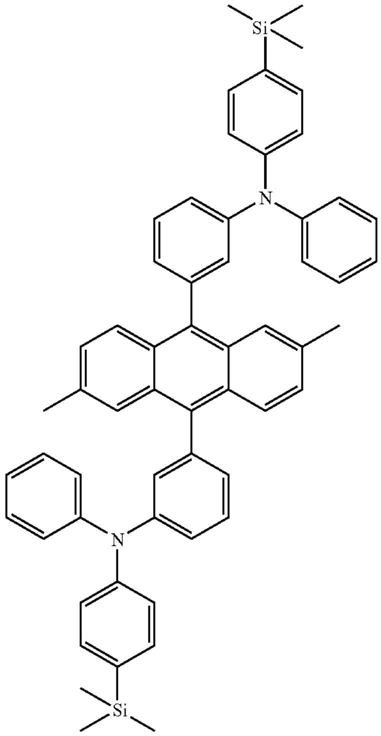 | Direct bond | 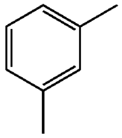 |

TABLE 5-continued
| | | | |
|---|---|---|---|
| 136 | 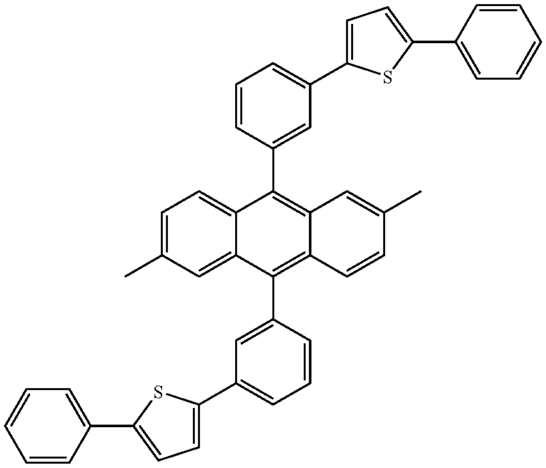 | Direct bond | 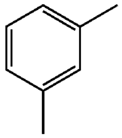 |
| 137 | 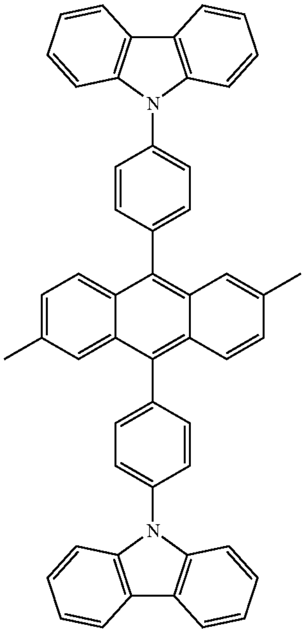 | Direct bond | 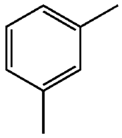 |

TABLE 5-continued
| | | | |
|---|---|---|---|
| 138 | 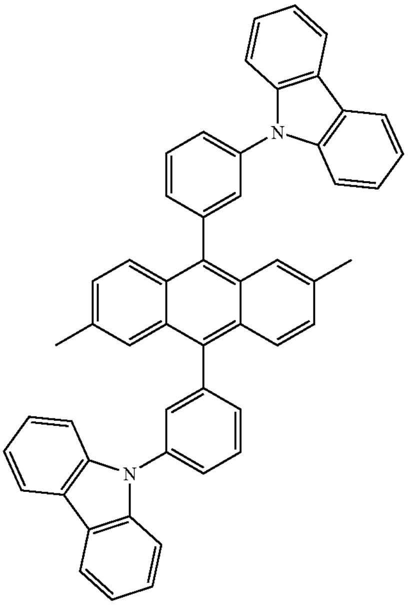 | Direct bond | 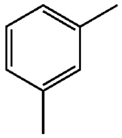 |
| 139 | 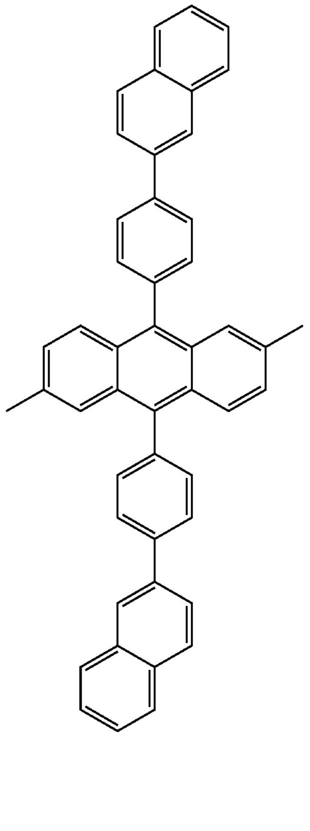 | Direct bond | 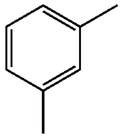 |

TABLE 5-continued
| | | | |
|---|---|---|---|
| 140 | 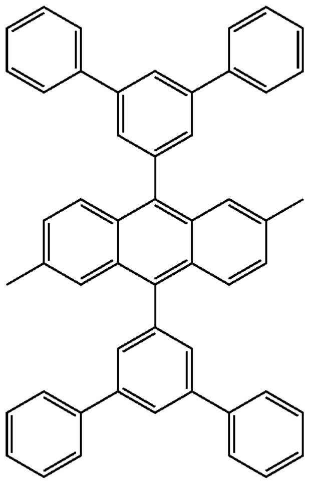 | Direct bond | 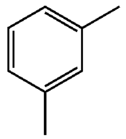 |
| 141 | 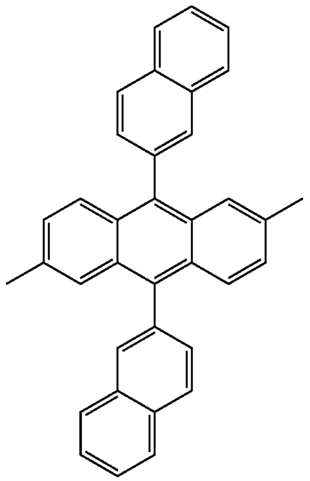 | 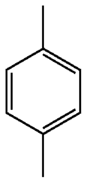 | 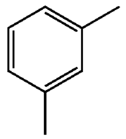 |
| 142 | 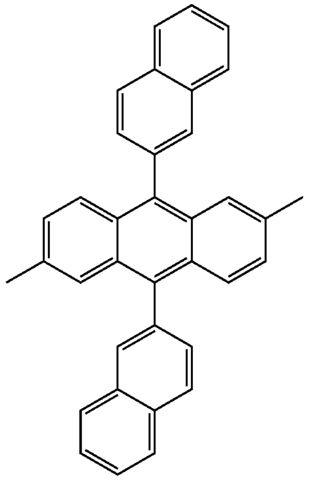 | 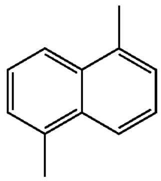 | 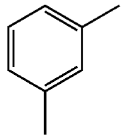 |

TABLE 5-continued
| | | | |
|---|---|---|---|
| 143 | 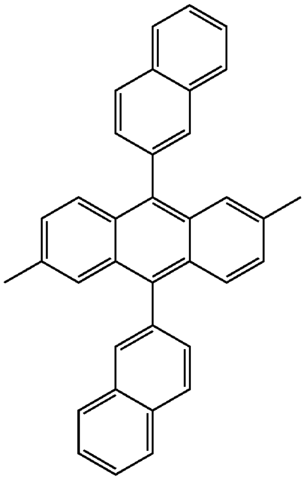 | 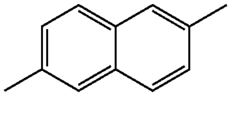 | 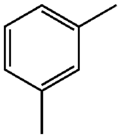 |
| 144 | 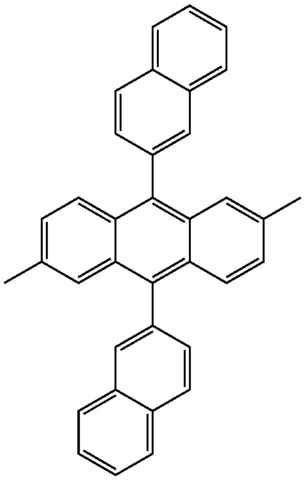 | 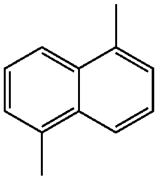 | 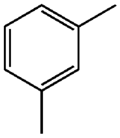 |
| 145 | 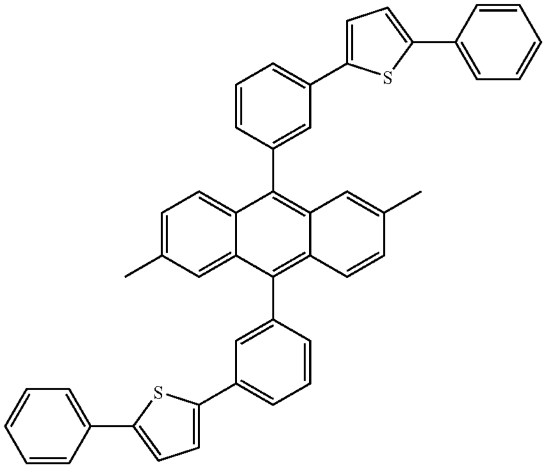 | 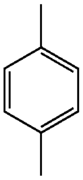 | 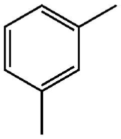 |

TABLE 5-continued
| | | | |
|---|---|---|---|
| 146 | 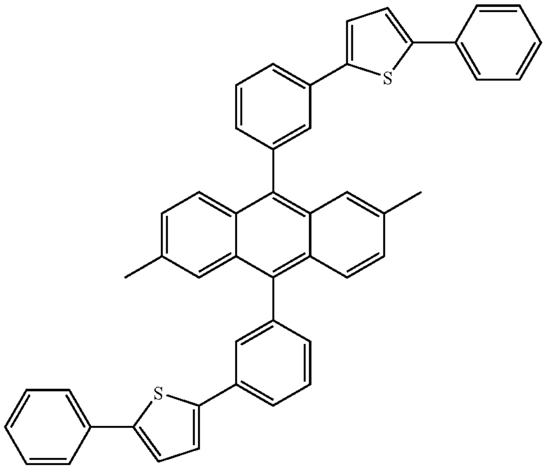 | 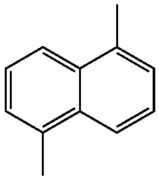 | 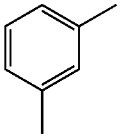 |
| 147 | 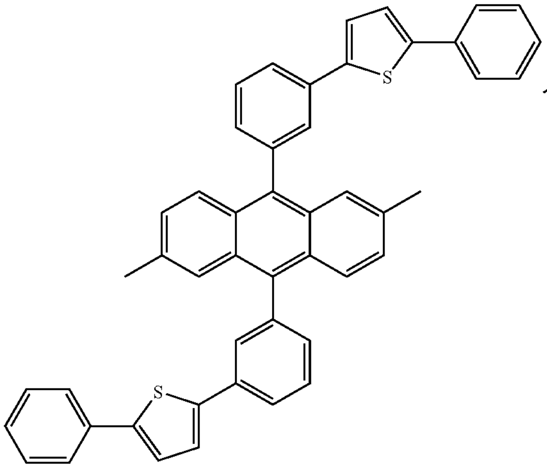 | 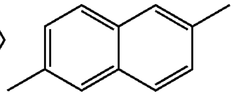 | 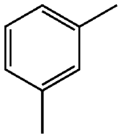 |
| 148 | 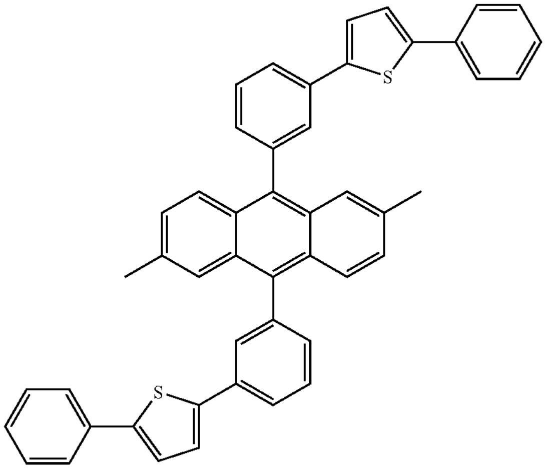 | 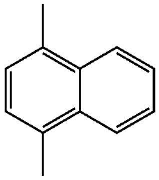 | 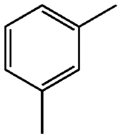 |

TABLE 5-continued
| | | | |
|---|---|---|---|
| 149 | 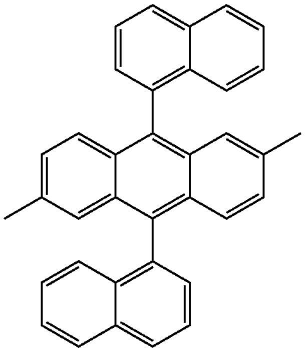 | 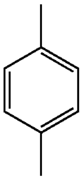 | 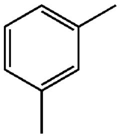 |
| 150 | 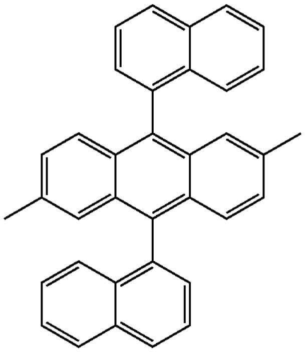 | 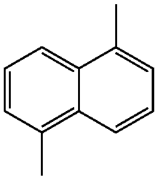 | 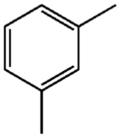 |
| 151 | 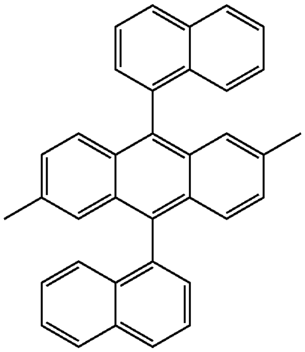 | 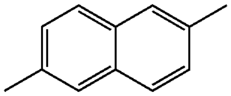 | 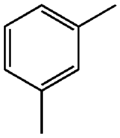 |
| 152 | 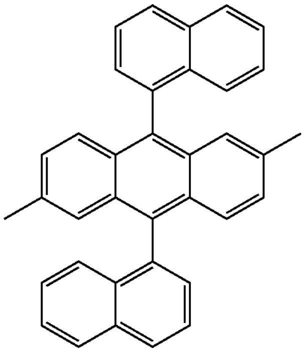 | 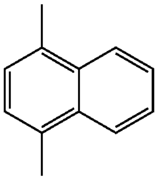 | 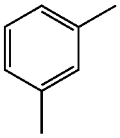 |

TABLE 5-continued
| | | | |
|---|---|---|---|
| 153 | 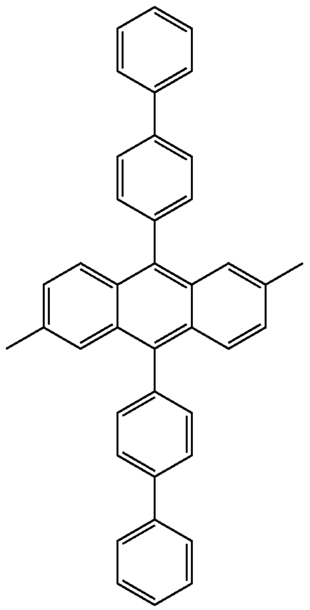 | 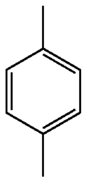 | 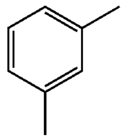 |
| 154 | 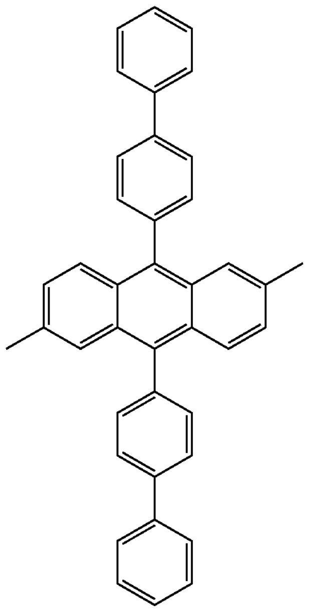 | 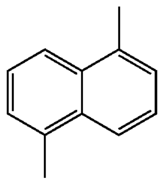 | 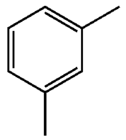 |

TABLE 5-continued
| | | | |
|---|---|---|---|
| 155 | 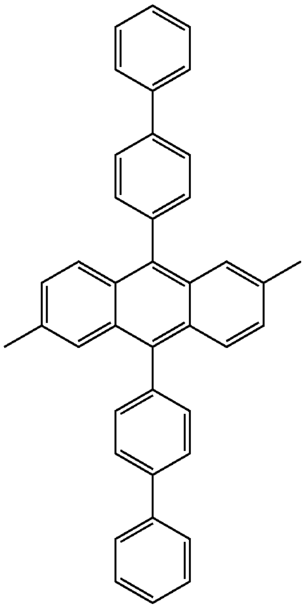 | 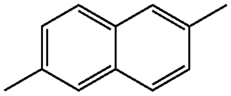 | 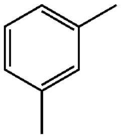 |
| 156 | 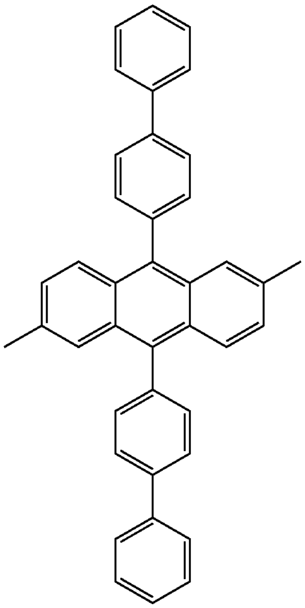 | 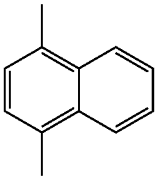 | 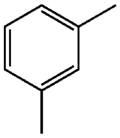 |

TABLE 5-continued
| | | | |
|---|---|---|---|
| 157 | 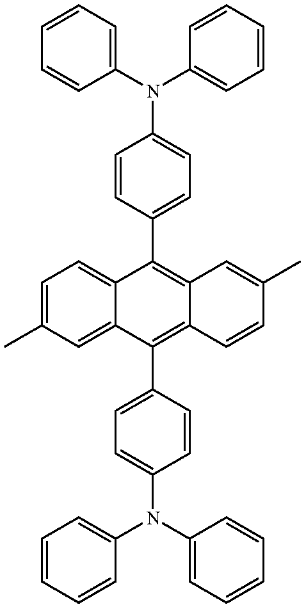 | 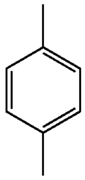 | 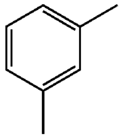 |
| 158 | 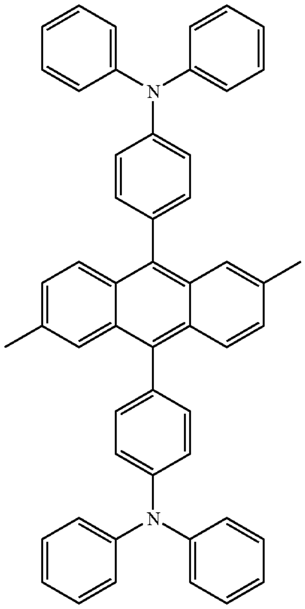 | 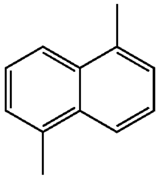 | 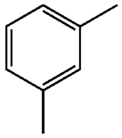 |

TABLE 5-continued
| | | | |
|---|---|---|---|
| 159 | 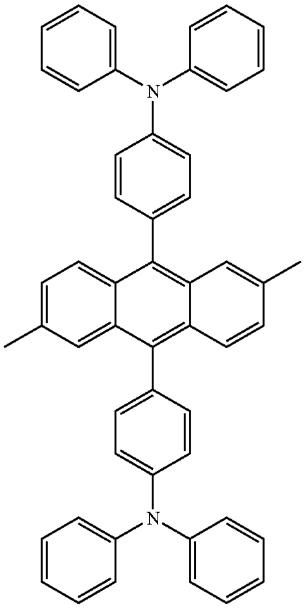 | 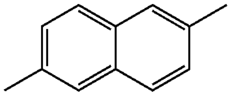 | 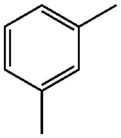 |
| 160 | 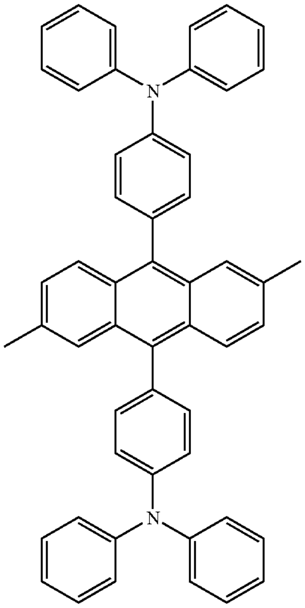 | 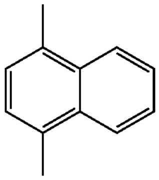 | 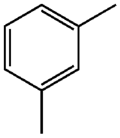 |
| 161 | 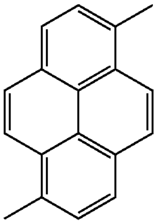 | Direct bond | 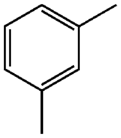 |

TABLE 5-continued
| | | | |
|---|---|---|---|
| 162 | 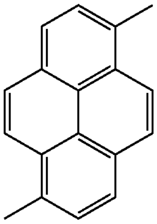 | 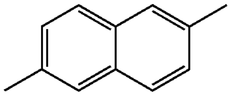 | 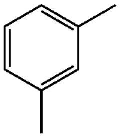 |
| 163 | 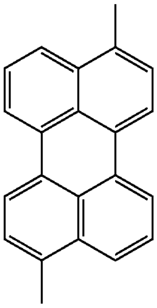 | Direct bond | 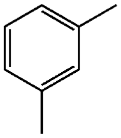 |
| 164 | 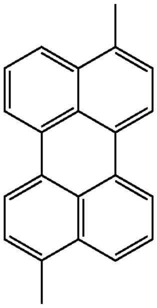 | 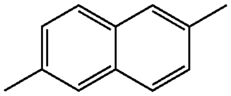 | 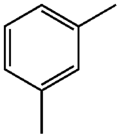 |
| | $R^1$ | $Ar^3$ | Z |
|---|---|---|---|
| 124 | 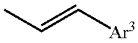 | 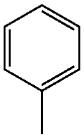 | H |
| 125 | 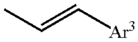 | 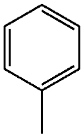 | H |
| 126 | 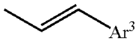 | 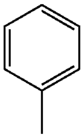 | H |
| 127 | 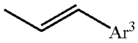 | 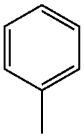 | H |

TABLE 5-continued
| | | | |
|---|---|---|---|
| 128 | 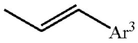 | 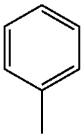 | H |
| 129 | 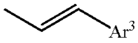 | 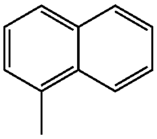 | H |
| 130 | 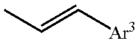 | 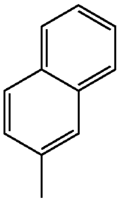 | H |
| 131 | 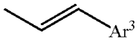 | 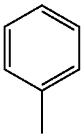 | H |
| 132 | 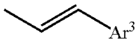 | 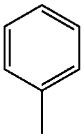 | H |
| 133 | 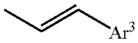 | 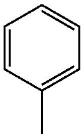 | H |
| 134 | 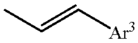 | 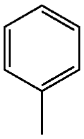 | H |
| 135 | 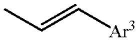 | 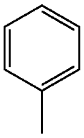 | H |
| 136 | 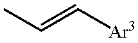 | 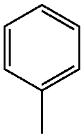 | H |
| 137 | 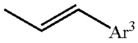 | 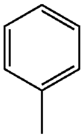 | H |

TABLE 5-continued
| | | | |
|---|---|---|---|
| 138 | 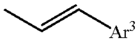 | 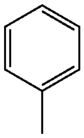 | H |
| 139 | 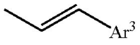 | 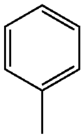 | H |
| 140 | 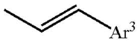 | 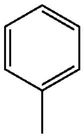 | H |
| 141 | 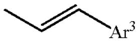 | 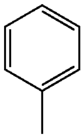 | H |
| 142 | 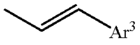 | 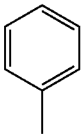 | H |
| 143 | 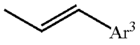 | 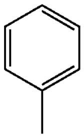 | H |
| 144 | 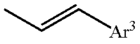 | 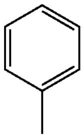 | H |
| 145 | 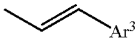 | 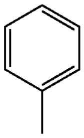 | H |
| 146 | 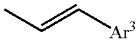 | 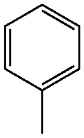 | H |
| 147 | 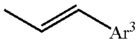 | 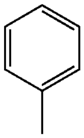 | H |
| 148 | 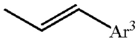 | 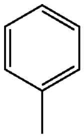 | H |

TABLE 5-continued
| | | | |
|---|---|---|---|
| 149 | 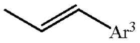 | 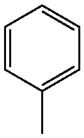 | H |
| 150 | 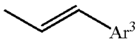 | 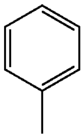 | H |
| 151 | 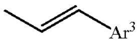 | 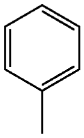 | H |
| 152 | 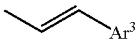 | 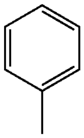 | H |
| 153 | 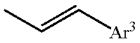 | 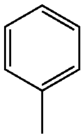 | H |
| 154 | 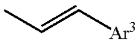 | 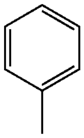 | H |
| 155 | 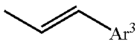 | 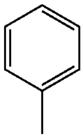 | H |
| 156 | 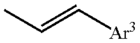 | 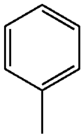 | H |
| 157 | 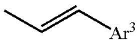 | 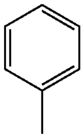 | H |
| 158 | 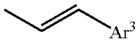 | 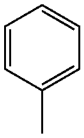 | H |

TABLE 5-continued
| | | | |
|---|---|---|---|
| 159 | 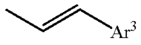 | 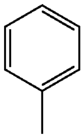 | H |
| 160 | 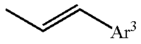 | 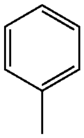 | H |
| 161 | 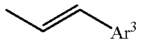 | 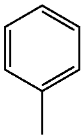 | H |
| 162 | 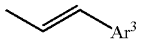 | 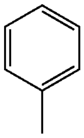 | H |
| 163 | 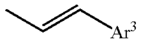 | 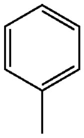 | H |
| 164 | 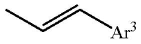 | 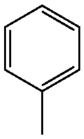 | H |
The following Table 6 presents specific examples of the compound having a symmetric structure, wherein in the formula 2, n+m is equal to 1, and Ar1 has a substituent.

TABLE 6
| | Ar[1] | L |
|---|---|---|
| 165 | 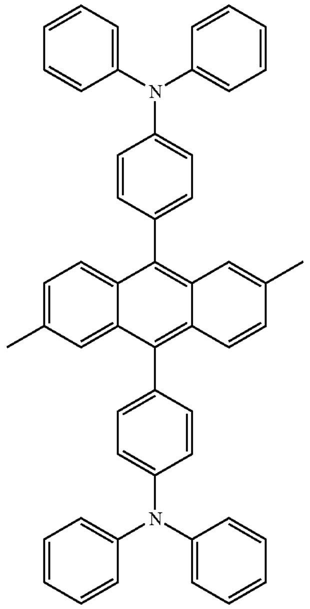 | Direct bond |
| 166 | 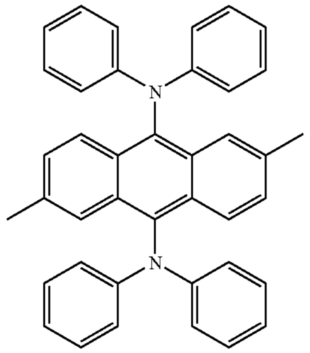 | Direct bond |
| 167 | 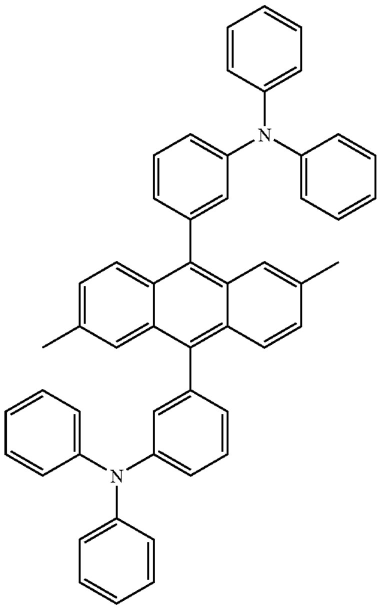 | Direct bond |

TABLE 6-continued
| | | |
|---|---|---|
| 168 | 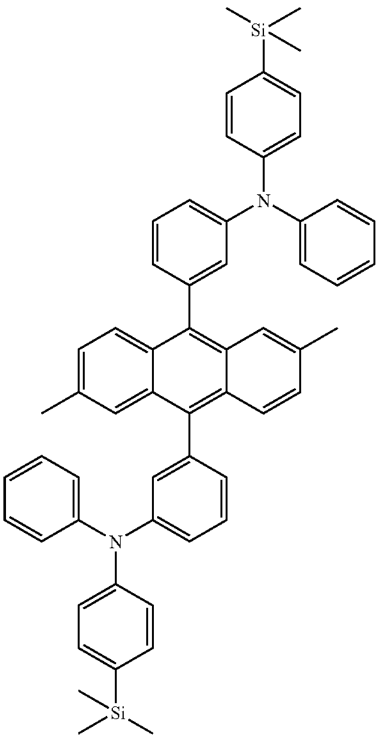 | Direct bond |
| 169 | 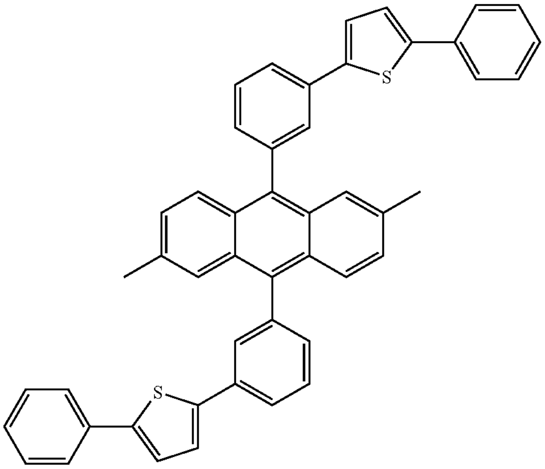 | Direct bond |

TABLE 6-continued
| | | |
|---|---|---|
| 170 | 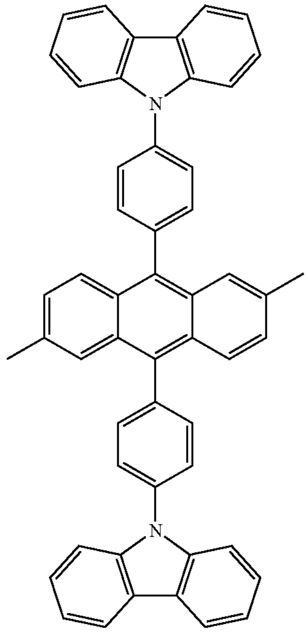 | Direct bond |
| 171 | 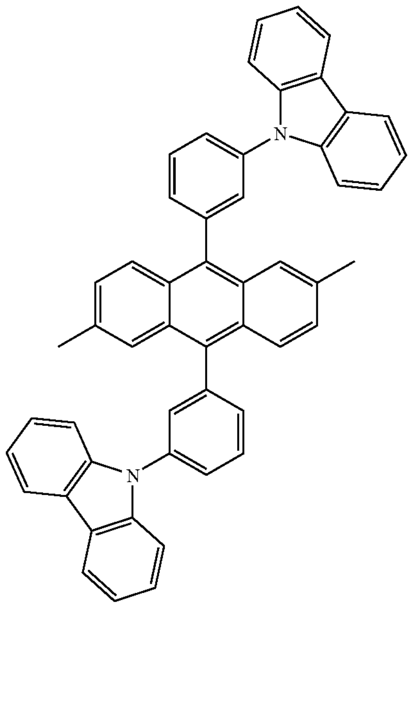 | Direct bond |

TABLE 6-continued
| | | |
|---|---|---|
| 172 | 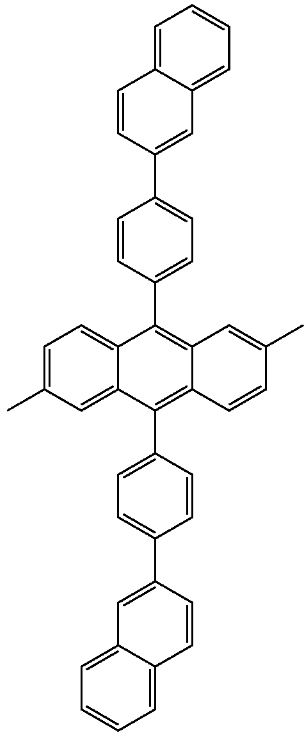 | Direct bond |
| 173 | 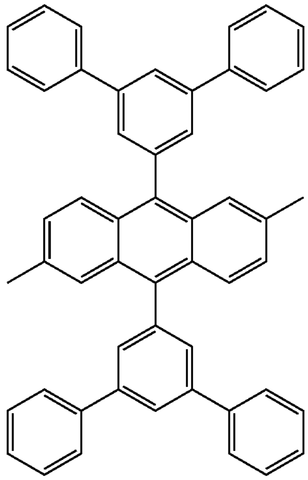 | Direct bond |
| 174 | 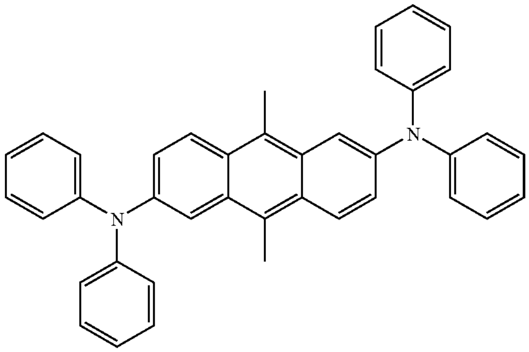 | Direct bond |

TABLE 6-continued
175
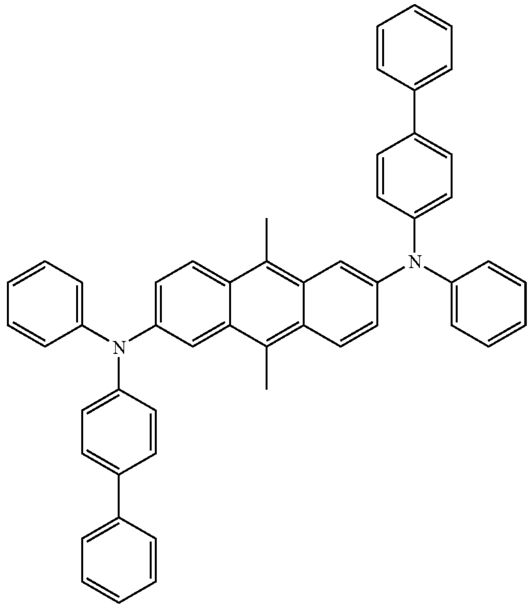
Direct bond
176
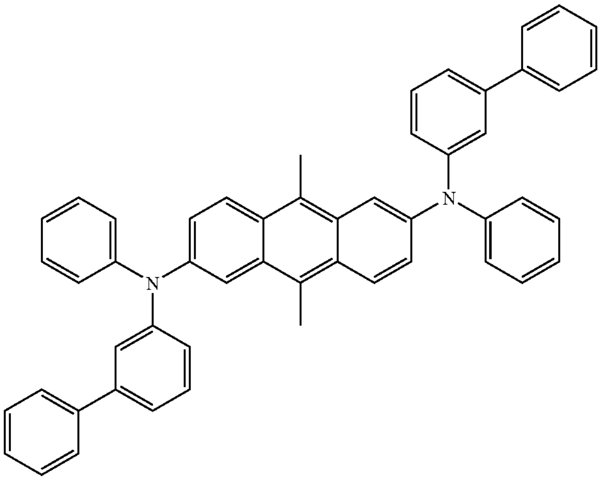
Direct bond
177
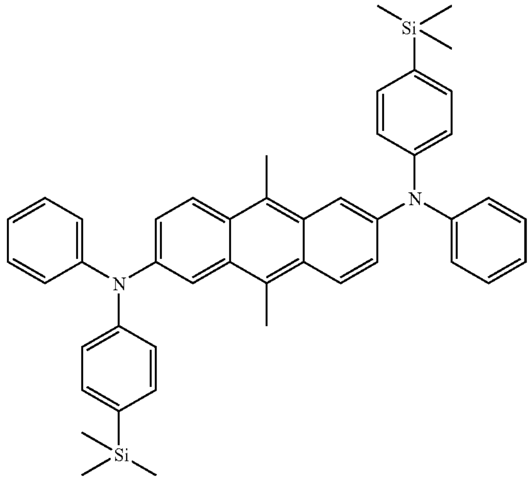
Direct bond TABLE 6-continued
| | | |
|---|---|---|
| 178 | 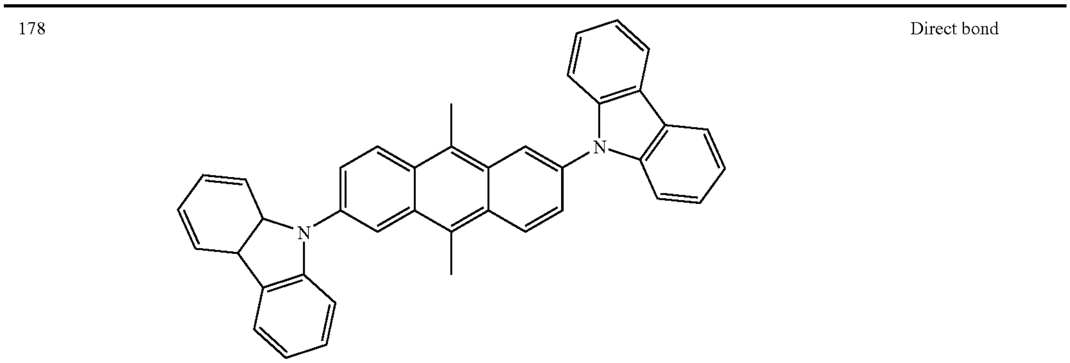 | Direct bond |
| 179 | 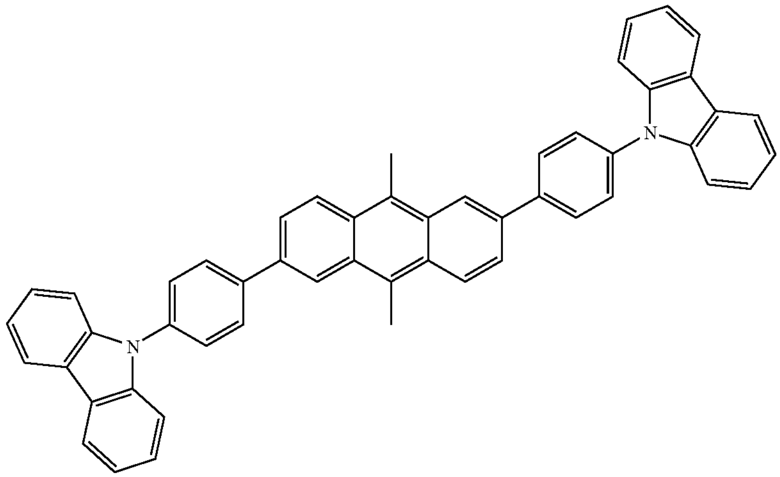 | Direct bond |
| 180 | 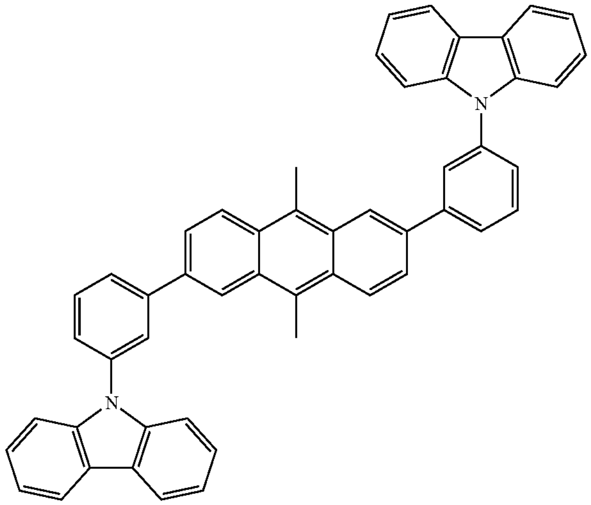 | Direct bond |
| 181 | 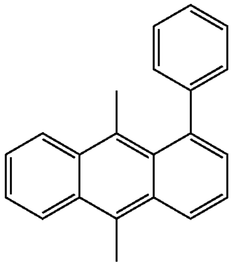 | Direct bond |

TABLE 6-continued
| | | |
|---|---|---|
| 182 | 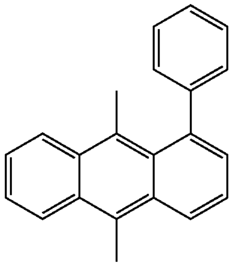 | Direct bond |
| 183 | 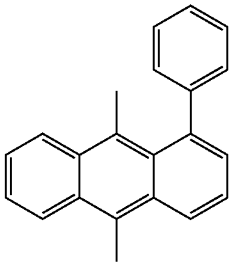 | Direct bond |
| 184 | 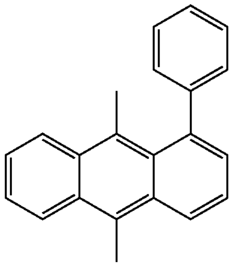 | Direct bond |
| 185 | 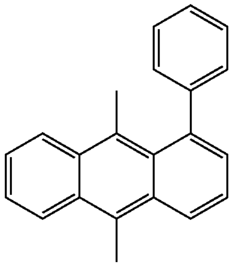 | Direct bond |
| 186 | 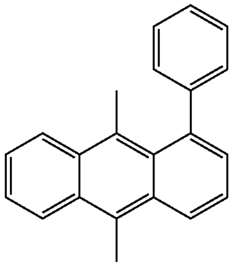 | Direct bond |
| 187 | 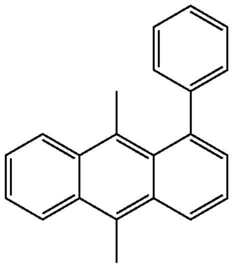 | 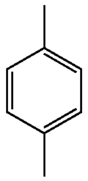 |

TABLE 6-continued
| | | |
|---|---|---|
| 188 | 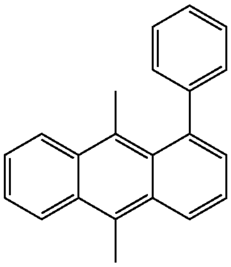 | 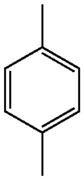 |
| 189 | 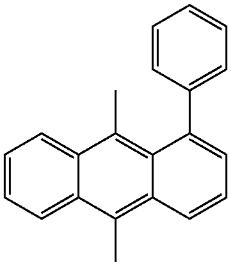 | 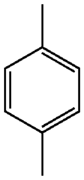 |
| 190 | 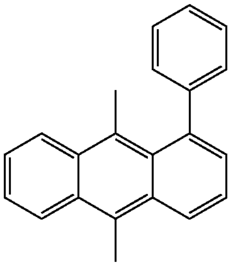 | 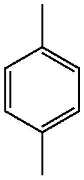 |
| 191 | 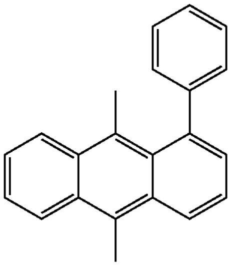 | 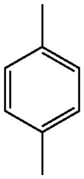 |
| 191 | 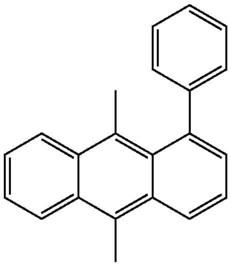 | 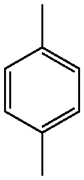 |

TABLE 6-continued
| | | |
|---|---|---|
| 192 | 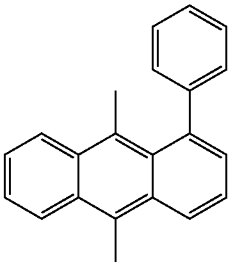 | 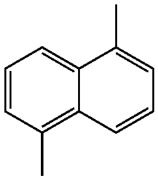 |
| 193 | 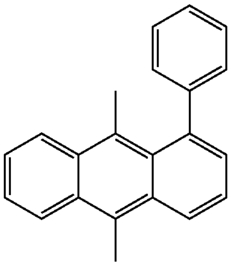 | 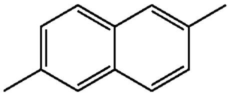 |
| 194 | 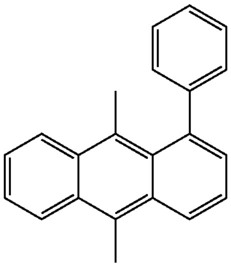 | 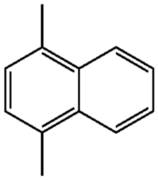 |
| 195 | 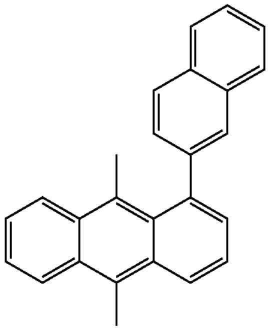 | Direct bond |
| 196 | 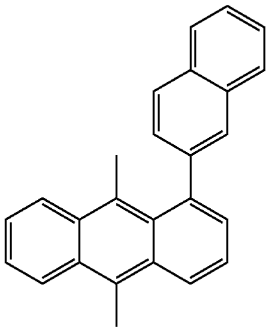 | Direct bond |

TABLE 6-continued
| | | |
|---|---|---|
| 197 | 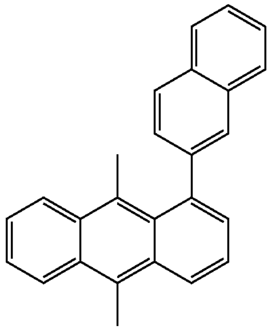 | Direct bond |
| 198 | 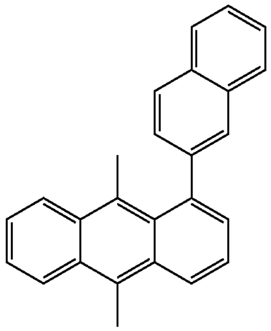 | Direct bond |
| 199 | 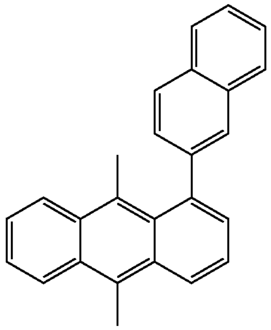 | Direct bond |
| 200 | 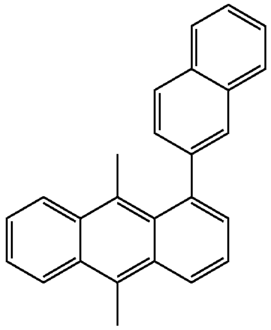 | Direct bond |

TABLE 6-continued
| | | |
|---|---|---|
| 201 | 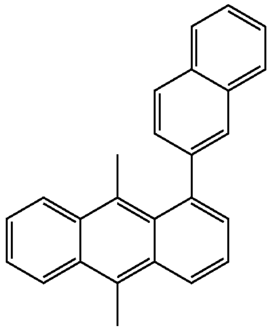 | 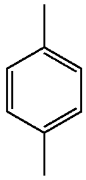 |
| 202 | 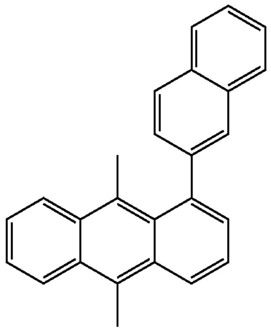 | 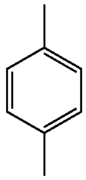 |
| 203 | 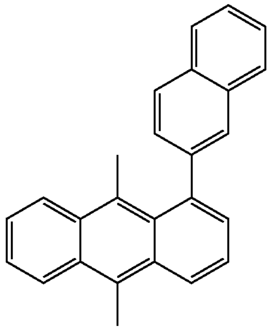 | 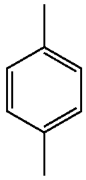 |
| 204 | 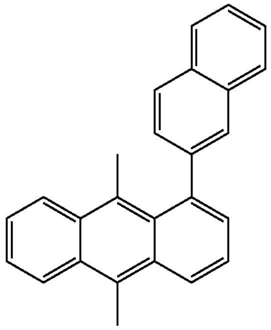 | 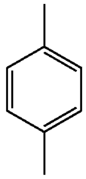 |

TABLE 6-continued
| | | |
|---|---|---|
| 205 | 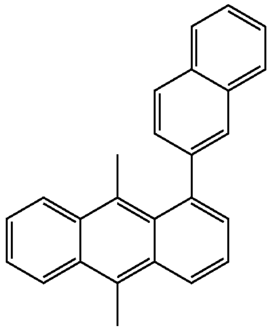 | 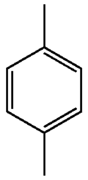 |
| 206 | 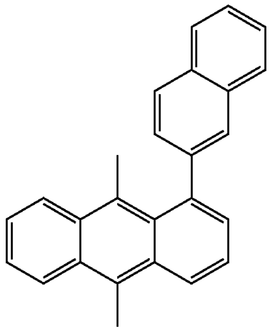 | 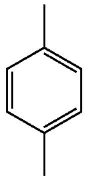 |
| 207 | 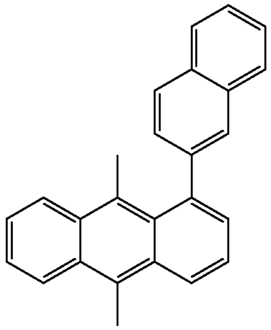 | 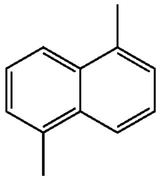 |
| 208 | 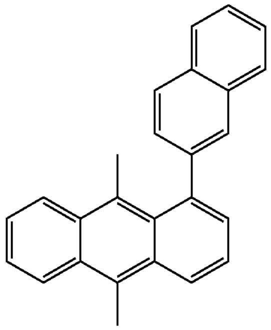 | 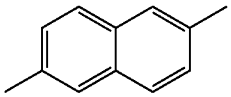 |

TABLE 6-continued
| | | |
|---|---|---|
| 209 | 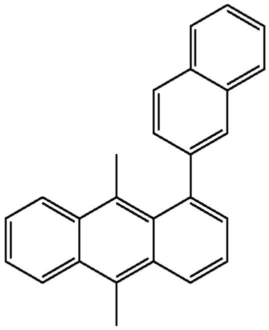 | 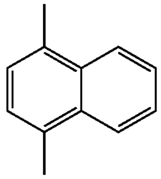 |
| 210 | 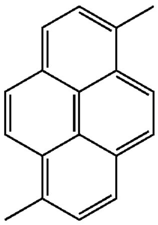 | Direct bond |
| 211 | 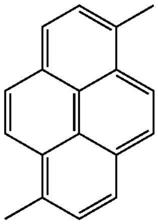 | 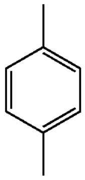 |
| 212 | 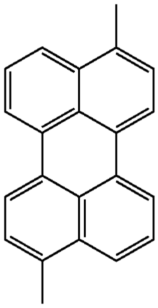 | Direct bond |
| 213 | 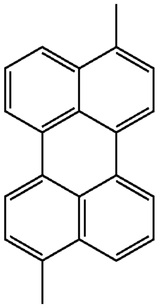 | 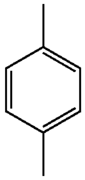 |
| | $Ar^2$ | $R^1$ or $R^2$ | $Ar^3$ |
|---|---|---|---|
| 165 | 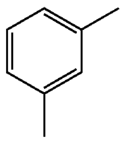 | 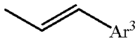 | 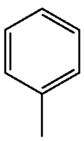 |

TABLE 6-continued
| | | | |
|---|---|---|---|
| 166 | 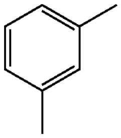 | 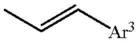 | 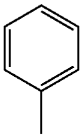 |
| 167 | 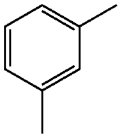 | 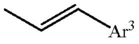 | 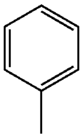 |
| 168 | 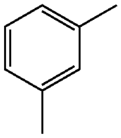 | 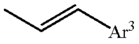 | 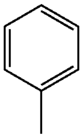 |
| 169 | 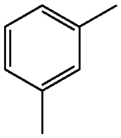 | 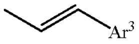 | 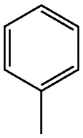 |
| 170 | 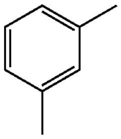 | 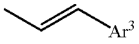 | 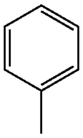 |
| 171 | 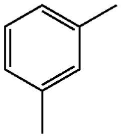 | 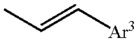 | 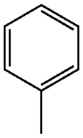 |
| 172 | 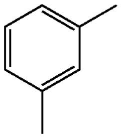 | 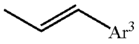 | 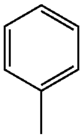 |
| 173 | 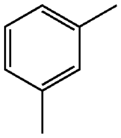 | 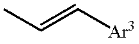 | 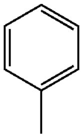 |
| 174 | 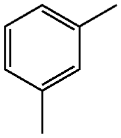 | 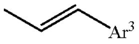 | 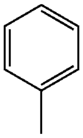 |
| 175 | 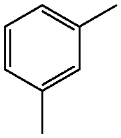 | 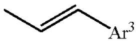 | 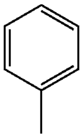 |

TABLE 6-continued
| | | | |
|---|---|---|---|
| 176 | 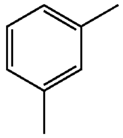 | 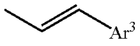 | 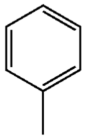 |
| 177 | 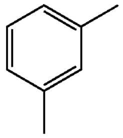 | 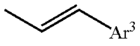 | 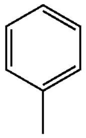 |
| 178 | 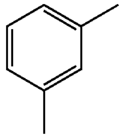 | 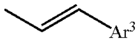 | 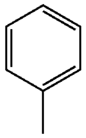 |
| 179 | 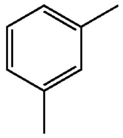 | 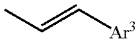 | 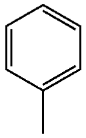 |
| 180 | 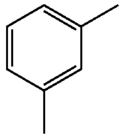 | 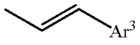 | 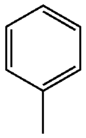 |
| 181 | 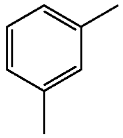 | 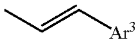 | 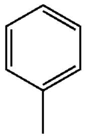 |
| 182 | 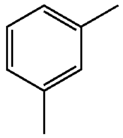 | 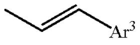 | 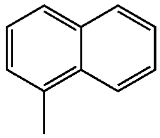 |
| 183 | 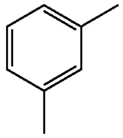 | 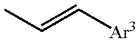 | 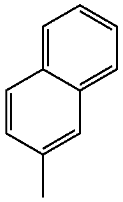 |
| 184 | 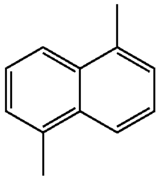 | 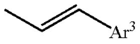 | 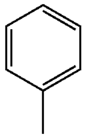 |
| 185 | 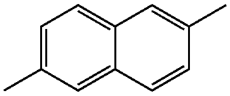 | 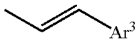 | 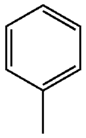 |

TABLE 6-continued
| | | | |
|---|---|---|---|
| 186 | 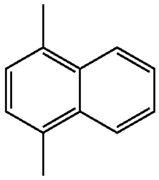 | 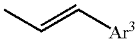 | 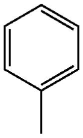 |
| 187 | 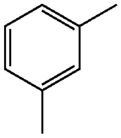 | 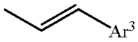 | 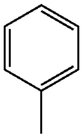 |
| 188 | 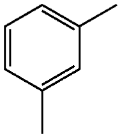 | 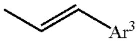 | 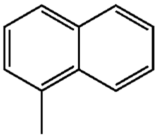 |
| 189 | 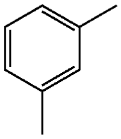 | 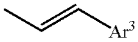 | 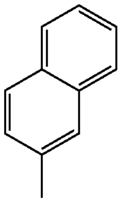 |
| 190 | 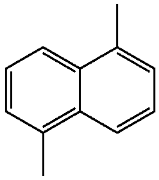 | 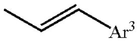 | 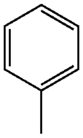 |
| 191 | 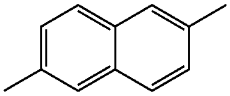 | 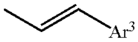 | 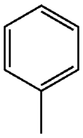 |
| 191 | 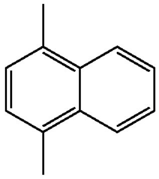 | 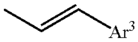 | 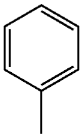 |
| 192 | 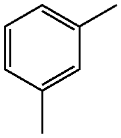 | 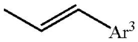 | 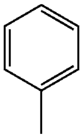 |
| 193 | 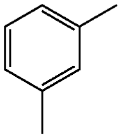 | 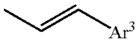 | 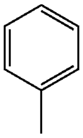 |

TABLE 6-continued
| | | | |
|---|---|---|---|
| 194 | 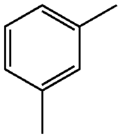 | 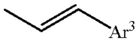 | 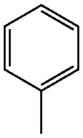 |
| 195 | 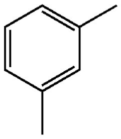 | 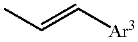 | 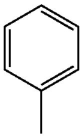 |
| 196 | 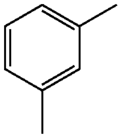 | 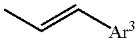 | 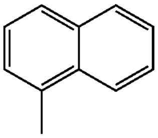 |
| 197 | 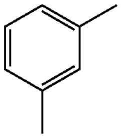 | 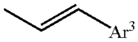 | 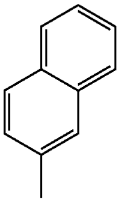 |
| 198 | 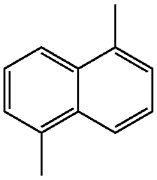 | 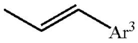 | 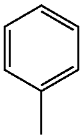 |
| 199 | 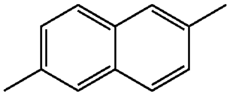 | 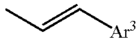 | 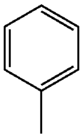 |
| 200 | 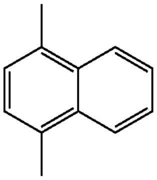 | 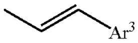 | 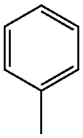 |
| 201 | 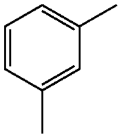 | 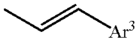 | 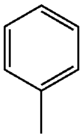 |
| 202 | 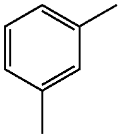 | 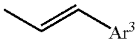 | 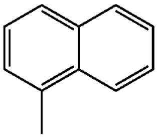 |

TABLE 6-continued
| | | | |
|---|---|---|---|
| 203 | 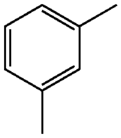 | 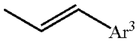 | 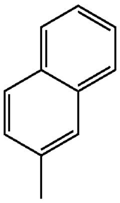 |
| 204 | 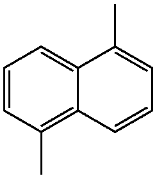 | 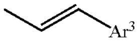 | 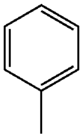 |
| 205 | 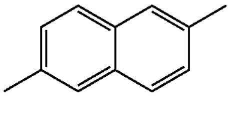 | 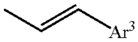 | 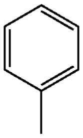 |
| 206 | 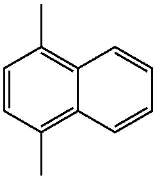 | 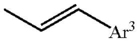 | 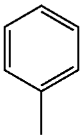 |
| 207 | 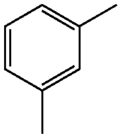 | 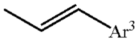 | 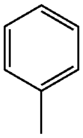 |
| 208 | 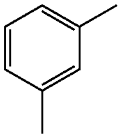 | 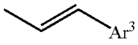 | 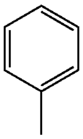 |
| 209 | 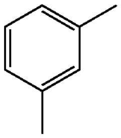 | 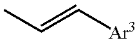 | 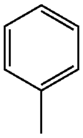 |
| 210 | 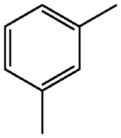 | 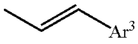 | 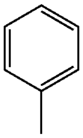 |
| 211 | 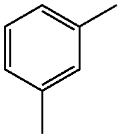 | 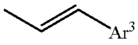 | 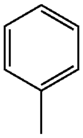 |
| 212 | 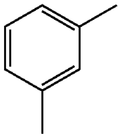 | 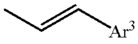 | 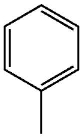 |

TABLE 6-continued

| | |
|---|---|
| 213 | 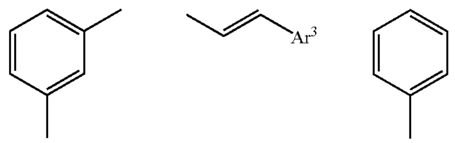 |

The compounds of the formula 1 according to the present invention have such the characteristic structures that at least two fluorophores, that is, the substituted Ar1 and the substituted Ar2 are twisted at a large angle from each other, relative to L, and thus the conjugations are not connected or weakened. Further, if the light emitting wavelength gets too long, there is caused a problem that the energy transfer from a host material to a dopant material gets harder. However, for the compounds of the formula 1 according to the present invention, double bonds or triple bonds are at the positions where the light emitting wavelengths are not made longer, that is, ortho or meta positions rather than para positions. Further, particularly, introduction of a monomerized styryl group, not of a dimerized styryl group gives structural flexibility of the styryl group, which can improve the stability of the film. By these characteristics, the formation of a layer which is contact with hole transporting layer or an electron transporting layer improves the interfacial characteristics, and thus gives a structure playing an advantageous role in the life time of the device. Accordingly, if the compound of the formula 1 with a structure having a suitable energy level is used as a light emitting material such as a host and a dopant in an organic light emitting diode, the energy transfer from the host to the dopant can be efficiently performed, thus greatly improving the efficiency of the device.

Specifically, by an example of the structures of the compounds 1 of the formula 1 (see Table 1), the (2,5-styrenyl)-1-phenyl part and the 9-(2-naphthyl)anthracene part are twisted from each other at about 90 degrees, and they are chemically bonded to each other, but do not give great effect on the conjugation from each other, which can show light emitting spectrum at wavelength bands, which are each independently similar or the same to each other. That is, Ar1, for example, a substituent which is bonded to anthracene is characterized in that it not only gives an effect simply on the thermal stability and the film morphology, but also indirectly or directly on the energy transfer with an anthracene core to a dopant. Accordingly, the present invention is intended to use such the structure of the compound in an organic light emitting diode, thereby improving the efficiency and the life time of the device.

Further, the compound of the formula 1 according to the present invention can be prepared by subjecting an alkenyl group- or an alkynyl group-substituted bromobenzene, or an alkenyl group- or an alkynyl group-substituted iodobenzene, and anthracene boronic acid, as starting materials, to an aryl-aryl Suzuki coupling method for introduction of a substituent, in the presence of a palladium [II] catalyst and a base (for example, inorganic bases such as potassium acetate). Specific methods for preparing the compound of the formula 1 according to the present invention are illustrated in Examples.

Further, the present invention provides an organic light emitting diode comprising a first electrode, a second electrode, and at least one organic material layer disposed between the first electrode and the second electrode, wherein at least one layer of the organic material layer(s) comprises the compound of the formula 1.

The above-described compounds of the present invention can not only serve as a light emitting material alone, but also serve as a light emitting host in combination with a proper light emitting dopant, or a light emitting dopant in combination with a proper light emitting host, particularly in an organic light emitting diode.

The organic light emitting diode of the present invention can be prepared by using common methods and materials for preparing an organic light emitting diode as will be described later, except that the above-described compound according to the present invention is used to form an organic material layer, in particular, light emitting layer, of an organic light emitting diode.

According to one embodiment of the present invention, the organic light emitting diode can be configured to comprise a first electrode, a second electrode, and organic material layer(s) disposed therebetween, and the organic light emitting diode can be prepared by using common methods and materials for preparing an organic light emitting diode, except that the above-described compound according to the present invention is used in at least one layer of the organic material layer(s) of the organic light emitting diode. The structure of the organic light emitting diode according to the present invention is illustrated in FIG. 1.

For example, the organic light emitting diode according to the present invention can be prepared by depositing a metal, or a metal oxide having conductivity on a substrate using a PVD (physical vapor deposition) process such as sputtering and e-beam evaporation to form an anode; forming organic material layer(s) comprising a hole injecting layer, a hole transporting layer, a light emitting layer and an electron transporting layer on the anode; and depositing a material, which can be used as a cathode, thereon. Alternatively, an organic light emitting diode can be prepared by depositing a cathode material, an organic material layer, and an anode material in this order on a substrate (see PCT Patent Application Publication WO 2003/012890).

The organic material layer may be of a multilayer structure containing a hole injecting layer, a hole transporting layer, a light emitting layer, an electron transporting layer, and the like, but are not limited thereto, and may be of a monolayer structure. Further, the organic material layer can be produced to have a fewer number of layers, by using a variety of polymeric materials, by means of a solvent process other than a deposit process, such as spin coating, dip coating, doctor blading, screen printing, ink jet printing, and heat transfer process.

The anode material is preferably a material having a large work function to facilitate hole injection usually to an organic material layer. Specific examples of the anode material which can be used in the present invention include metals such as vanadium, chromium, copper, zinc and gold, or an alloy thereof; metal oxides such as zinc oxide, indium oxide, indium-tin oxide (ITO), and indium zinc oxide (IZO); a combination of a metal and an oxide such as ZnO:Al and SnO2: Sb; conductive polymers such as poly(3-methylthiophene), poly[3,4-(ethylene-1,2-dioxy)thiophene] (PEDT), polypyrrole and polyaniline, but are not limited thereto.

The cathode material is preferably a material having a small work function to facilitate electron injection usually to an organic material layer. Specific examples of the cathode material include metals such as magnesium, calcium, sodium, potassium, titanium, indium, yttrium, lithium, gadolinium, aluminum, silver, tin and lead, or an alloy thereof; multilayer structure materials such as LiF/Al and LiO2/Al, but are not limited thereto.

The hole injecting material is a material facilitating hole injection from an anode at low voltage. The HOMO (highest occupied molecular orbital) level of the hole injecting material is preferably located between the work function of the anode materials and the HOMO level of its neighboring organic material layer. Specific examples of the hole injecting material include organic materials of metal porphyrin, oligothiophene and arylamine series, organic materials of hexanitrile hexaazatriphenylene and quinacridone series, organic materials of perylene series, and conductive polymers of anthraquinone, polyaniline, and polythiophene series, but are not limited thereto.

The hole transporting material is a material having high hole mobility, which can transfer holes from the anode or the hole injecting layer toward the light emitting layer. Specific examples thereof include organic materials of arylamine series, conductive polymers and block copolymers having both conjugated portions and non-conjugated portions, but are not limited thereto.

The light emitting material are a material capable of emitting visible light by accepting and recombining holes from the hole transporting layer and electrons from the electron transporting layer, preferably a material having high quantum efficiency for fluorescence and phosphorescence. Specific examples thereof include 8-hydroxyquinoline aluminum complex (Alq3); compounds of carbazole series; dimerized styryl compounds; BAlq; 10-hydroxybenzoquinoline-metal compounds; compounds of benzoxazole, benzthiazole and benzimidazole series; polymers of poly(p-phenylenevinylene) (PPV) series; spiro compounds; and compounds of polyfluorene and rubrene series, but are not limited thereto.

The electron transporting material is suitably a material having high electron mobility, which can transfer electrons from the cathode to the light emitting layer. Specific examples thereof include 8-hydroxyquinoline aluminum complex ($Alq_3$); complexes including $Alq_3$; organic radical compounds; and hydroxyflavone-metal complexes, but are not limited thereto.

The organic light emitting diode according to the invention may be of a front-side, back-side or double-sided light emission according to the materials used.

The compound according to the invention can function in an organic electronic device including an organic solar cell, an organic photoconductor and an organic transistor, according to a principle similar to that applied to the organic light emitting diode.

MODE FOR INVENTION

Hereinafter, the present invention will be described in more detail by means of Examples and Experimental Examples, but the scope of the invention is not limited thereto.

Example 1

Synthesis of Compound 1

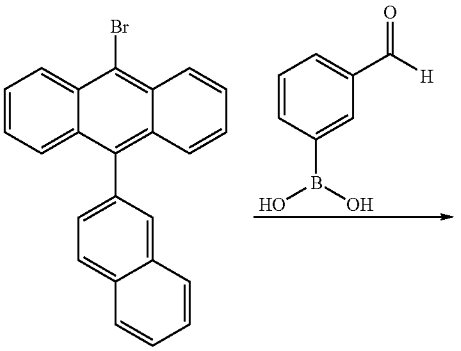

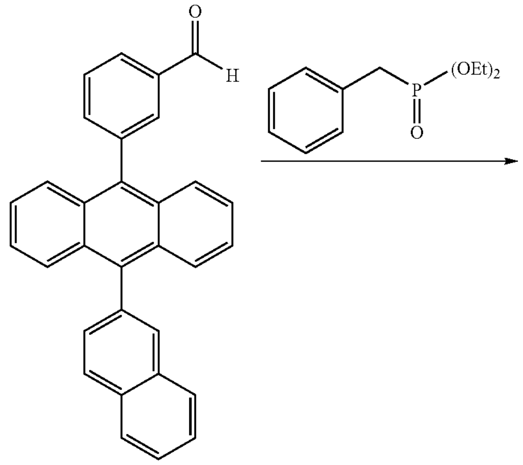

1a

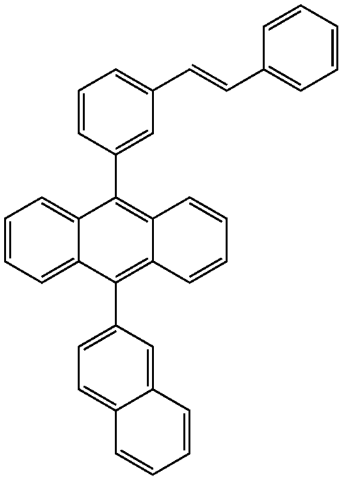

1

1-A. Synthesis of Compound 1a

To a solution obtained by dissolving 9-bromo-10-(2-naphthyl)anthracene (18 g, 46.1 mmol) in THF (150 mL), a solution obtained by dissolving 3-formyl benzene boronic acid (8.4 g, 56.2 mmol) in EtOH (50 mL) was added, under $N_2$. To the mixture, a solution obtained by dissolving $K_2CO_3$ (26 g, 187.6 mmol) in $H_2O$ (100 mL) and added, finally $Pd(PPh_3)_4$ (1.1 g, 0.9 mmol) were added, and the mixture was stirred under reflux for about 17 hours. After completion of reaction, the mixture was cooled to ambient temperature, and the organic phase was separated from the mixed reaction solution, and filtered to obtain a solid. This solid was dissolved in THF again, and purified by column chromatography. Then, the residue was recrystallized from THF and ethanol to obtain a compound 1a (18.6 g, 97%): MS [M]=408

1-B. Synthesis of Compound 1

Benzylphosphoric acid diethyl ether (1.2 mL, 5.8 mmol), sodium hydride (0.29 g, 7.2 mmol), 18-crown-6 (0.1 g, 0.48 mmol) were added to THF (100 mL), and the compound 1a (2 g, 4.8 mmol) as prepared in the process of 1-A was added to the mixture at 0° C., under $N_2$. The mixture was stirred at room temperature for about 12 hours. After completion of the reaction, THF and $H_2O$ were added to the mixed reaction solution. The organic phase was separated, dried over $MgSO_4$, and then concentrated. The residue was recrystallized from THF/EtOH to obtain a compound 1 (1.5 g, 65%). MS [M+H]=483

Example 2

Synthesis of Compound 2

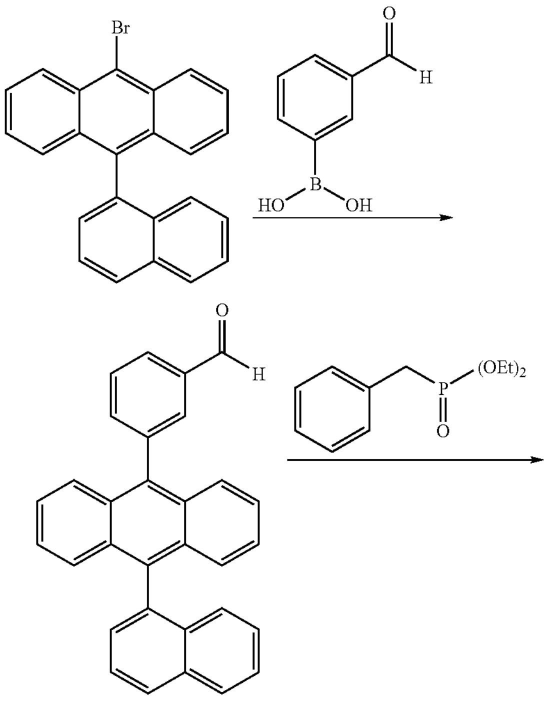

2a

-continued

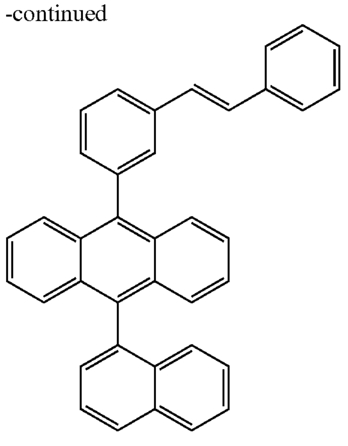

2

2-A. Synthesis of Compound 2a

To a solution obtained by dissolving 9-bromo-10-(1-naphthyl)anthracene (5 g, 13 mmol) in THF (70 mL), a solution obtained by dissolving 3-formyl benzene boronic acid (2.3 g, 15.6 mmol) in EtOH (40 mL) was added, under $N_2$. To the mixture, a solution obtained by dissolving $K_2CO_3$ (7 g, 52 mmol) in $H_2O$ (25 mL), and finally $Pd(PPh_3)_4$ (0.23 g, 0.3 mmol) were added, and the mixture was stirred under reflux for about 17 hours. After completion of reaction, the mixture was cooled to ambient temperature, and the organic phase was separated from the mixed reaction solution, and filtered to obtain a solid. This solid was dissolved in THF again, and purified by column chromatography. Then, the residue was recrystallized from THF and ethanol to obtain a compound 2a (2.9 g, 55%). MS [M]=408

2-B. Synthesis of Compound 2

Benzylphosphoric acid diethyl ether (1.2 mL, 5.8 mmol), sodium hydride (0.29 g, 7.2 mmol), 18-crown-6 (0.1 g, 0.48 mmol) were added to THF (100 mL), and the compound 2a (2 g, 4.8 mmol) as prepared in the process of 2-A was added to the mixture at 0° C., under $N_2$. The mixture was stirred at room temperature for about 12 hours. After completion of the reaction, THF and $H_2O$ were added to the mixed reaction solution. The organic phase was separated, dried over $MgSO_4$, and then concentrated. The residue was recrystallized from THF/EtOH to obtain a compound 2 (2.2 g, 96%). MS [M+H]=483

Example 3

Synthesis of Compound 3

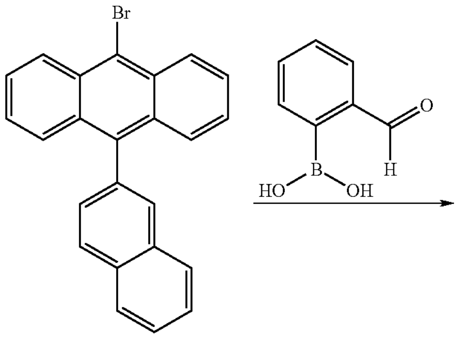

-continued

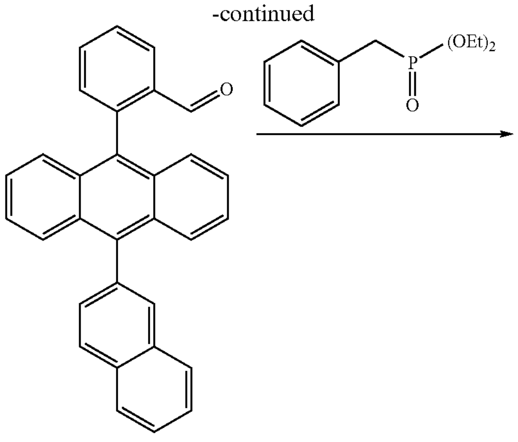

3a

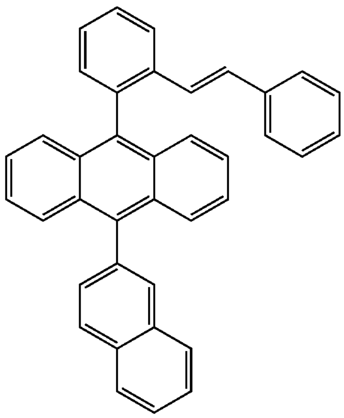

3

3-A. Synthesis of Compound 3a

To a solution obtained by dissolving 9-bromo-10-(2-naphthyl)anthracene (5 g, 13 mmol) in THF (70 mL), a solution obtained by dissolving 2-formyl benzene boronic acid (2.3 g, 15.6 mmol) in EtOH (40 mL) was added, under $N_2$. To the mixture, a solution obtained by dissolving $K_2CO_3$ (7 g, 52 mmol) in $H_2O$ (25 mL), and finally $Pd(PPh_3)_4$ (0.23 g, 0.3 mmol) were added, and the mixture was stirred under reflux for about 17 hours. After completion of reaction, the mixture was cooled to ambient temperature, and the organic phase was separated from the mixed reaction solution, and filtered to obtain a solid. This solid was dissolved in THF again, and purified by column chromatography. Then, the residue was recrystallized from THF and ethanol to obtain a compound 3a (2.9 g, 55%). MS [M]=408

3-B. Synthesis of Compound 3

Benzylphosphoric acid diethyl ether (1.2 mL, 5.8 mmol), sodium hydride (0.29 g, 7.2 mmol), 18-crown-6 (0.1 g, 0.48 mmol) were added to THF (100 mL), and the compound 3a (2 g, 4.8 mmol) as prepared in the process of 3-A was added to the mixture at 0° C., under $N_2$. The mixture was stirred at room temperature for about 12 hours. After completion of the reaction, THF and $H_2O$ were added to the mixed reaction solution. The organic phase was separated, dried over $MgSO_4$, and then concentrated. The residue was recrystallized from THF/EtOH to obtain a compound 3 (2.2 g, 96%). MS [M+H]=483

Example 4

Synthesis of Compound 5

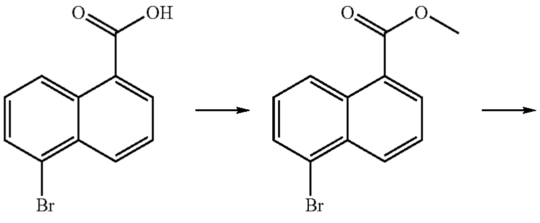

4a

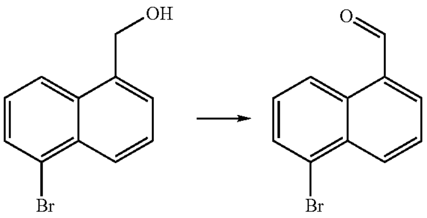

4b

4c

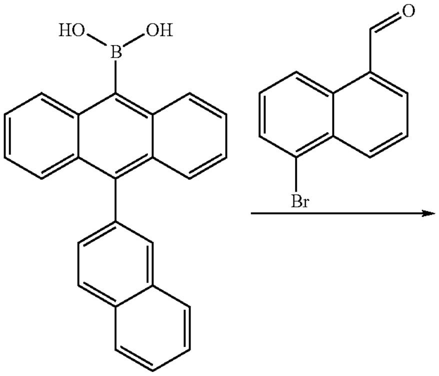

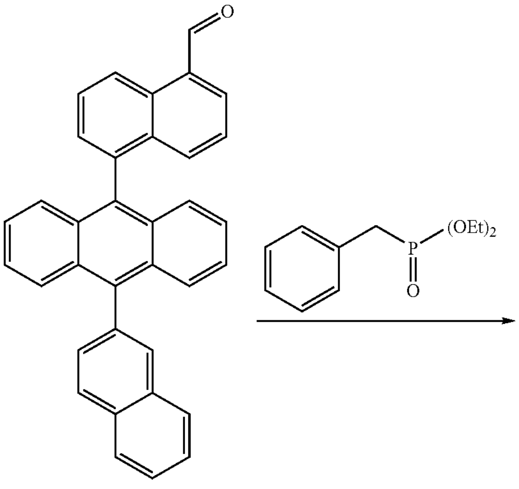

4d

-continued

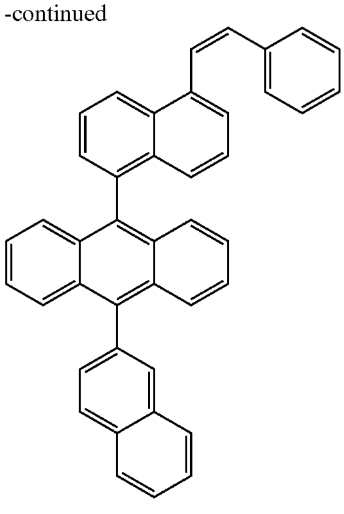

5

4-A. Synthesis of Compound 4a

To a mixture obtained by adding 6-bromo-2-naphthoic acid (3 g, 11.95 mmol), iodomethane (MeI, 1.11 mL), and $K_2CO_3$ (6.58 g, 47.61 mmol), 30 mL of DMF was added, and the mixture was stirred at ambient temperature for 5 hours. After observation of completion of the reaction by means of TLC, the reaction solution was filtered to remove $K_2CO_3$. About 20 mL of DMF was removed from the filtrate under reduced pressure, and water was poured to the residue to precipitate a solid. The obtained solid was filtered, and then the residue washed with ethanol, and dried to obtain a compound 4a (3.06 g, yield 97%). MS $[M+H]^+$=264

4-B. Synthesis of Compound 4b

A mixture obtained by adding LAH (Lithium aluminum hydride 0.86 g, 22.7 mmol) and anhydrous 10 mL of THF was cooled to a temperature of 0° C. The compound 4a (2.3 g, 8.67 mmol) as prepared in the process of 4-A was dissolved in 30 mL of anhydrous THF, and the solution was slowly added to a reaction flask and allowed for reaction at ambient temperature for 12 hours. 1 mL of water, 1 mL of an aqueous 15% NaOH solution, and 3 mL of water were sequentially added to the solution to complete the reaction, and then THF was removed from the filtrate under reduced pressure, and solid was precipitated with hexane, and refiltered to obtain a compound 4b (2.45 g, yield 91%). MS $[M+H]^+$=238

4-C. Synthesis of Compound 4c

The compound 4b (2.45 g, 10.3 mmol) as prepared in the process of 4-B was dissolved in 50 mL of dichloromethane. PCC (pyridinium chlorochromate, 3.34 g, 15.49 mmol) and 1 g of Celite were added to the solution, and the solution was stirred at room temperature for 2 hours. After completion of the reaction, the reaction solution was passed through Celite, and filtered, and the filtrate was purified by column chromatography to obtain a compound 4c (0.87 g, yield 37%). MS $[M+H]^+$=234

4-D. Synthesis of Compound 4d 10-(2-Naphthyl)anthracene-9-boronic acid (3.6 g, 10 mmol), and the compound 4c (2 g, 8.5 mmol) as prepared in the process of 4-C were dissolved in THF (80 mL). A 2 M $K_2CO_3$ solution (60 mL) was added thereto, finally $Pd(PPh_3)_4$ (0.23 g, 0.3 mmol) was added to the mixture, and the mixture was stirred under reflux for about 12 hours. After completion of reaction, the mixture was cooled to ambient temperature, and the organic phase was separated from the mixed reaction solution, and removed. The residue was dissolved in THF and recrystallized from ethanol to obtain a compound 4d (2.4 g, 62%). MS [M]=458

4-E. Synthesis of Compound 5

Benzylphosphoric acid diethyl ether (1.2 mL, 5.8 mmol), sodium hydride (0.35 g, 14.1 mmol), 18-crown-6 (0.1 g, 0.47 mmol) were added to THF (80 mL), and the compound 4d (2.2 g, 4.7 mmol) as prepared in the process of 4-D was added to the mixture at 0° C., under $N_2$. The mixture was stirred at room temperature for about 12 hours. After completion of the reaction, THF and $H_2O$ were added to the mixed reaction solution. The organic phase was separated, dried over $MgSO_4$, and then concentrated. The residue was recrystallized from THF/EtOH to obtain a compound 5 (2.3 g, 90%). MS [M+H]=533

Example 5

Synthesis of Compound 11

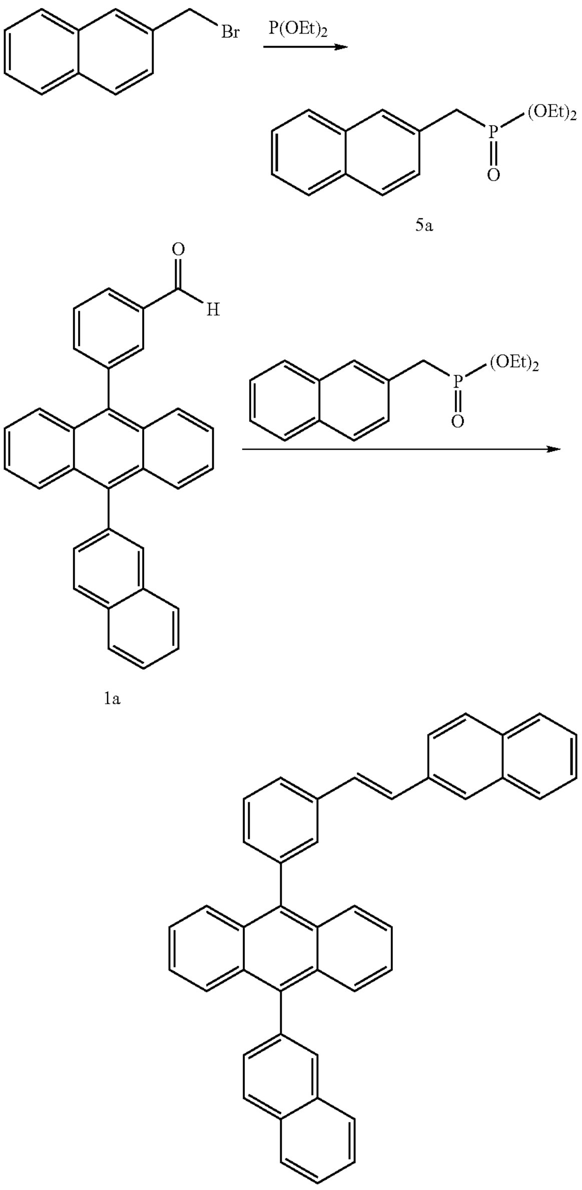

5a

1a

11

5-A. Synthesis of Compound 5a 2-(Bromomethyl)naphthalene (10 g, 45.2 mmol) was added to triethyl phosphite (30 mL, 180 mmol), and the mixture was stirred under reflux for 18 hours. The mixed reaction solution was slowly cooled, and the remaining triethyl phosphite was concentrated under reduced pressure to obtain a compound 5a (12 g, 96%) in the liquid form. MS $[M+H]^+=279$ 5-B. Synthesis of Compound 11

Sodium hydride (0.29 g, 12 mmol), 18-crown-6 (0.1 g, 0.48 mmol), and the compound 5a (2 g, 7.2 mmol) as prepared in the process of 5-A were added to THF (100 mL), and the compound 1a (2 g, 4.8 mmol) as prepared in the process of 1-A was added to the mixture at 0° C., under $N_2$. The mixture was stirred at room temperature for about 4 hours. After completion of the reaction, THF and $H_2O$ were added to the mixed reaction solution. The organic phase was separated, dried over $MgSO_4$, and then and concentrated. The residue was recrystallized from THF/EtOH to obtain a compound 11 (2.5 g, 98%). MS [M+H]=533

Example 6

Synthesis of Compound 12

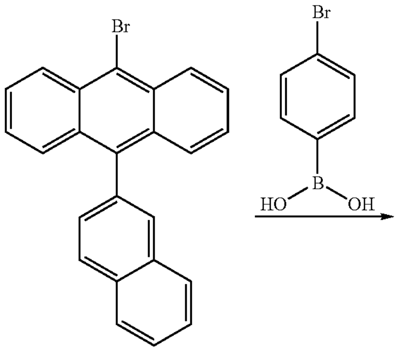

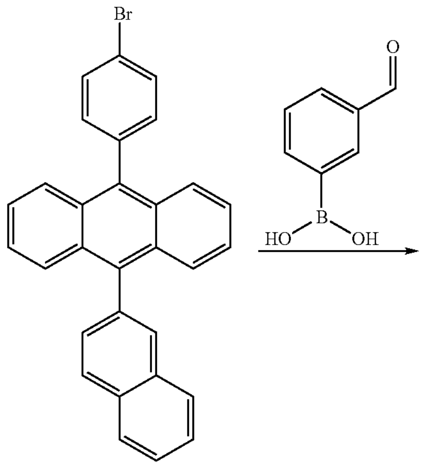

6a

-continued

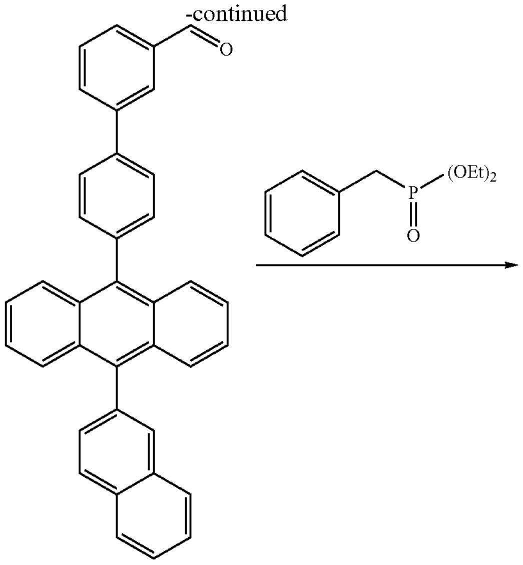

6b

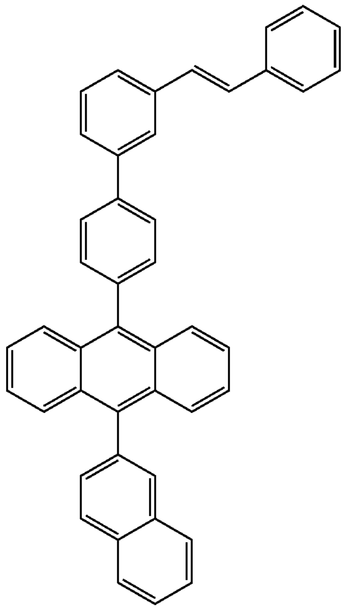

12

6-A. Synthesis of Compound 6a

To a solution obtained by dissolving 9-bromo-10-(2-naphthyl)anthracene (10 g, 26 mmol) in THF (200 mL), a solution obtained by dissolving 4-bromophenylboronic acid (6.3 g, 31.2 mmol) in EtOH (50 mL) was added, under $N_2$. To the mixture, a solution obtained by dissolving $K_2CO_3$ (14 g, 104 mmol) in $H_2O$ (100 mL), and finally $Pd(PPh_3)_4$ (0.58 g, 0.5 mmol) were added, and the mixture was stirred under reflux for about 17 hours. After completion of reaction, the mixture was cooled to ambient temperature, and the organic phase was separated from the mixed reaction solution, and filtered to obtain a solid. This solid was dissolved in THF again, and purified by column chromatography. Then, the residue was recrystallized from THF and ethanol to obtain a compound 6a (7 g, 58%). MS [M]=459

6-B. Synthesis of Compound 6b

To a solution obtained by dissolving the compound 6a (5 g, 11 mmol) as prepared in the process of 6-A in THF (70 mL), a solution obtained by dissolving 3-formyl benzene boronic acid (1.9 g, 13 mmol) in EtOH (40 mL) was added, under $N_2$. To the mixture, a solution obtained by dissolving $K_2CO_3$ (6 g, 44 mmol) in $H_2O$ (25 mL), and finally $Pd(PPh_3)_4$ (0.25 g, 0.2 mmol) were added, and the mixture was stirred under reflux for about 17 hours. After completion of reaction, the mixture was cooled to ambient temperature, and the organic phase was separated from the mixed reaction solution, and filtered to obtain a solid. This solid was dissolved in THF again, and purified by column chromatography. Then, the residue was recrystallized from THF and ethanol to obtain a compound 6b (3.2 g, 60%). MS [M]=484

6-C. Synthesis of Compound 12

Benzylphosphoric acid diethyl ether (1.2 mL, 5.8 mmol), sodium hydride (0.29 g, 7.2 mmol), 18-crown-6 (0.1 g, 0.48 mmol) were added to THF (100 mL), and the compound 6b (2.3 g, 4.8 mmol) as prepared in the process of 6-B was added to the mixture at 0° C., under $N_2$. The mixture was stirred at room temperature for about 12 hours. After completion of the reaction, THF and $H_2O$ were added to the mixed reaction solution. The organic phase was separated, dried over $MgSO_4$, and then concentrated. The residue was recrystallized from THF/EtOH to obtain a compound 12 (1.7 g, 65%). MS [M+H]=559

Example 7

Synthesis of Compound 15

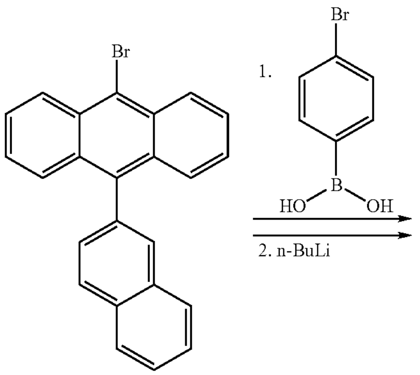

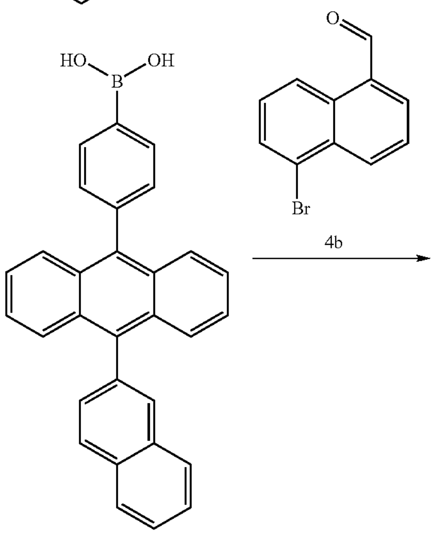

7a

-continued

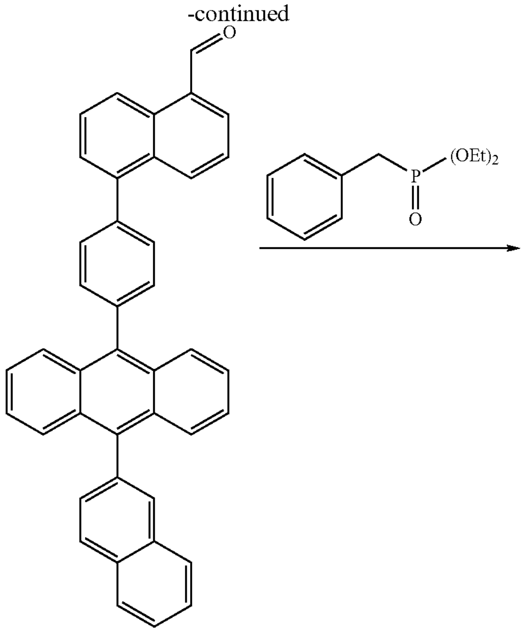

7b

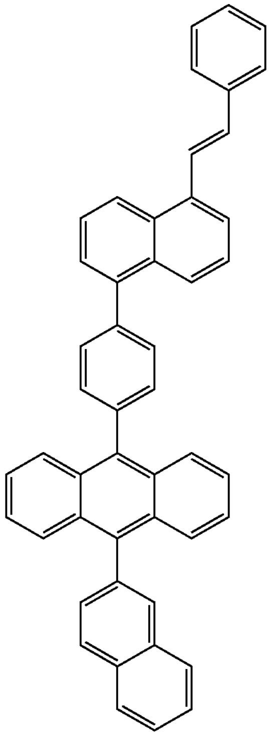

15

7-A. Synthesis of Compound 7a

A mixture of the compound 6a (10 g, 22 mmol) as prepared in the same manner as in the process of 6-A, dehydrated ether (100 mL) and dehydrated toluene (100 mL) was cooled to −78° C. in a dry ice bath. A 2.5 M butyl lithium/hexane solution (6 mL) was added dropwise thereto for 30 minutes, and the mixture was subject to reaction at −78° C. for 2 hours. Boronic acid triisopropyl ester (10 mL) was added dropwise thereto for 30 minutes. After adding dropwise, the mixture was stirred at room temperature for 12 hours. To the mixture, 2N hydrochloric acid (100 mL) was added at 10° C. or lower, and then toluene (80 mL) was added thereto. The mixture was subject to phase separation, dried over sodium sulfate, and concentrated under reduced pressure. Hexane was added thereto to precipitate crystals, and the precipitated crystals were separated by filtration. The residue was dissolved in THF (100 mL), and to this solution, concentrated hydrochloric acid (10 mL) and tetrabutylammonium bromide (0.1 g) were added, and the mixture was stirred for 12 hours. The precipitated crystals were dried to obtain a compound 7a (6 g, 66%).

7-B. Synthesis of Compound 7b

A compound 7b (3 g, 60%) was obtained in the same manner as in the process of 4-D of Example 4, except that the compound 7a as prepared in the process of 7-A was used instead of 10-(2-naphthyl)anthracene-9-boronic acid in the process of 4-D of Example 4. MS [M]=534

7-C. Synthesis of Compound 15

A compound 15 (1 g, 65%) was obtained in the same manner as in the process of 4-E of Example 4, except that the compound 7b as prepared in the process of 7-B was used instead of the compound 4d in the process of 4-E of Example 4. MS [M+H]=609

Example 8

Synthesis of Compound 25

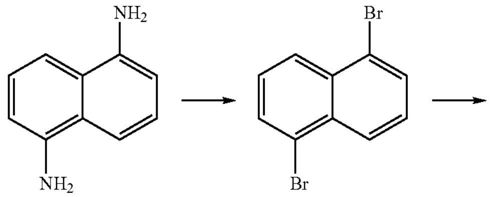

8a

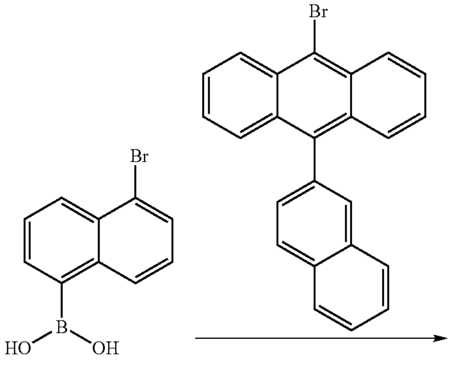

8b

-continued

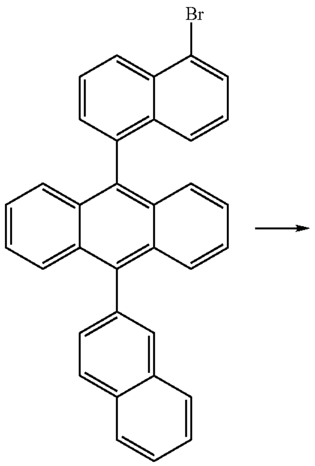

8c

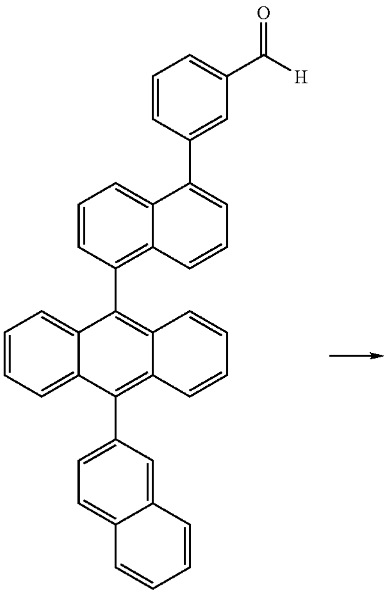

8d

-continued

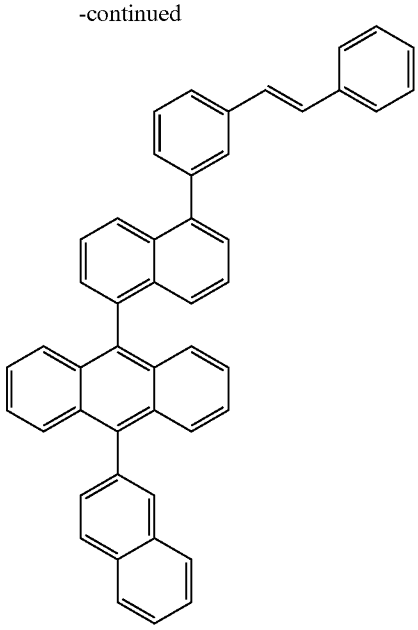

25

8-A. Synthesis of Compound 8a 1,5-Diaminonaphthalene (6 g, 75.9 mmol) was dissolved in water (150 mL) and concentrated sulfuric acid (10 mL) under ice cooling. A solution obtained by dissolving $NaNO_2$ (5.8 g, 167 mmol) in water (50 mL) was slowly added thereto, and then the mixture was stirred at 0° C. for 45 minutes. Thereafter, after filtering the reactants, $CuBr_2$ (15 g, 52.3 mmol) was added to the filtrate, and 48% HBr (225 mL) and water (225 mL) were added to the mixture. Then, the mixture was stirred at 0° C. for 1 hour, at room temperature for 2 hours, and then at 70° C. for 30 minutes, respectively. Then, the mixed reaction solution was extracted from benzene, and dried over sodium sulfate. Then, the residue was purified by column chromatography to obtain a compound 8a (10 g). MS [M]=286

8-B. Synthesis of Compound 8b

A mixture of the compound 8a (3.0 g, 10.5 mmol) as prepared in the process of 8-A, magnesium (0.26 g, 10.7 mmol), dibromoethene (0.1 mL), and anhydrous tetrahydrofuran (60 mL) was stirred at 50° C. for 7 hours, and then maintained at 0 to 5° C. To the reaction mixture, trimethylborate (2.6 mL, 25.2 mmol) was added dropwise, and then the mixture was stirred at ambient temperature for 12 hours. The reactants were maintained at 0 to 5° C., and then diluted sulfuric acid was added thereto. The mixture was stirred at room temperature for 1 hour, extracted from diethyl ether, and dried over anhydrous magnesium sulfate, and then the solvent was distilled off. The formed white solid was purified in hexane to prepare a compound 8b (1.47 g, yield 49%).

8-C. Synthesis of Compound 8c

A compound 8c (3 g, 60%) was obtained in the same manner as in the process of 6-A of Example 6, except that the compound 8b as prepared in the process of 8-B was used instead of 4-bromophenylboronic acid in the process of 6-A of Example 6. MS [M+H]=509

8-D. Synthesis of Compound 8d

A compound 8d (2.9 g, 90%) was obtained in the same manner as in the process of 6-B of Example 6, except that the compound 8c as prepared in the process of 8-C was used instead of the compound 6a in the process of 6-B of Example 6. MS [M+H]=535

8-E. Synthesis of Compound 25

A compound 25 (2 g, 60%) was obtained in the same manner as in the process of 6-C of Example 6, except that the compound 8d as prepared in the process of 8-D was used instead of the compound 6b in the process of 6-C of Example 6. MS [M+H]=609

Example 9

Synthesis of Compound 36

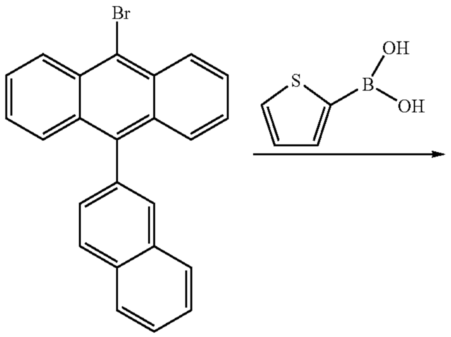

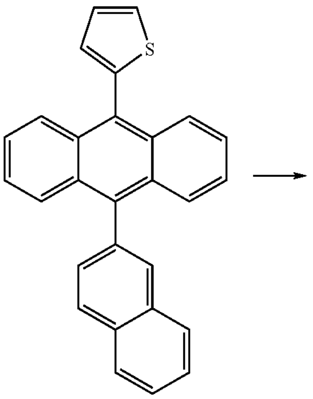

9a

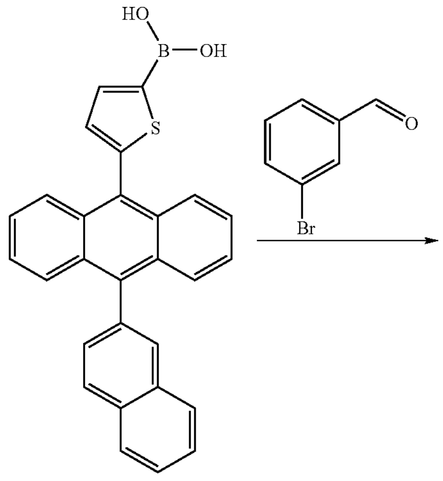

9b

-continued

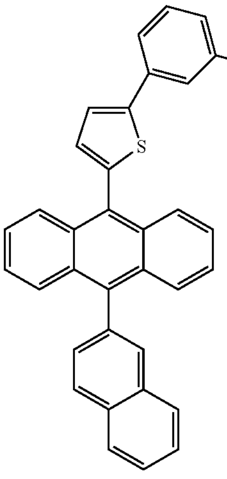

9c

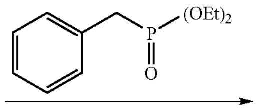

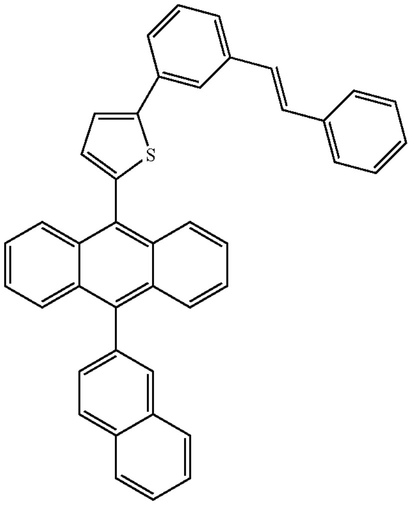

30

9-A. Synthesis of Compound 9a

To a solution obtained by dissolving 9-bromo-10-(2-naphthyl)anthracene (10 g, 26 mmol) in THF (200 mL), a solution obtained by dissolving 2-thiopheneboronic acid (4 g, 31 mmol) in EtOH (50 mL) was added, under $N_2$. To the mixture, a solution obtained by dissolving $K_2CO_3$ (14 g, 104 mmol) in $H_2O$ (100 mL), and finally $Pd(PPh_3)_4$ (0.58 g, 0.5 mmol) were added, and the mixture was stirred under reflux for about 17 hours. After completion of reaction, the mixture was cooled to ambient temperature, and the organic phase was separated from the mixed reaction solution, and filtered to obtain a solid. This solid was dissolved in THF again, and purified by column chromatography. Then, the residue was recrystallized from THF and ethanol to obtain a compound 9a (6 g, 60%). MS [M]=386

9-B. Synthesis of Compound 9b

To a solution obtained by dissolving the compound 9a (6 g, 15.5 mmol) as prepared in the process of 9-A in THF (100 mL), n-butyl lithium (7 mL, 31 mmol, 2.5 M hexane solution) was added dropwise at −78° C. over 30 minutes, under $N_2$, and the mixture was subject to reaction at −78° C. for 2 hours. Trimethylborate (3.5 mL, 31 mmol) was slowly added to the mixture for 30 minutes. After adding dropwise, the mixture was stirred at room temperature for 12 hours. To the mixture, 2 N hydrochloric acid (100 mL) was added at 10° C. or lower, and then toluene (80 mL) was added thereto. The mixture was subject to phase separation, dried over sodium sulfate, and concentrated under reduced pressure. Hexane was added thereto to precipitate crystals, and the precipitated crystals were separated by filtration. The residue was dissolved in THF (100 mL), and to this solution, concentrated sulfuric acid (10 mL) was added thereto, and the mixture was stirred for 12 hours. The precipitated crystals were dried to obtain a compound 9b (3.2 g, 50%). MS [M]=386

9-C. Synthesis of Compound 9c

A compound 9c (3 g, 60%) was obtained in the same manner as in the process of 4-D of Example 4, except that the compound 9b as prepared in the process of 9-B was used instead of 10-(2-naphthyl)anthracene-9-boronic acid in the process of 4-D of Example 4. MS [M+H]=490

9-D. Synthesis of Compound 36

A compound 36 (1 g, 65%) was obtained in the same manner as in the process of 4-E of Example 4, except that the compound 9c as prepared in the process of 9-C was used instead of the compound 4d in the process of 4-E of Example 4. MS [M+H]=565

Example 10

Synthesis of Compound 45

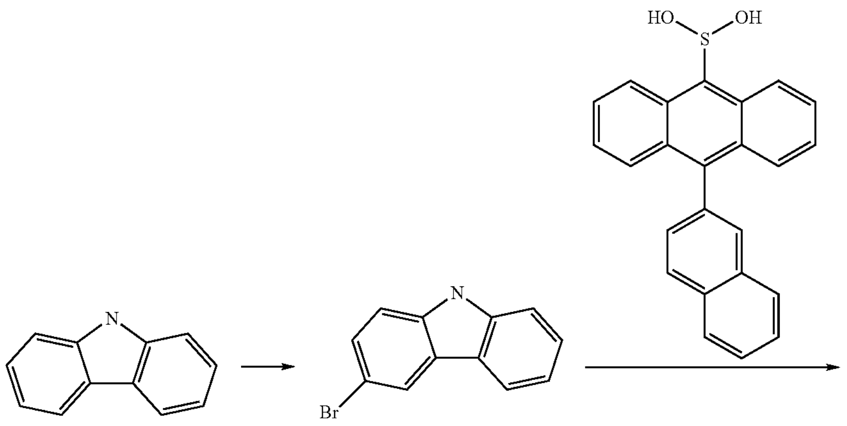

10a

-continued

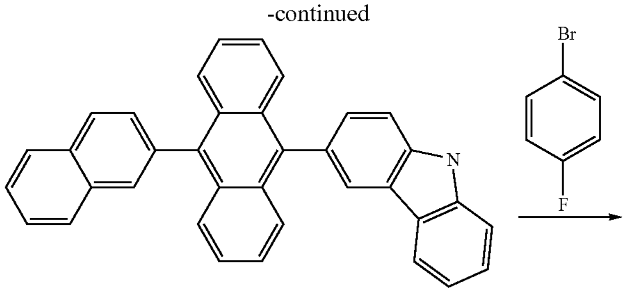

10b

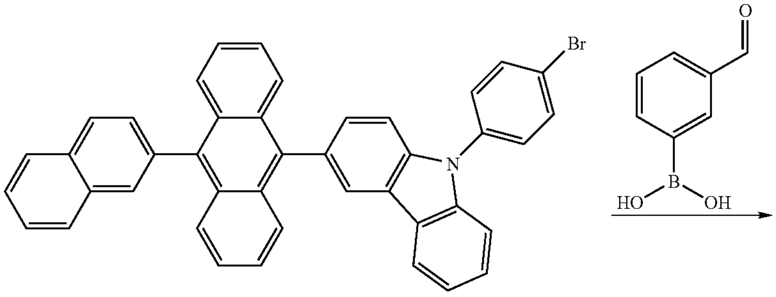

10c

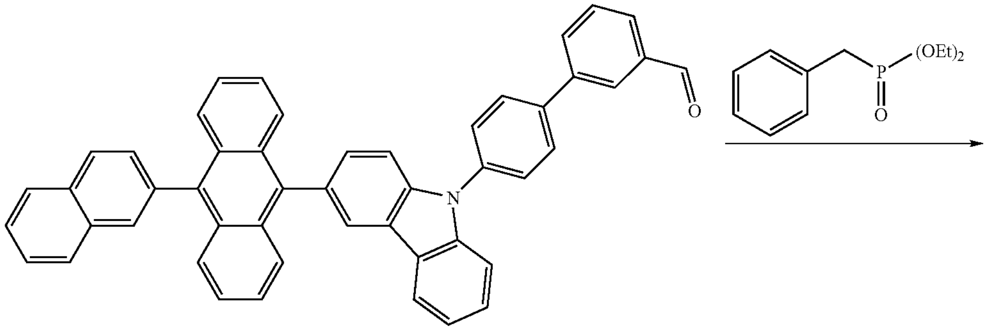

10d

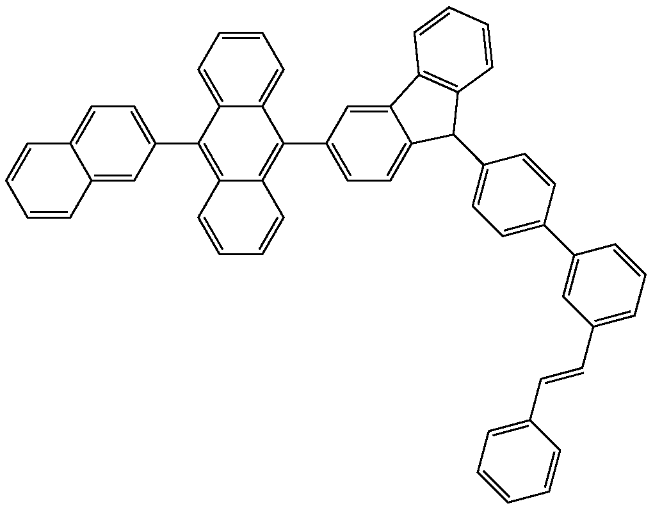

45

10-A. Synthesis of Compound 10a

Carbazole (10 g, 60 mmol), N-bromosuccinimide (5.4 g, 30 mmol), and silica gel (60 g) were dissolved in dichloromethane (200 mL). The solution was stirred at room temperature for 3 hours, then silica gel was removed, and the solution was distilled off under reduced pressure. The residue was recrystallized from dichloromethane/hexane to obtain a compound 10a (3.6 g, 50%). MS [M]=246

10-B. Synthesis of Compound 10b

To a solution obtained by dissolving the compound 10a (3 g, 12 mmol) as prepared in the process of 10-A in THF (70 mL), a solution obtained by dissolving 10-(2-naphthyl)anthracene-9-boronic acid (5.0 g, 14.6 mmol) in EtOH (40 mL) was added, under $N_2$. To the mixture, a solution obtained by dissolving $K_2CO_3$ (6.4 g, 48 mmol) in $H_2O$ (25 mL), and finally $Pd(PPh_3)_4$ (0.5 g, 0.47 mmol) were added, and the mixture was stirred under reflux for about 17 hours. After completion of reaction, the mixture was cooled to ambient temperature, and the organic phase was separated from the mixed reaction solution, and filtered to obtain a solid. This solid was dissolved in THF again, and purified by column chromatography. Then, the residue was recrystallized from THF and ethanol to obtain a compound 10b (4.2 g, 75%). MS [M]=469

10-C. Synthesis of Compound 10c

The compound 10b (4.2 g, 8.9 mmol) as prepared in the process of 10-A, 1-bromo-4-fluorobenzene (1.2 mL, 10.7 mmol), KF-alumina (2.6 g, 17.8 mmol), 18-crown-6 (0.24 g, 0.9 mmol) were dissolved in DMSO (75 mL) under $N_2$, and the solution was stirred at 150° C. for 24 hours. Alumina was filtered off at room temperature, the filtrate was subject to phase separation. The obtained organic phase washed with water, and then dried over magnesium sulfate. The residue was recrystallized from methanol, filtered, and then dried to obtain a compound 10c (3.3 g, 60%). MS [M]=624

10-D. Synthesis of Compound 10d

To a solution obtained by dissolving the compound 10c (3 g, 4.8 mmol) as prepared in the process of 10-C in THF (50 mL), a solution obtained by dissolving 3-formyl benzene boronic acid (1.1 g, 5.76 mmol) in EtOH (20 mL) was added, under $N_2$. To the mixture, a solution obtained by dissolving $K_2CO_3$ (2 g, 14 mmol) in $H_2O$ (25 mL), and finally $Pd(PPh_3)_4$ (0.28 g, 0.24 mmol) was added thereto, and the mixture was stirred under reflux for about 17 hours. After completion of reaction, the mixture was cooled to ambient temperature, and the organic phase was separated from the mixed reaction solution, and filtered to obtain a solid. This solid was dissolved in THF again, and purified by column chromatography. Then, the residue was recrystallized from THF and ethanol to obtain a compound 10d (2.2 g, 70%). MS [M]=649

10-E. Synthesis of Compound 45

Benzylphosphoric acid diethyl ether (0.8 mL, 3.7 mmol), sodium hydride (0.2 g, 9 mmol), and 18-crown-6 (0.08 g, 0.3 mmol) were added to THF (80 mL), and the compound 10d (2 g, 3 mmol) as prepared in the process of 10-D was added to the mixture at 0° C., under $N_2$. The mixture was stirred at room temperature for 12 hours. After completion of the reaction, to the mixed reaction solution, THF and $H_2O$ were added. The organic phase was separated from the mixed reaction solution, dried over $MgSO_4$, and concentrated. The residue was recrystallized from THF/EtOH to obtain a compound 45 (1.8 g, 85%). MS [M+H]=724

Example 11

Synthesis of Compound 50

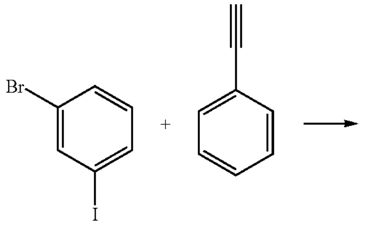

-continued

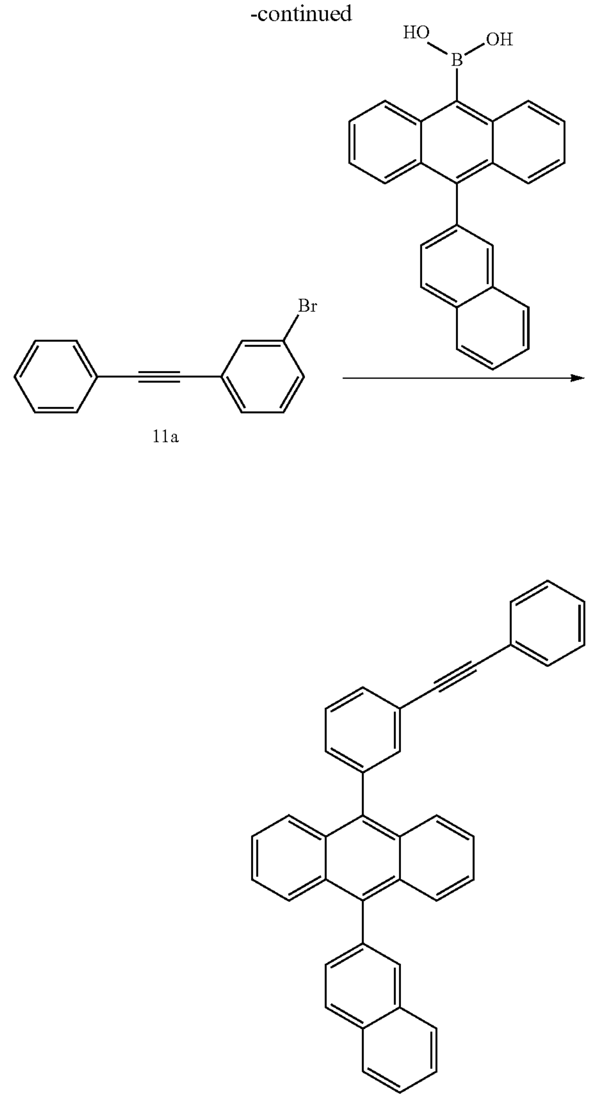

11a

50

II-A. Synthesis of Compound 11a

To a reaction vessel, $Pd(PPh_3)_2Cl_2$ (372 mg, 0.53 mmol) and CuI (67 mg, 0.35 mmol) were put, and a solution obtained by dissolving 1-bromo-3-iodobenzene (5 g, 17.7 mmol) in triethylamine was slowly added thereto, and then a solution obtained by dissolving phenylacetylene (1.8 g, 17.7 mmol) in TEA was also added thereto. The mixture was stirred at ambient temperature for 1 hour, and then washed with an aqueous $NH_4Cl$ solution, and the organic phase was extracted from ethyl acetate. The moisture was removed over anhydrous magnesium sulfate, the residue was filtered under reduced pressure, and then concentrated. Then, the solvent was removed therefrom, and the residue was purified by column chromatography to obtain a compound 11a (4.5 g, 99%). MS [M+H]=258

11-B. Synthesis of Compound 50

The compound 11a (1.23 g, 4.8 mmol) as prepared in the process of 11-A and 10-(2-naphthyl)anthracene-9-boronic acid (2 g, 5.76 mmol) were dissolved in anhydrous THF (30 mL), $Pd(PPh_3)_4$ (0.28 g, 0.24 mmol) and an aqueous $K_2CO_3$ solution (9.6 mL, 19.2 mmol) were added thereto, and the mixture was refluxed for 3 hours. The mixture washed with brine, and the organic phase was extracted from ethyl acetate. The moisture was removed over anhydrous magnesium sulfate, the residue was filtered under reduced pressure, and then concentrated. Then, the solvent was removed therefrom, and the residue was purified by column chromatography, and then recrystallized from THF and ethanol to obtain a compound 50 (0.9 g, 33%). MS [M+H]=481

Example 12

Synthesis of Compound 65

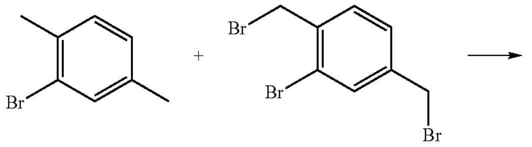

12a

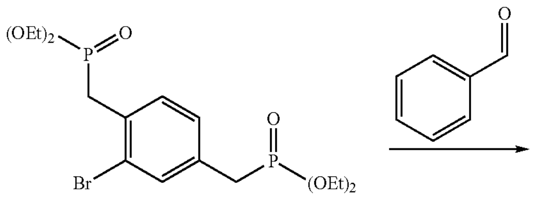

12b

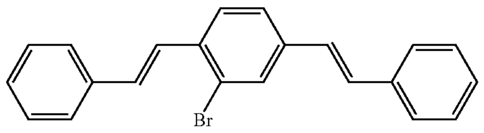

12c

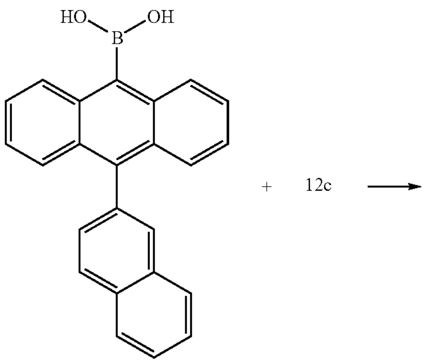

-continued

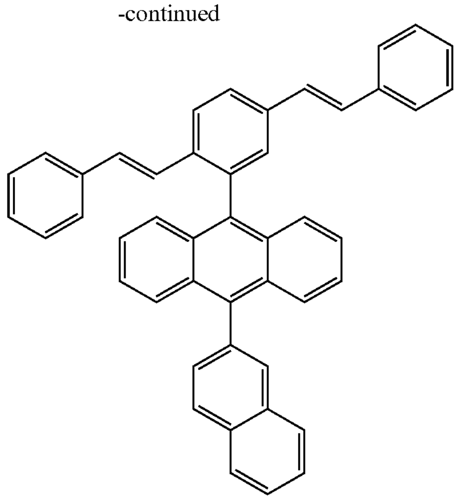

65

12-A. Synthesis of Compound 12a

2-Bromo-p-xylene (2.7 g, 14.5 mmol) and NBS (6.2 g, 34.8 mmol) were added to $CCl_4$ (70 mL), and the mixture was stirred under reflux for 17 hours. The mixed reaction solution was slowly cooled, succinimide was filtered off, and the filtrate was concentrated. The residue was recrystallized from 2-propanol to obtain a solid compound 12a (1.5 g, 30%). MS $[M]^+$=340 (Br×3)

12-B. Synthesis of Compound 12b

The compound 12a (16.1 g, 46.9 mmol) as prepared in the process of 12-A was added to triethyl phosphite (31.5 mL, 187.6 mmol), and the mixture was stirred under reflux for 17 hours. The mixed reaction solution was slowly cooled, and the residual triethyl phosphite as concentrated under reduced pressure to a compound 12b (20 g, 95%) in the liquid form. MS $[M+H]^+$=457

12-C. Synthesis of Compound 12c

The compound 12b (11 g, 24.1 mmol) as prepared in the process of 12-B, and sodium hydride (5.9 g, 14.8 mmol), 18-crown-6 (1.3 g, 4.9 mmol) were added to THF (100 mL), and benzaldehyde (5 mL, 49.2 mmol) was added to the mixture at 0° C., under $N_2$. The mixture was stirred at room temperature for about 12 hours. To the mixed reaction solution, THF and $H_2O$ were added. The organic phase was separated from the mixed reaction solution, dried over $MgSO_4$, and concentrated. The residue was recrystallized from THF/EtOH to obtain a compound 12c (5.2 g, 60%). MS [M+H]=362

12-D. Synthesis of Compound 65

The compound 12c (1 g, 2.7 mmol) as prepared in the process of 12-C, 10-(2-naphthyl)anthracene-9-boronic acid (2.8 g, 8.1 mmol), and $Pd(PPh_3)_4$ (0.3 g, 0.3 mmol) were added to a 2 M aqueous $K_2CO_3$ solution (200 mL) and THF (200 mL), and the mixture was stirred under reflux for about 24 hours. After completion of reaction, the mixture was cooled to ambient temperature, and the organic phase was separated from the mixed reaction solution, and filtered to obtain a solid. This solid was dissolved in THF again, and purified by column chromatography. Then, the residue was recrystallized from THF and ethanol to obtain a compound 65 (1.1 g, 70%). MS [M+H]=585

Example 13

Synthesis of Compound 67

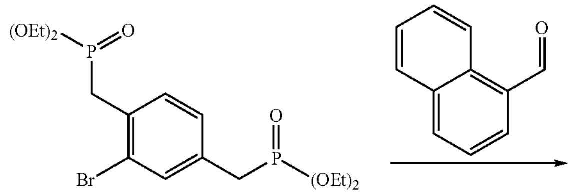

12b

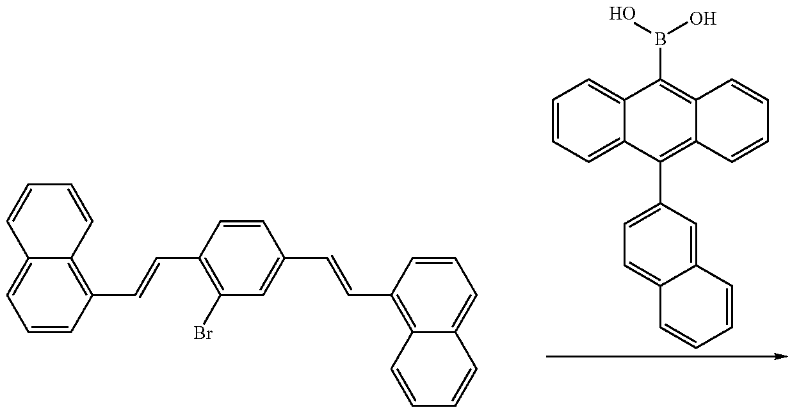

13a

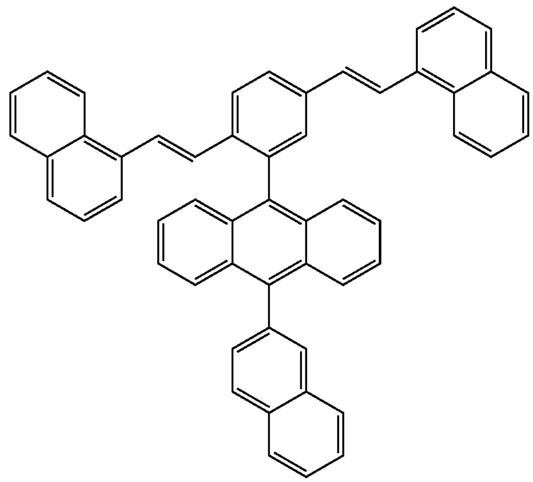

67

13-A Synthesis of Compound 13a

The compound 12b (11 g, 24.1 mmol) as prepared in the process of 12-B of Example 12, sodium hydride (5.9 g, 14.8 mmol), and 18-crown-6 (1.3 g, 4.9 mmol) were added to THF (100 mL), and 1-naphthylaldehyde (5 mL, 49.2 mmol) was added thereto at 0° C. The mixture was stirred at room temperature for about 12 hours. To the mixed reaction solution, THF and $H_2O$ were added. The organic phase was separated from the mixed reaction solution, dried over $MgSO_4$, and concentrated. The residue was recrystallized from THF/EtOH to obtain a compound 13a (5.2 g, 60%). MS [M+]=460

13-B. Synthesis of Compound 67

The compound 13a (3 g, 19.5 mmol) as prepared in the process of 13-A, 10-(2-naphthyl)anthracene-9-boronic acid (6.8 g, 19.5 mmol), and $Pd(PPh_3)_4$ (0.23 g, 0.2 mmol) were added to a 2 M aqueous $K_2CO_3$ solution (200 mL) and THF (100 mL), and the mixture was stirred under reflux for about 24 hours. After completion of reaction, the mixture was cooled to ambient temperature, and the organic phase was separated from the mixed reaction solution, and filtered to obtain a solid. This solid was dissolved in THF again, and purified by column chromatography. Then, the residue was recrystallized from THF and ethanol to obtain a compound 67 (4.7 g, 80%). MS [M+H]=684

Example 14

Synthesis of Compound 69

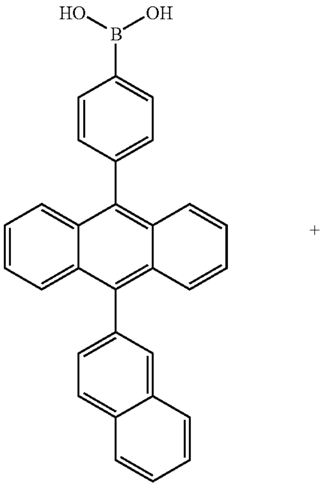

7a

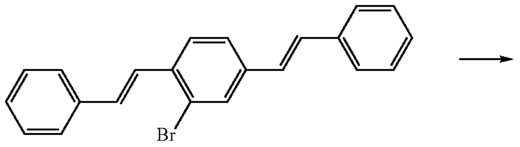

12c

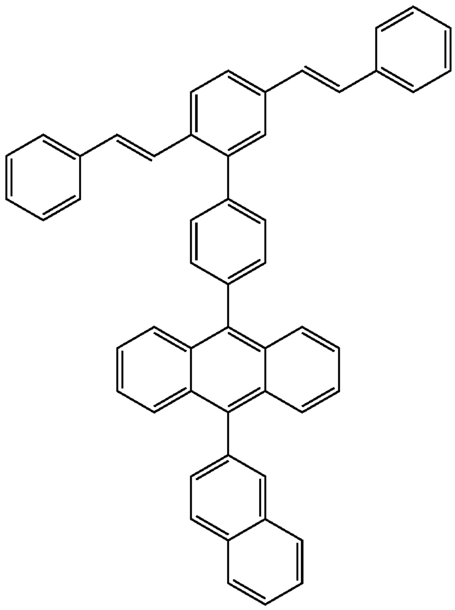

69

The compound 7a (1 g, 2.7 mmol) as prepared in the process of 7-A of Example 7, the compound 12c (1.4 g, 3.3 mmol) as prepared in the process of 12-C of Example 12, and $Pd(PPh_3)_4$ (0.15 g, 0.14 mmol) were added to a 2 M aqueous $K_2CO_3$ solution (100 mL) and THF (100 mL), and the mixture was stirred under reflux for about 24 hours. After completion of reaction, the mixture was cooled to ambient temperature, and the organic phase was separated from the mixed reaction solution, and filtered to obtain a solid. This solid was dissolved in THF again, and purified by column chromatography. Then, the residue was recrystallized from THF and ethanol to obtain a compound 69 (1.2 g, 70%). MS [M+H]=661

Example 15

Synthesis of Compound 90

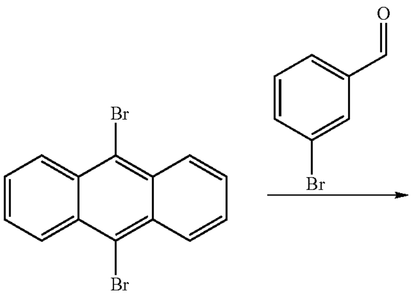

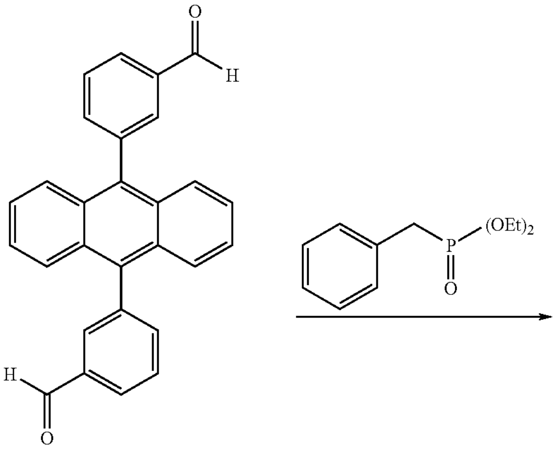

15a

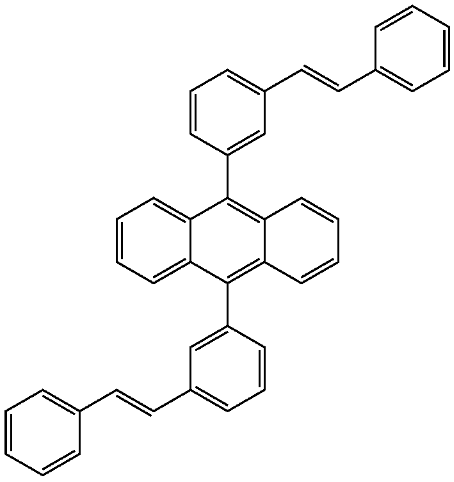

90

15-A. Synthesis of Compound 15a

To a solution obtained by dissolving 9,10-dibromoanthracene (5 g, 14.8 mmol) in THF (50 mL), a solution obtained by dissolving 3-formyl benzene boronic acid (5.5 g, 37.0 mmol) in EtOH (20 mL) was added, under $N_2$. To the mixture, a solution obtained by dissolving $K_2CO_3$ (8.1 g, 59.2 mmol) in $H_2O$ (50 mL), and finally $Pd(PPh_3)_4$ (0.3 g, 0.3 mmol) was added thereto, and the mixture was stirred under reflux for about 17 hours. After completion of reaction, the mixture was cooled to ambient temperature, and the organic phase was separated from the mixed reaction solution, and filtered to obtain a solid. This solid was dissolved in THF again, and purified by column chromatography. Then, the residue was recrystallized from THF and ethanol to obtain a compound 15a (5 g, 90%). MS [M]=386

15-B. Synthesis of Compound 90

Benzylphosphoric acid diethyl ether (3.2 mL, 15.3 mmol), sodium hydride (0.8 g, 20 mmol), and 18-crown-6 (0.1 g, 0.5 mmol) were added to THF (100 mL), and the compound 15a (2 g, 5.1 mmol) as prepared in the process of 15-A was added to the mixture at 0° C., under $N_2$. The mixture was stirred at room temperature for about 24 hours. After completion of the reaction, THF and $H_2O$ were added to the mixed reaction solution. The organic phase was separated, dried over $MgSO_4$, and then concentrated. The residue was recrystallized from THF/EtOH to obtain a compound 90 (2.6 g, 95%). MS [M+H]=534

Example 16

Synthesis of Compound 112

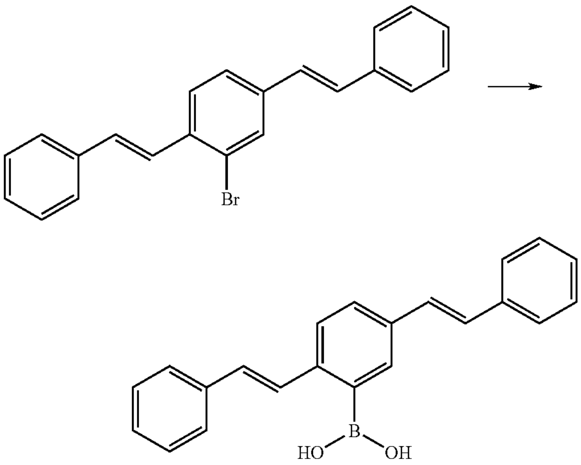

16a

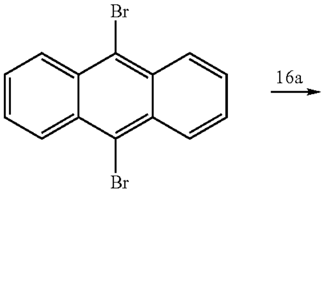

-continued

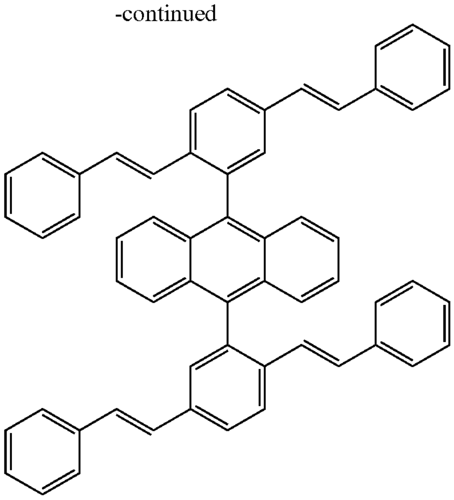

112

16-A. Synthesis of Compound 16a

To the reaction solution, which was added with magnesium (0.7 g, 27.6 mmol), dried in vacuo, and then added with ether (20 mL) which had been dried by dehydration, the compound 12c (5 g, 13.8 mmol) as prepared in the process of 12-C of Example 12 in the solution form added with ether (50 mL) which had been dried by dehydration was added dropwise, under $N_2$. The mixture was stirred at room temperature for 2 hours, and then trimethylborate (2.3 mL, 20.7 mmol) was added thereto for 30 minutes and then stirred again for 12 hours. To the mixture, 2 N hydrochloric acid (100 mL) was added at 10° C. or lower, and then toluene (80 mL) was added thereto. The mixture was subject to phase separation, dried over sodium sulfate, and concentrated under reduced pressure. Hexane was added thereto to precipitate crystals, and the precipitated crystals were separated by filtration and dried to obtain a compound 16a (2 g, 44%).

16-B. Synthesis of Compound 112

9,10-Dibromoanthracene (1 g, 2.9 mmol), the compound 16a (2.1 g, 6.5 mmol) as prepared in the process of 16-A, and $Pd(PPh_3)_4$ (0.15 g, 0.14 mmol) were dissolved in THF (50 mL), and then the solution was added to a 2 M aqueous $K_2CO_3$ solution (50 mL). The mixture was stirred under reflux for about 24 hours. After completion of reaction, the mixture was cooled to ambient temperature, and the organic phase was separated from the mixed reaction solution, and filtered to obtain a solid. This solid was dissolved in THF again, and purified by column chromatography. Then, the residue was recrystallized from THF and ethanol to obtain a compound 112 (1.5 g, 70%). MS [M+H]=739

Example 17

Synthesis of Compound 124

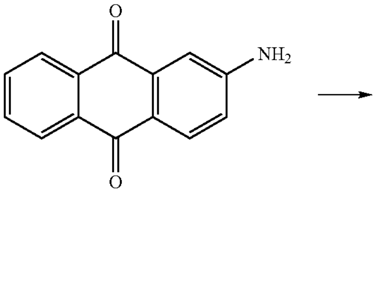

-continued

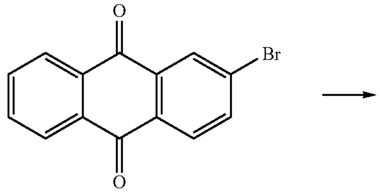

17a

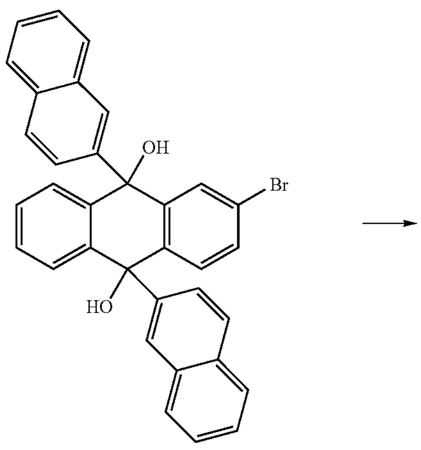

17b

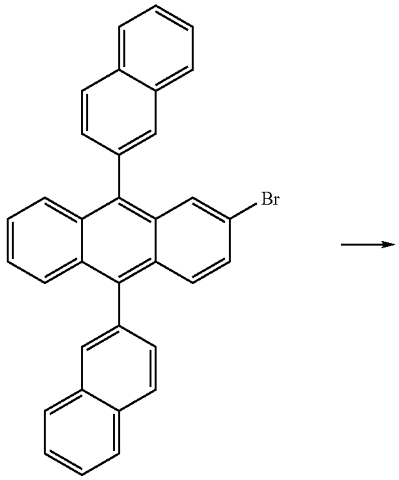

17c

-continued

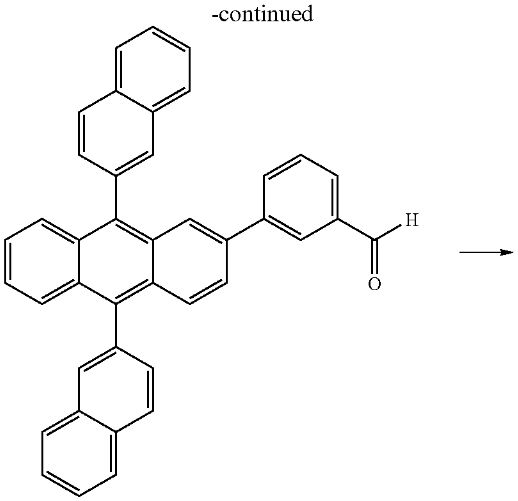

17d

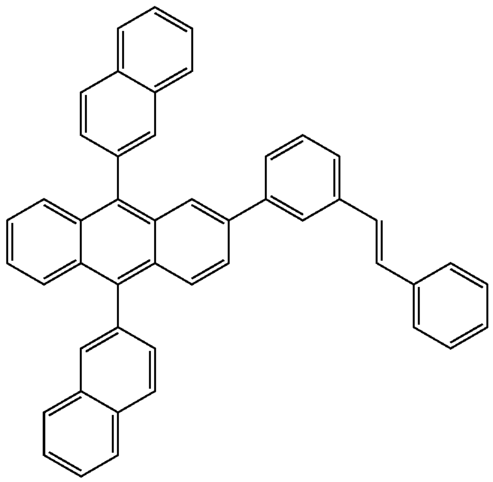

124

17-A. Synthesis of Compound 17a

Copper bromide (18 g, 80.0 mmol) and t-butyl nitrite (12 mL, 101 mmol) were dispersed in acetonitrile (250 mL) at 65° C., and the dispersion was stirred, and then 2-aminoanthraquinone (15 g, 67.2 mmol) was slowly added over 5 minutes. After completion of gas generation, the reaction solution was cooled to ambient temperature, and the reaction solution was added to an aqueous 20% hydrochloric acid solution (1 L), and extracted from dichloromethane. Residual moisture was removed from the organic phase over anhydrous magnesium sulfate, and the residue was dried under reduced pressure. The residue was purified by column chromatography to obtain a pale yellow compound 17a (14.5 g, 75%). MS [M]=287

17-B. Synthesis of Compound 17b

2-Bromonaphthalene (11.0 g, 53.1 mmol) was dissolved in dried THF (100 mL), t-butyl lithium (46.8 mL, 1.7 M pentane solution) was slowly added to the solution at −78° C., under nitrogen atmosphere. The mixture was stirred at the same temperature for 1 hour, and then the compound 17a (6.36 g, 22.0 mmol) as prepared in the process of 17-A was added thereto. The cooling vessel was removed out, and the mixture was stirred at ambient temperature for 3 hours. An aqueous ammonium chloride solution was added to the reaction mixture, and the mixture was extracted from methylene chloride. The organic phase was dried over anhydrous magnesium sulfate, and the solvent was removed. The obtained mixture was dissolved in a small amount of ethyl ether, petroleum ether was added thereto, and the mixture was stirred for several hours to obtain a solid compound. The solid compound is filtered off, the residue was dried in vacuo to obtain a compound 17b (11.2 g, 93%).

17-C. Synthesis of Compound 17c

The compound 17b (11.2 g, 20.5 mmol) as prepared in the process of 17-B was dispersed in acetic acid (200 mL), and to the dispersion, potassium iodide (34 g, 210 mmol), and sodium hypophosphite hydrate (37 g, 420 mmol) were added, under nitrogen atmosphere. The mixture was stirred for 3 hours under boiling. The mixture was cooled to ambient temperature, filtered, washed with water and methanol, and dried in vacuo to obtain a pale yellow compound 17c (7.2 g, 64%). MS [M]=509

17-D. Synthesis of Compound 17d

The compound 17c (7 g, 13.74 mmol) as prepared in the process of 17-C was dissolved in THF (150 mL), and a solution obtained by dissolving 3-formyl benzene boronic acid (2.47 g, 16.48 mmol) in EtOH (50 mL) was added thereto, under nitrogen atmosphere. To the mixture, a solution obtained by dissolving $K_2CO_3$ (5.7 g, 41.2 mmol) in $H_2O$ (100 mL), and finally $Pd(PPh_3)_4$ (0.48 g, 0.41 mmol) was added thereto, and the mixture was stirred under reflux for about 12 hours. After completion of reaction, the mixture was cooled to ambient temperature, and the organic phase was separated from the mixed reaction solution, and filtered to obtain a solid. This solid was dissolved in THF again, and purified by column chromatography. Then, the residue was recrystallized from THF and ethanol to obtain a compound 17d (6.3 g, 86%). MS [M]=534

17-E. Synthesis of Compound 124

Benzylphosphoric acid diethyl ether (1.2 mL, 5.8 mmol), sodium hydride (0.29 g, 7.2 mmol), and 18-crown-6 (0.1 g, 0.48 mmol) were added to THF (100 mL), and the compound 17d (2.57 g, 4.8 mmol) as prepared in the process of 17-D was added to the mixture at 0° C., under nitrogen atmosphere. The mixture was stirred at room temperature for about 12 hours. After completion of the reaction, THF and $H_2O$ were added to the mixed reaction solution. The organic phase was separated, dried over $MgSO_4$, and then concentrated. The residue was recrystallized from THF/EtOH to obtain a compound 124 (2.4 g, 82%). MS [M+H]=608

Example 18

Synthesis of Compound 125

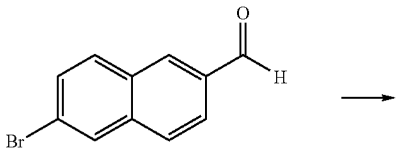

-continued

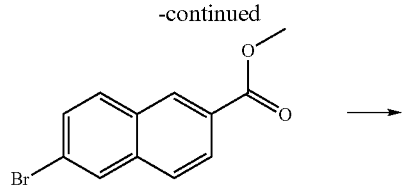

18a

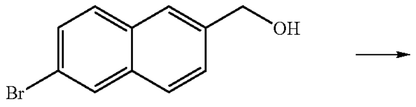

18b

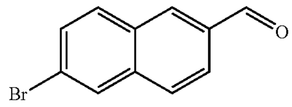

18c

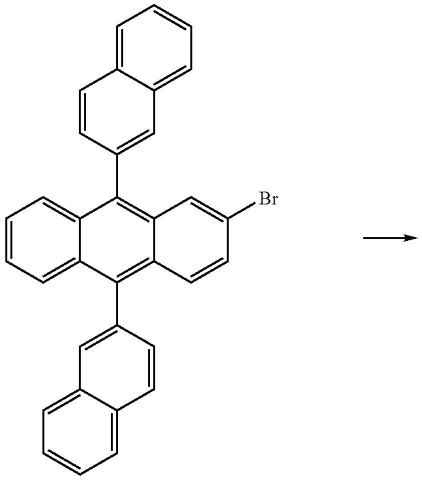

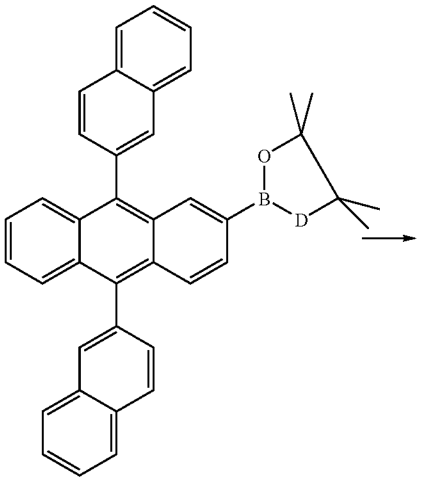

18d

-continued

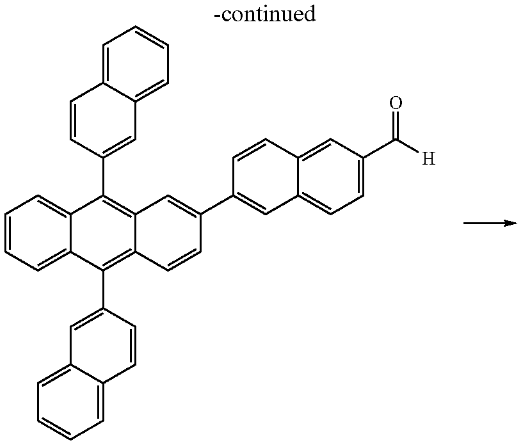

18e

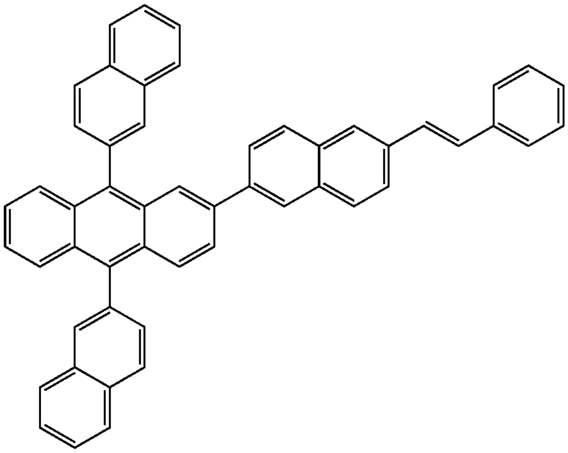

125

18-A. Synthesis of Compound 18a

To a mixture of 6-bromo-2-naphthoic acid (3 g, 11.95 mmol), iodomethane (MeI, 1.11 mL), and $K_2CO_3$ (6.58 g, 47.61 mmol), 30 mL of DMF was added, and the mixture was stirred at ambient temperature for 5 hours. After observation of completion of the reaction by means of TLC, the reaction solution was filtered to remove $K_2CO_3$. About 20 mL of DMF was removed from the filtrate under reduced pressure, and water was poured to the residue to precipitate a solid. The obtained solid was filtered, and then the residue washed with ethanol, and dried to obtain a compound 18a (3.06 g, yield 97%). MS $[M+H]^+$=264

18-B. Synthesis of Compound 18b

A mixture of LAH (Lithium aluminum hydride, 0.86 g, 22.7 mmol) and anhydrous THF (10 mL) was cooled to a temperature of 0° C. The compound 18a (2.3 g, 8.67 mmol) as prepared in the process of 18-A was dissolved in 30 mL of anhydrous THF, and the solution was slowly put to a reaction flask, and subject to reaction at ambient temperature for 12 hours. 1 mL of water, 1 mL of an aqueous 15% NaOH solution, and 3 mL of water were sequentially added to the solution to complete the reaction, and then THF was removed from the filtrate under reduced pressure, and solid was precipitated with hexane, and refiltered to obtain a compound 18b (2.45 g, yield 91%). MS $[M+H]^+$=238

18-C. Synthesis of Compound 18c

The compound 18b (2.45 g, 10.3 mmol) as prepared in the process of 18-B was dissolved in 50 mL of dichloromethane. PCC (pyridinium chlorochromate, 3.34 g, 15.49 mmol) and 1 g of Celite were added to the solution, and the solution was stirred at room temperature for 2 hours. After completion of the reaction, the reaction solution was passed through Celite, and filtered, and the filtrate was purified by column chromatography to obtain a compound 18c (0.87 g, yield 37%). MS $[M+H]^+$=234

18-D. Synthesis of Compound 18d

The compound 17c 75 g, 9.81 mmol) as prepared in the process of 17-C, bis(pinacolato)diboron (2.75 g, 10.9 mmol), potassium acetate (2.89 g, 29.4 mmol), palladium(diphenylphosphinoferocene)chloride (0.24 g, 3 mol %) were put to a 250-mL flask, and dioxane (50 mL) was added thereto, under nitrogen atmosphere, and then stirred at 80° C. for 6 hours. The reaction solution was cooled to room temperature, and the distilled water (50 mL) was added thereto. The mixture was extracted from methylene chloride (50 mL×3). Methylene chloride was removed under reduced pressure to obtain a pale yellow solid. This pale yellow solid was washed with ethanol and dried to obtain a compound 18d (5.46 g, 92%).

18-E. Synthesis of Compound 18e

The compound 18d (5.6 g, 10 mmol) as prepared in the process of 18-D, and the compound 18c (2 g, 8.5 mmol) as prepared in the process of 18-C were dissolved in THF (120 mL) under nitrogen atmosphere. A 2 M $K_2CO_3$ solution (60 mL) was added thereto, finally $Pd(PPh_3)_4$ (0.23 g, 0.3 mmol) was added to the mixture, and the mixture was stirred under reflux for about 12 hours. After completion of reaction, the mixture was cooled to ambient temperature, and the organic phase was separated from the mixed reaction solution, and removed. The residue was dissolved in THF and recrystallized from ethanol to obtain a compound 18e (4.1 g, 82%). MS [M+H]+=583

18-F. Synthesis of Compound 125

Benzylphosphoric acid diethyl ether (1.2 mL, 5.8 mmol), sodium hydride (0.29 g, 7.2 mmol), 18-crown-6 (0.1 g, 0.48 mmol) were added to THF (100 mL), and the compound 18e (2.8 g, 4.8 mmol) as prepared in the process of 18-E was added to the mixture at 0° C., under nitrogen atmosphere. The mixture was stirred at room temperature for about 12 hours. After completion of the reaction, THF and $H_2O$ were added to the mixed reaction solution. The organic phase was separated, dried over $MgSO_4$, and then concentrated. The residue was recrystallized from THF/EtOH to obtain a compound 125 (2.7 g, 85%). MS [M+H]=659

Example 19

Synthesis of Compound 133

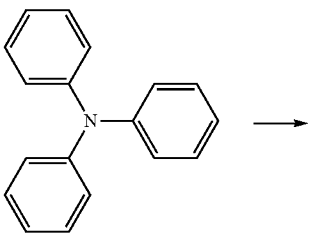

-continued

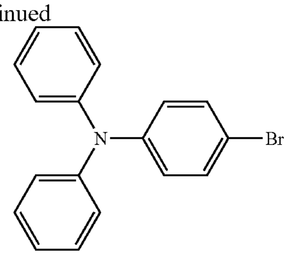

19a

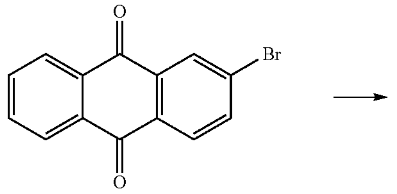

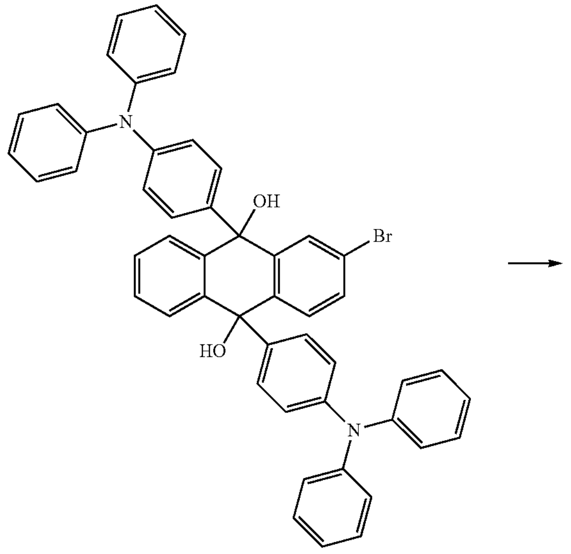

19b

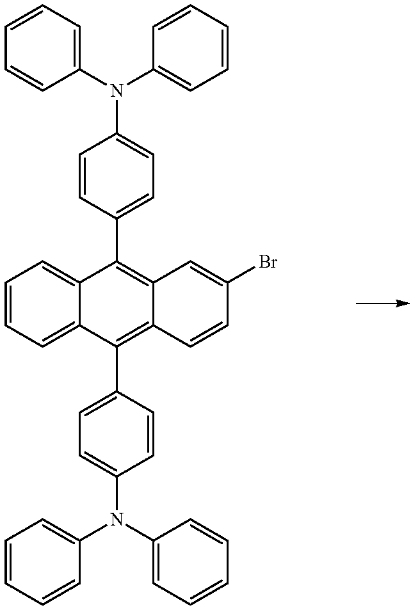

19c

-continued

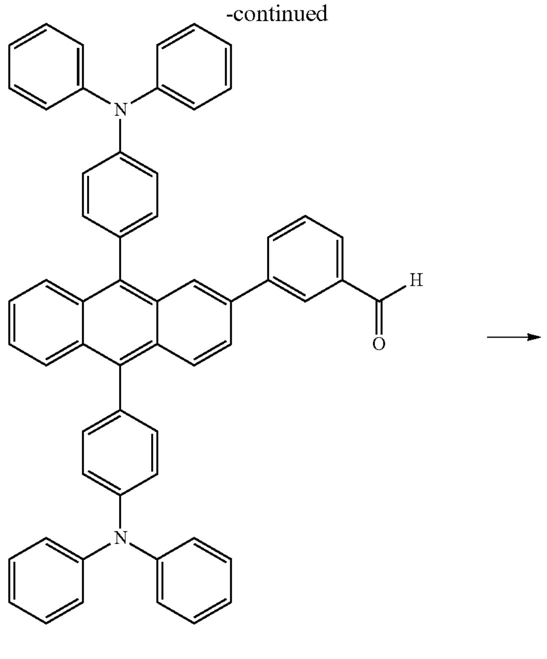

19d

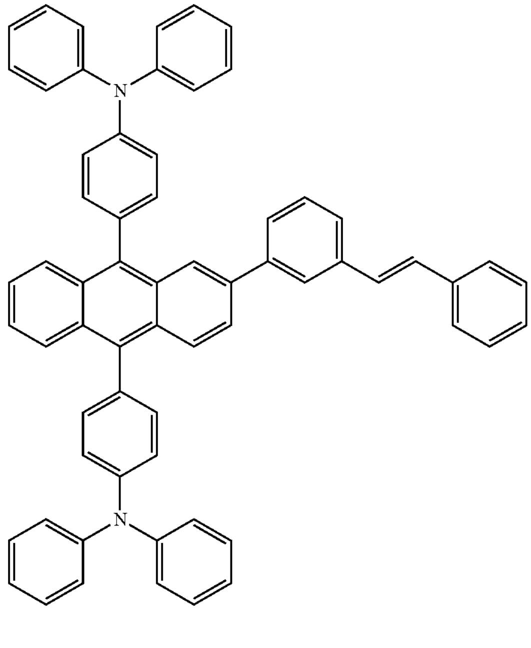

19e

19-A. Synthesis of Compound 19a

Triphenyl amine (5.0 g, 20.4 mmol) was dissolved in chloroform (25 mL) under nitrogen atmosphere, the mixed reaction solution was cooled to 0° C., and N-bromosuccinimide (3.6 g, 20.4 mmol) was dividedly added thereto. Thereafter, when the mixed reaction solution turned green, the temperature of the solution was raised to 10° C., and stirred at room temperature for 12 hours. After completion of the reaction, water was added thereto, and the organic phase was separated and dried over anhydrous sodium sulfate. Then, the organic solvent was distilled off under reduced pressure, and then the residue was recrystallized from methanol to obtain a compound 19a (4.0 g, 60%). MS [M+H]+=324

19-B. Synthesis of Compound 19b

The compound 19a (17.2 g, 53.1 mmol) as prepared in the process of 19-A was dissolved in dried THF (100 mL), and t-butyl lithium (46.8 mL, 1.7 M pentane solution) was slowly added to the solution at −78° C., under nitrogen atmosphere. The mixture was stirred at the same temperature for 1 hour, and then the compound 17a (6.36 g, 22.0 mmol) as prepared in the process of 17-A was added thereto. The cooling vessel was removed out, and the mixture was stirred at ambient temperature for 3 hours. An aqueous ammonium chloride solution was added to the reaction mixture, and the mixture was extracted from methylene chloride. The organic phase was dried over anhydrous magnesium sulfate, and the solvent was removed. The obtained mixture was dissolved in a small amount of ethyl ether, petroleum ether was added thereto, and the mixture was stirred for several hours to obtain a solid compound. The solid compound is filtered off, the residue was dried in vacuo to obtain a compound 19b (15.9 g, 93%).

19-C. Synthesis of Compound 19c

The compound 19b (15.9 g, 20.5 mmol) as prepared in the process of 19-B was dispersed in acetic acid (200 mL), and to the dispersion, potassium iodide (34 g, 210 mmol), and sodium hypophosphite hydrate (37 g, 420 mmol) were added, under nitrogen atmosphere. The mixture was stirred for 3 hours under boiling. The mixture was cooled to ambient temperature, filtered, washed with water and methanol, and dried in vacuo to obtain a pale yellow compound 19c (9.9 g, 65%). MS [M+H]+=743

19-D. Synthesis of Compound 19d

A compound 19d (11 g, 82%) was obtained in the same manner as in the process of 17-D of Example 17, except that the compound 19c as prepared in the process of 19-C was used instead of the compound 17c in the process of 17-D of Example 17. MS [M+H]+=768

19-E. Synthesis of Compound 133

A compound 133 (3.4 g, 85%) was obtained in the same manner as in the process of 17-E of Example 17, except that the compound 19d as prepared in the process of 19-D was used instead of the compound 17d in the process of 17-E of Example 17. MS [M+H]+=842

Example 20

Synthesis of Compound 136

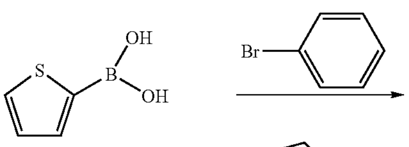

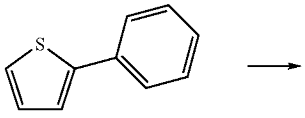

20a

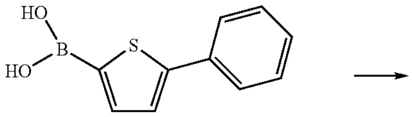

20b

-continued

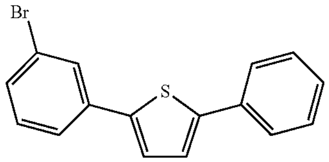

20c

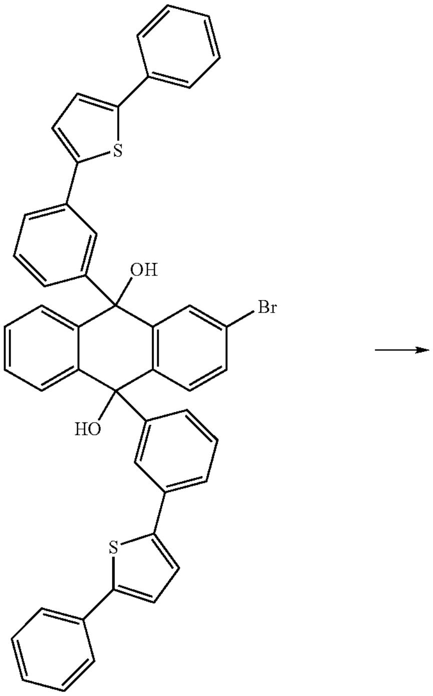

20d

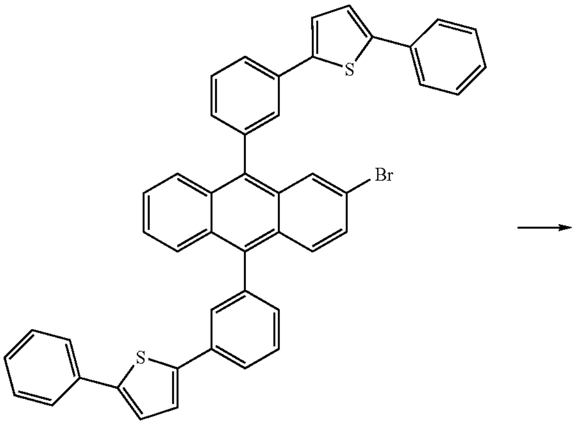

20e

-continued

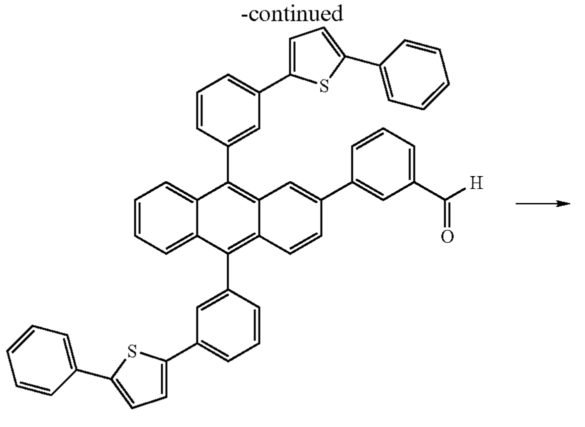

20f

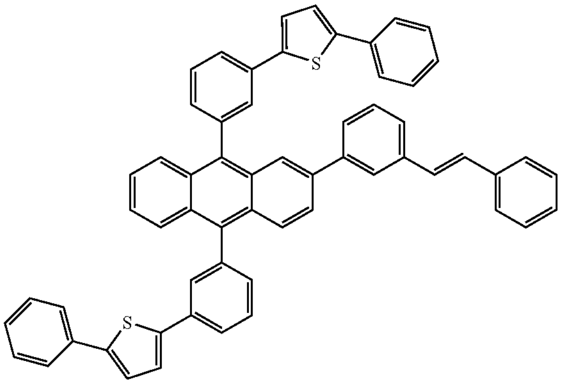

136

20-A. Synthesis of Compound 20a

The compound of 2-thiophene boronic acid (10 g, 78.1 mmol) and bromobenzene (7.48 mL, 70.3 mmol) were dissolved in anhydrous THF (300 mL), $Pd(PPh_3)_4$ (4.51 g, 3.91 mmol) and an aqueous $K_2CO_3$Solution (156 mL, 312.4 mmol) were added to the solution, and the mixture was refluxed for 3 hours. The organic phase was extracted from ethyl acetate, and moisture was removed over magnesium sulfate. The organic phase was filtered under reduced pressure, concentrated to remove the solvent, purified by column chromatography, and recrystallized from THF and ethanol to obtain a white solid compound 20a (10 g, 80%). MS [M+H] 161

20-B. Synthesis of Compound 20b

The compound 20a (5 g, 31.3 mmol) as prepared in the process of 20-A was dissolved in anhydrous THF (200 mL), and cooled to a temperature of −10° C., and n-butyl lithium (15 mL, 37.5 mmol) was slowly added dropwise to the solution. The mixture was stirred for 1 hour, and then cooled to −78° C. again. Then, boronic acid trimethylester (10.5 mL, 93.75 mmol) was slowly added thereto, and the mixture was stirred for 12 hours. The mixture was cooled to 0° C., and then an aqueous 10 wt % sulfuric acid solution (16 mL) was added thereto to obtain a white precipitate. The organic phase was extracted from THF, dried over magnesium sulfate, and then filtered under reduced pressure. This filtrate was concentrated to remove the solvent, and the residue was dissolved in THF. An excessive amount of the aqueous solution was added thereto, and the organic phase was separated with dimethylchloromethane. To the separated aqueous solution layer, an aqueous hydrochloric acid solution was added to produce a precipitate, and the precipitate was filtered to obtain a compound 20b (2.7 g, 42%).

20-C. Synthesis of Compound 20c

3-Bromoiodobenzene (3.5 g, 12.3 mmol) and the compound 20b (2.5 g, 12.3 mmol) as prepared in the process of 20-B were dissolved in anhydrous THF (100 mL), $Pd(PPh_3)_4$ (0.71 g, 0.61 mmol) was added to the solution, and then a solution obtained by dissolving $K_2CO_3$ (3.4 g, 24.6 mmol) in $H_2O$ (50 mL) was added thereto. Then, the mixture was stirred under reflux. Three hours later, the mixture washed with brine, and the organic phase was extracted from ethyl acetate. The moisture was removed over anhydrous magnesium sulfate, the residue was filtered under reduced pressure, and then concentrated. Then, the solvent was removed therefrom, and the residue was purified by column chromatography to obtain a compound 20c (2.9 g, 75%). MS [M+H]+=315.

20-D. Synthesis of Compound 20d

The compound 20c (16.7 g, 53.1 mmol) as prepared in the process of 20-C was dissolved in dried THF (100 mL), and t-butyl lithium (46.8 mL, 1.7 M pentane solution) was slowly added to the solution at −78° C., under nitrogen atmosphere. The mixture was stirred at the same temperature for 1 hour, and then the compound 17a (6.36 g, 22.0 mmol) as prepared in the process of 17-A was added thereto. The cooling vessel was removed out, and the mixture was stirred at ambient temperature for 3 hours. An aqueous ammonium chloride solution was added to the reaction mixture, and the mixture was extracted from methylene chloride. The organic phase was dried over anhydrous magnesium sulfate, and the solvent was removed. The obtained mixture was dissolved in a small amount of ethyl ether, petroleum ether was added thereto, and the mixture was stirred for several hours to obtain a solid compound. The solid compound is filtered off, the residue was dried in vacuo to obtain a compound 20d (15 g, 90%).

20-E. Synthesis of Compound 20e

The compound 20d (15.9 g, 20.5 mmol) as prepared in the process of 20-D was dispersed in acetic acid (200 mL), and to the dispersion, potassium iodide (34 g, 210 mmol), and sodium hypophosphite hydrate (37 g, 420 mmol) were added, under nitrogen atmosphere. The mixture was stirred for 3 hours under boiling. The mixture was cooled to ambient temperature, filtered, washed with water and methanol, and dried in vacuo to obtain a pale yellow compound 20e (9.5 g, 64%). MS [M+H]+=725

20-F. Synthesis of Compound 20f

A compound 20f (8 g, 81%) was obtained in the same manner as in the process of 17-D of Example 17, except that the compound 20e as prepared in the process of 20-E was used instead of the compound 17c in the process of 17-D of Example 17. MS [M+H]+=750

20-G. Synthesis of Compound 136

A compound 136 (3.0 g, 82%) was obtained in the same manner as in the process of 17-E of Example 17, except that the compound 20f as prepared in the process of 20-F was used instead of the compound 17d in the process of 17-E of Example 17. MS [M+H]+=824

Example 21
Synthesis of Compound 165
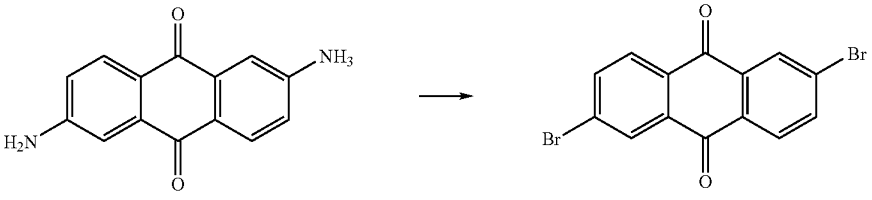
21a
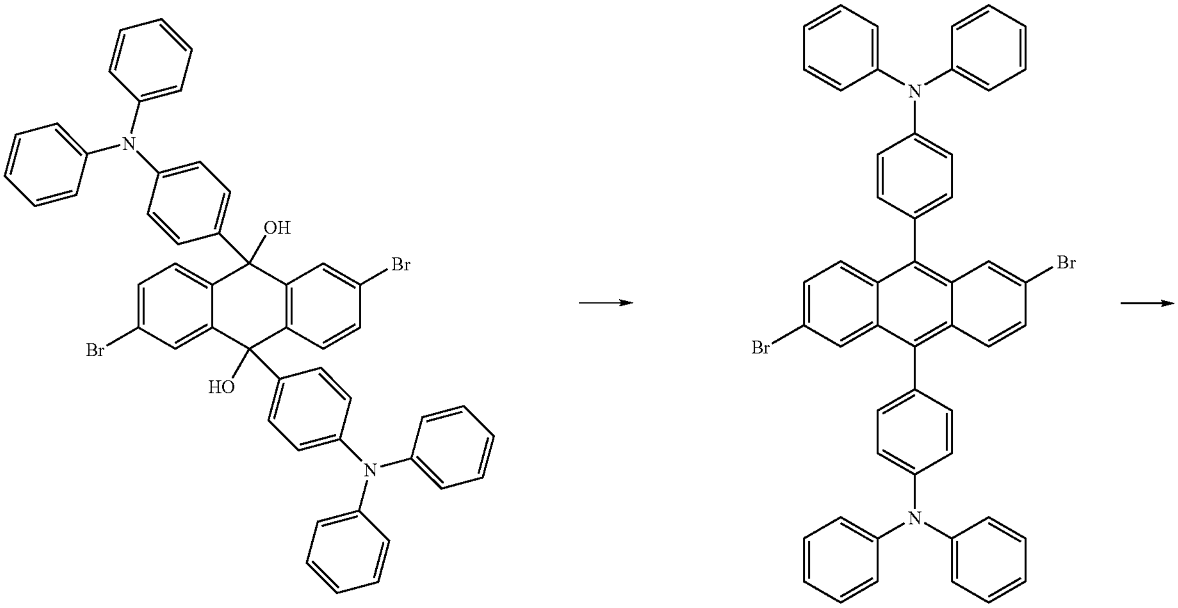
21b 21c
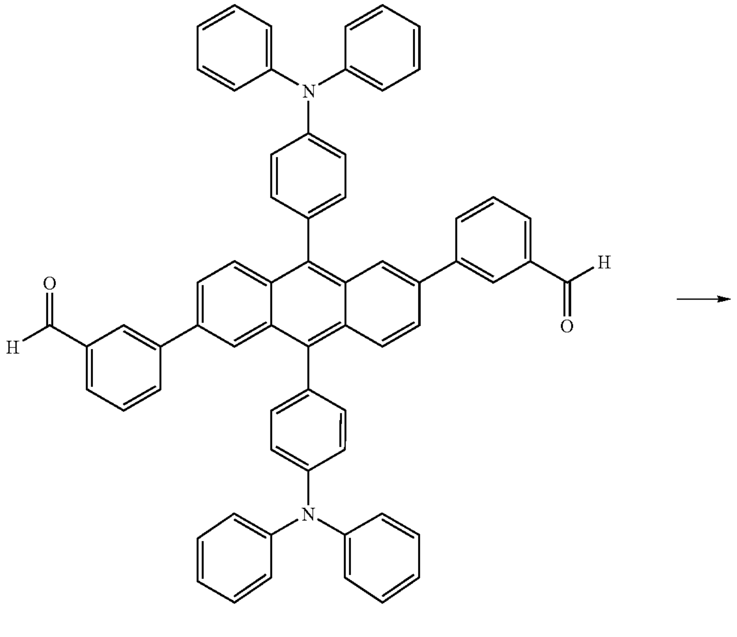
21d -continued

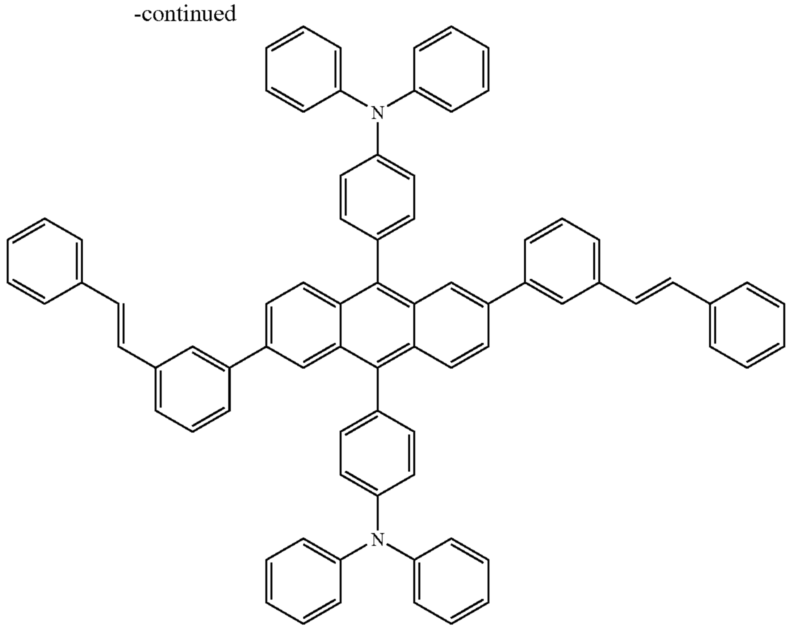

165

21-A. Synthesis of Compound 21a 2,6-diaminoanthraquinone (23.8 g, 100 mmol) was dispersed in an aqueous 48% hydrogen bromide solution, and sodium nitrite (14.1 g, 204 mmol) was slowly added to the dispersion at −20° C. After completion of gas generation, a solution obtained by dissolving copper bromide (29.5 g, 206 mmol) in the aqueous 48% hydrogen bromide solution (63 mL) was added to the dispersion, together with a small amount of ethanol (50 mL), and the reaction solution was warmed to ambient temperature, and refluxed for 1 hour. The reaction solution was cooled to ambient temperature, and water was added thereto to generate a precipitate, and the precipitate was filtered, washed with water, and dried in vacuo. The obtained product was purified by column chromatography, and then recrystallized from chloroform to obtain a pale yellow compound 21a (10 g, 27%). MS [M+H]+=366

21-B. Synthesis of Compound 21b

The compound 19a (17.2 g, 53.1 mmol) as prepared in the process of 19-A was dissolved in dried THF (100 mL), and t-butyl lithium (46.8 mL, 1.7 M pentane solution) was slowly added to the solution at −78° C., under nitrogen atmosphere. The mixture was stirred at the same temperature for 1 hour, and then the compound 21a (8.05 g, 22.0 mmol) as prepared in the process of 21-A was added thereto. The cooling vessel was removed, and the mixture was stirred at ambient temperature for 3 hours. An aqueous ammonium chloride solution was added to the reaction mixture, and the mixture was extracted from methylene chloride. The organic phase was dried over anhydrous magnesium sulfate, and the solvent was removed. The obtained mixture was dissolved in a small amount of ethyl ether, petroleum ether was added thereto, and the mixture was stirred for several hours to obtain a solid compound. The solid compound is filtered off, the residue was dried in vacuo to obtain a compound 21b (17.7 g, 94%). MS[M+H]+=856

21-C. Synthesis of Compound 21c

The compound 21b (17.5 g, 20.5 mmol) as prepared in the process of 21-B was dispersed in acetic acid (200 mL), and to the dispersion, potassium iodide (34 g, 210 mmol), and sodium hypophosphite hydrate (37 g, 420 mmol) were added, under nitrogen atmosphere. The mixture was stirred for 3 hours under boiling. The mixture was cooled to ambient temperature, filtered, washed with water and methanol, and dried in vacuo to obtain a pale yellow compound 21c (10.8 g, 64%). MS [M+H]+=822

21-D. Synthesis of Compound 21d

The compound 21c (4 g, 4.86 mmol) as prepared in the process of 21-C was dissolved in THF (150 mL), and a solution obtained by dissolving 3-formyl benzene boronic acid (1.6 g, 10.69 mmol) in EtOH (50 mL) was added thereto, under nitrogen atmosphere. To the mixture, a solution obtained by dissolving $K_2CO_3$ (3.3 g, 24.3 mmol) in $H_2O$ (100 mL), and finally $Pd(PPh_3)_4$ (0.28 g, 0.24 mmol) was added thereto, and the mixture was stirred under reflux for about 12 hours. After completion of reaction, the mixture was cooled to ambient temperature, and the organic phase was separated from the mixed reaction solution, and filtered to obtain a solid. This solid was dissolved in THF again, and purified by column chromatography. Then, the residue was recrystallized from THF and ethanol to obtain a compound 21d (3.7 g, 88%). MS [M+H]+=872

21-E. Synthesis of Compound 165

Benzylphosphoric acid diethyl ether (1.8 mL, 8.8 mmol), sodium hydride (0.38 g, 16 mmol), 18-crown-6 (0.1 g, 0.48 mmol) were added to THF (100 mL), and the compound 21d (3.5 g, 4.0 mmol) as prepared in the process of 21-D was added to the mixture at 0° C., under nitrogen atmosphere. The mixture was stirred at room temperature for about 12 hours. After completion of the reaction, THF and $H_2O$ were added to the mixed reaction solution. The organic phase was separated, dried over $MgSO_4$, and then concentrated. The residue was recrystallized from THF/EtOH to obtain a compound 165 (3.3 g, 81%). MS [M+H]+=1021

Example 22

Synthesis of Compound 174

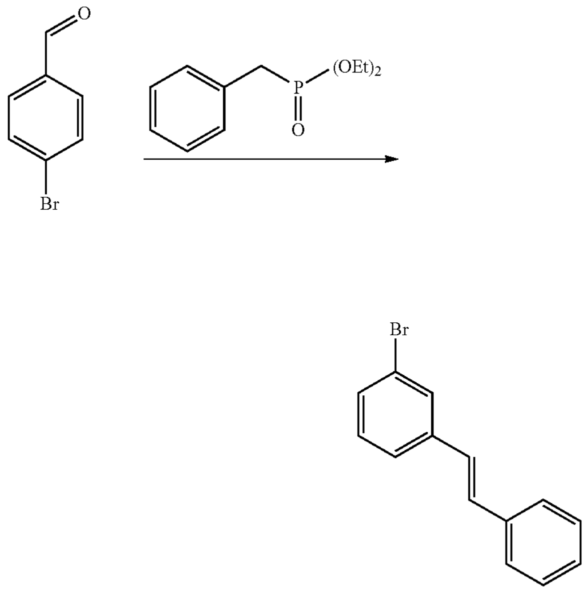

22a

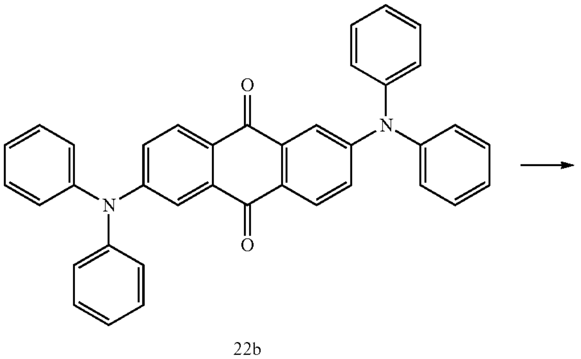

22b

-continued

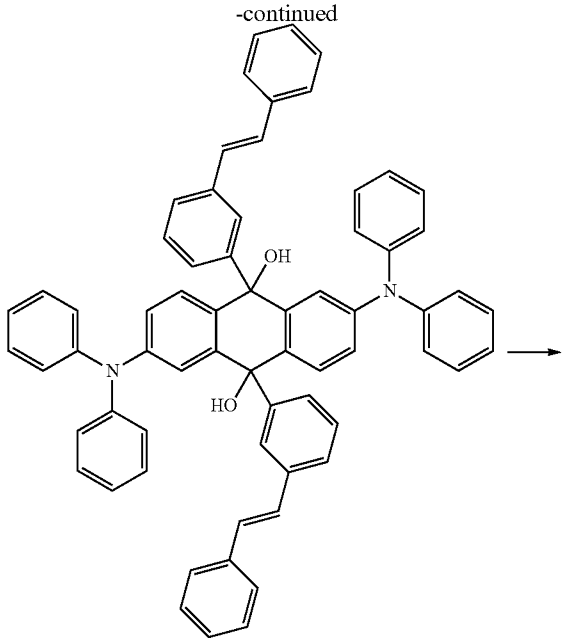

22c

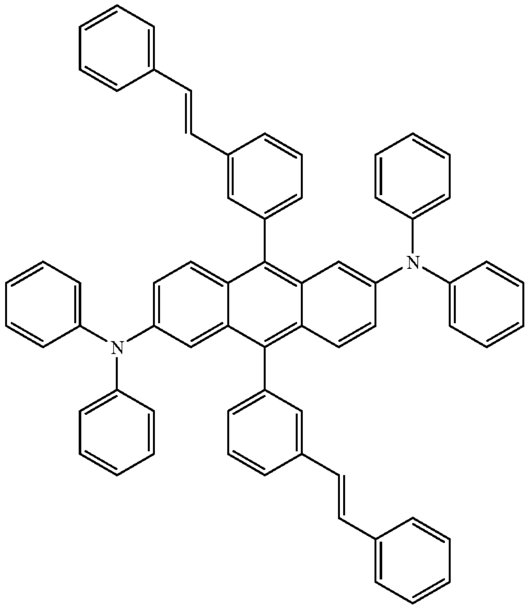

174

22-A. Synthesis of Compound 22a

NaH (3 g, 75 mmol) and 18-crown-6 (1.43 g, 5.4 mmol) were dissolved in THF (100 mL), and benzylphosphoric acid diethyl ether (13.5 mL, 65 mmol) was added to the solution. While maintaining the cooling state (0° C.), 4-bromobenzene aldehyde (10 g, 54 mmol) was slowly added thereto, and the mixture was stirred at ambient temperature for 4 hours. Water was added to the reaction solution, and the mixture was extracted from ether, dried over magnesium sulfate, and distilled off under reduced pressure. The residue was recrystallized from ethanol to obtain a compound 22a (10 g, 75%). MS [M]=295

22-B. Synthesis of Compound 22b

The compound 21a (3.1 g, 8.5 mmol), diphenylamine (6.02 g, 20.4 mmol), pd(dba)$_2$ (0.097 g, 0.17 mmol), P(t-Bu)$_3$ (0.05 g, 0.255 mmol), and sodium t-butoxide (2.45 g, 25.5 mmol)

were added to toluene (100 mL), and the mixture was refluxed for about 2 hours. After completion of the reaction, the mixture was cooled to ambient temperature, and the mixed reaction solution was added to a mixture of THF and $H_2O$. The organic phase was separated, dried over $MgSO_4$, and then concentrated. The residue was purified by column chromatography to obtain a compound 22b (3.0 g, 65%). MS [M+H]+=542

22-C. Synthesis of Compound 22c

The compound 22a (3.9 g, 13.2 mmol) as prepared in the process of 22-A was dissolved in dried THF (100 mL), and t-butyl lithium (11.7 mL, 1.7 M pentane solution) was slowly added to the solution at −78° C., under nitrogen atmosphere. The mixture was stirred at the same temperature for 1 hour, and then the compound 22b (3 g, 5.5 mmol) as prepared in the process of 22-B was added thereto. The cooling vessel was removed, and the mixture was stirred at ambient temperature for 3 hours. An aqueous ammonium chloride solution was added to the reaction mixture, and the mixture was extracted from methylene chloride. An organic phase was dried over anhydrous magnesium sulfate, and the solvent was removed. The obtained mixture was dissolved in a small amount of ethyl ether, petroleum ether was added thereto, and the mixture was stirred for several hours to obtain a solid compound. The solid compound is filtered off, the residue was dried in vacuo to obtain a compound 22c (4.2 g, 85%).

22-D. Synthesis of Compound 174

The compound 22c (4.2 g, 5.6 mmol) as prepared in the process of 22-C was dispersed in acetic acid (50 mL), and to the dispersion, potassium iodide (9.4 g, 57.4 mmol), and sodium hypophosphite hydrate (10 g, 115 mmol) were added, under nitrogen atmosphere. The mixture was stirred for 3 hours under boiling. The mixture was cooled to ambient temperature, filtered, washed with water and methanol, and dried in vacuo to obtain a pale yellow compound 174 (3.2 g, 65%). MS [M+H]+=868

Example 23

Synthesis of Compound 59

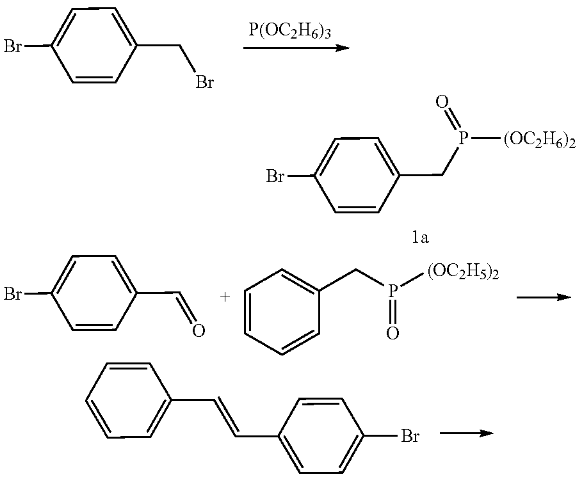

1a

1b

-continued

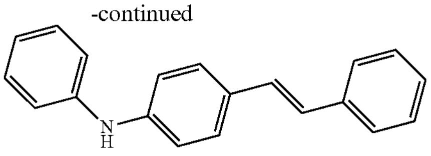

1c

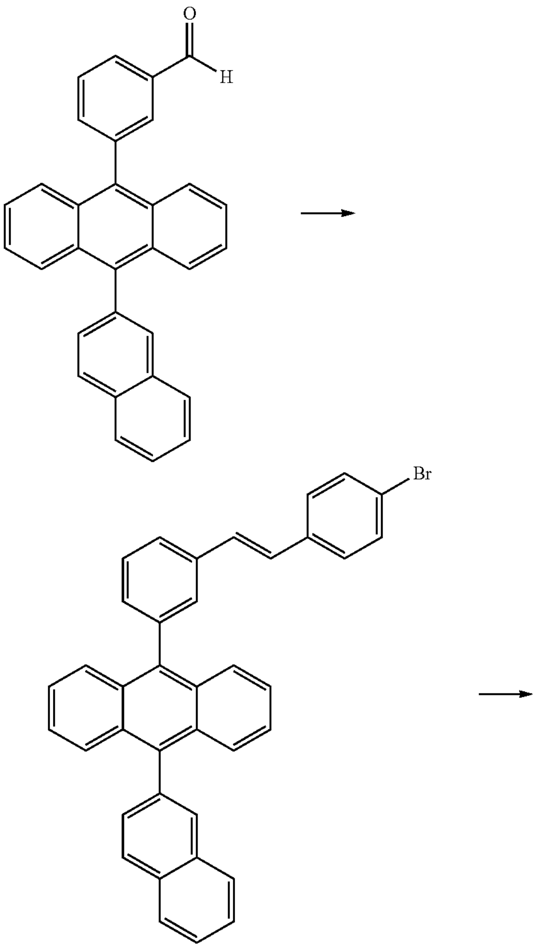

d

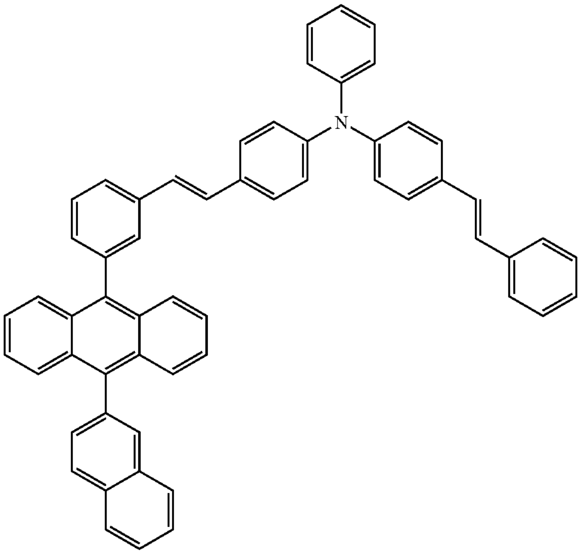

059

23-A. Synthesis of Compound 23a

4-Bromobenzyl bromide (20 g, 76 mmol) was added to triethyl phosphite (50 mL, 0.29 mol) under $N_2$, and the mixture was stirred under reflux for 12 hours. The reactant was cooled to ambient temperature, and distilled under reduced pressure obtain a compound 23a (22 g, 98%) in the liquid form.

23-B. Synthesis of Compound 23b

Sodium hydride (3 g, 75 mmol), 18-crown-6 (1.43 g, 5.4 mmol) were added to THF (100 mL), and then benzylphosphoric acid diethyl ether (13.5 mL, 64.8 mmol) was added to the mixture, under $N_2$. 4-Bromobenzaldehyde (10 g, 54 mmol) was added to the mixture at 0° C. The mixture was stirred at room temperature for about 12 hours. After completion of the reaction, THF and $H_2O$ were added to the mixed reaction solution. The organic phase was separated, dried over $MgSO_4$, and then and concentrated. The residue was recrystallized from THF/EtOH to obtain a compound 23b (10.5 g, 75%). MS [M+H]+=259

23-C. Synthesis of Compound 23c

The compound 23b (3.68 g, 14 mmol) as prepared in the process of 23-B, aniline (1.5 ml, 16.8 mmol), pd(dba)$_2$ (0.125 g, 0.13 mmol), P(t-Bu)$_3$ (0.04 g, 0.2. mmol), and sodium t-butoxide (1.80 g, 18.7 mmol) were added to toluene (50 mL) under nitrogen atmosphere, and the mixture was refluxed for about 3 hours. After completion of the reaction, the mixture was cooled to ambient temperature, and the mixed reaction solution was added to a mixture of THF and $H_2O$. The organic phase was separated, dried over magnesium sulfate, and then concentrated. The residue was purified by column chromatography to obtain a compound 23c (2.2 g, 58%). MS [M+H]+=271

23-D. Synthesis of Compound 23d

Sodium hydride (0.78 g, 19.4 mmol), and 18-crown-6 (0.26 g, 0.97 mmol) were added to THF (100 mL), and the compound 23a (6 g, 19.4 mmol) as prepared in the process of 23-A was added to the mixture, under $N_2$. The compound 1a (4 g, 9.7 mmol) as prepared in the process of 1-A was added to the mixture at 0° C. The mixture was stirred at room temperature for about 12 hours. After completion of the reaction, THF and $H_2O$ were added to the mixed reaction solution. The organic phase was separated, dried over $MgSO_4$, and then and concentrated. The residue was recrystallized from THF/EtOH to obtain a compound 23d (5.2 g, 96%). MS [M+H]+=561

23-E. Synthesis of Compound 59

The compound 23d (2 g, 3.5 mmol) as prepared in the process of 23-D, the compound 23c (1.22 g, 4.5 mmol) as prepared in the process of 23-C, pd(dba)$_2$ (40.6 mg, 0.033 mmol), P(t-Bu)$_3$ (28.8 mg, 0.033 mmol), and sodium t-butoxide (0.84 g, 8.75 mmol) were added to toluene (120 mL) under nitrogen atmosphere, and the mixture was refluxed for about 12 hours. After completion of the reaction, the mixture was cooled to ambient temperature, and the mixed reaction solution was added to a mixed solution of THF and $H_2O$. The organic phase was separated, dried over magnesium sulfate, and then concentrated. The residue was purified by column chromatography to obtain a compound 59 (2 g, 76%). MS [M+H]+=751

Example 24

Synthesis of Compound 143

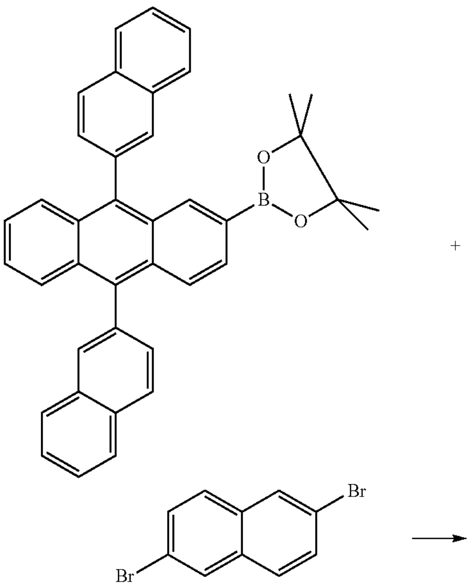

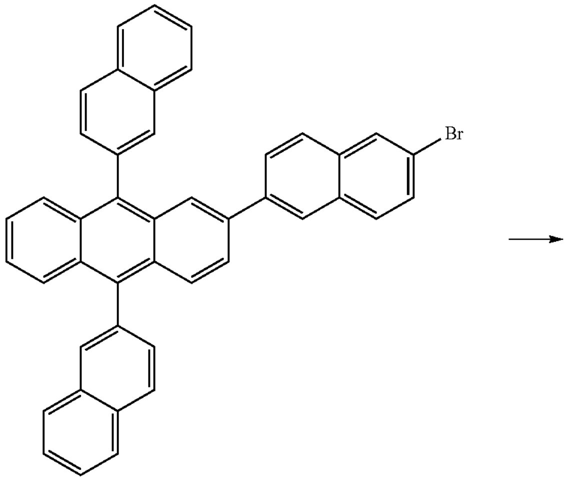

24a

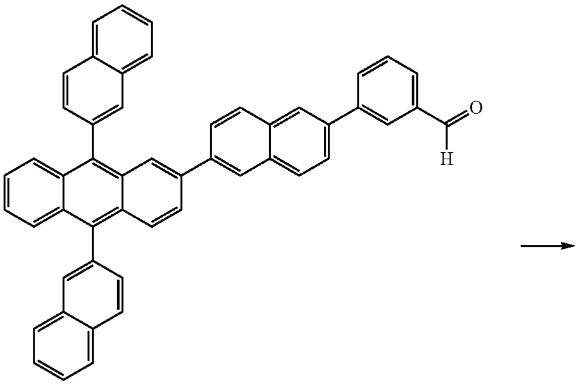

24b

-continued

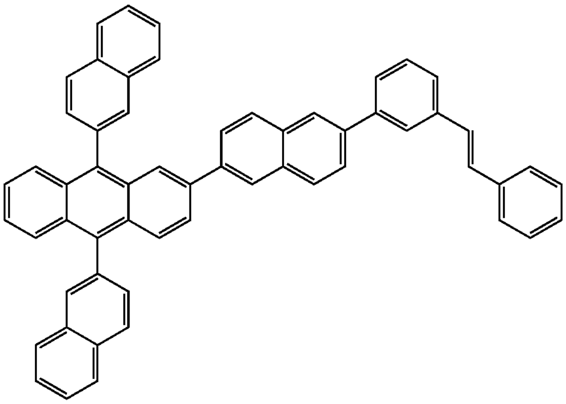

143

24-A. Synthesis of Compound 24a

The compound 18d (4.7 g, 8.5 mmol) as prepared in the process of 18-D and 2,6-dibromo naphthalene (2.4 g, 8.5 mmol) were dissolved in THF (120 mL) under nitrogen atmosphere. To the mixture, a 2M $K_2CO_3$ solution (60 mL) was added, finally $Pd(PPh_3)_4$ (0.23 g, 0.3 mmol) was added thereto, and the mixture was stirred under reflux for about 12 hours. After completion of the reaction, the mixture was cooled to ambient temperature, the organic phase was separated from the mixed reaction solution, and removed. And the residue was purified by column chromatography to obtain a compound 24a (3.9 g, 45%). MS [M+H]+=556

24-B. Synthesis of Compound 24b

A compound 24b (8 g, 81%) was obtained in the same manner as in the process of 17-D of Example 17, except that the compound 24a as prepared in the process of 24-A was used instead of the compound 17c in the process of 17-D of Example 17. MS [M+H]+=635

24-C. Synthesis of Compound 143

A compound 143 (3.0 g, 82%) was obtained in the same manner as in the process of 17-E of Example 17, except that the compound 24b as prepared in the process of 24-B was used instead of the compound 17d in the process of 17-E of Example 17. MS [M+H]+=660

Example 25

Synthesis of Compound 195

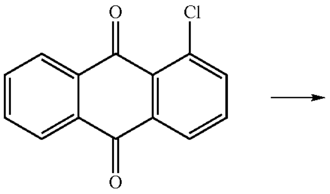

-continued

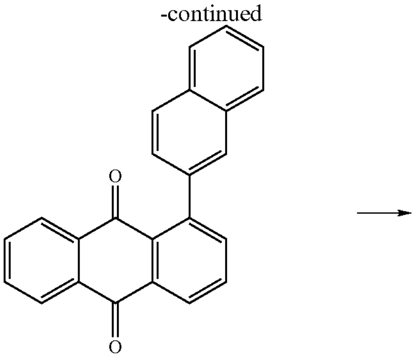

25a

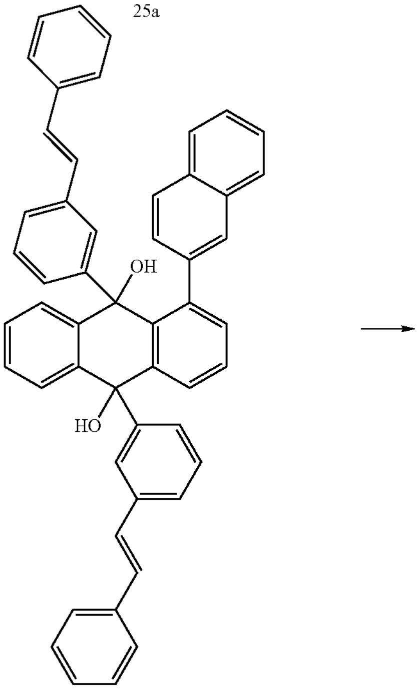

25b

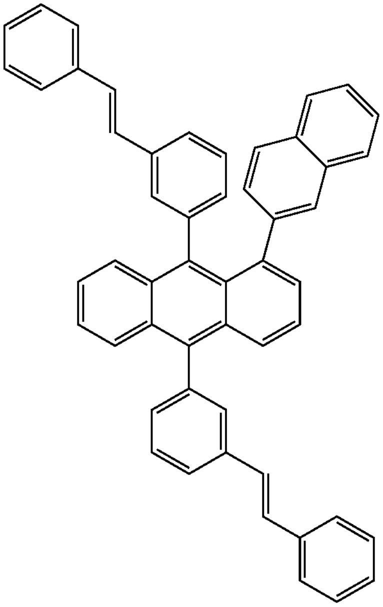

25c

25-A. Synthesis of Compound 25a 1-chloro anthraquinone (41.2 mmol, 10.0 g) was completely dissolved in THF (200 mL), and 2-naphthalene boronic acid (45.3 mmol, 7.80 g), 2M potassium carbonate solution (50 mL) and tetrakis(triphenylphosphine) palladium (0) (1.24 mmol, 1.43 g) were added thereto, and the mixture was refluxed for 19 hours. After completion of reaction, the mixture cooled to ambient temperature, filtered, and washed several times with water and ethanol to obtain a compound 25a (13.2 g, 96%). MS [M]=334

25-B Synthesis of Compound 25b

The compound 22a (20.4 mmol, 4.23 g) as prepared in the process of 22-A was dissolved completely in dried THF (100 mL), and n-butyl lithium (8.2 ml, 2.5 M hexane solution) was very slowly added to the solution at −78° C. After an hour, the compound 25a (8.17 mmol, 2.73 g) as prepared in the process of 25-A was added to the above mixture. After 30 minutes, the cooling vessel was removed out, and the mixture was subject to reaction at ambient temperature for 3 hours. After completion of the reaction, an aqueous $NH_4Cl$ solution was added thereto and reactant was extracted from ethyl ether. The extracted reactant was dried over $MgSO_4$, and then concentrated. To the extracted reactant, a small amount of ethyl ether was added, and the mixture was stirred. And then ethanol was added, the mixture was stirred. Thereafter, after filtering and drying the reactant, a dialcohol compound 25b (4.58 g, 95%) was obtained. MS [M]=676 (—$H_2O$ form)

25-C Synthesis of Compound 195

The compound 25b (4.7 g, 6.77 mmol), potassium iodide (1.12 g, 6.77 mmol) and sodium hypophosphite (7.18 g, 67.7 mmol) were added to acetic acid (100 mL), and the mixture was refluxed for 3 hours. The above reactant cooled to ambient temperature, filtered, washed several times with water and ethanol, and then dried to obtain a compound 195 (2.77 g, 62%). MS [M]=660

Example 26

Synthesis of Compound 212

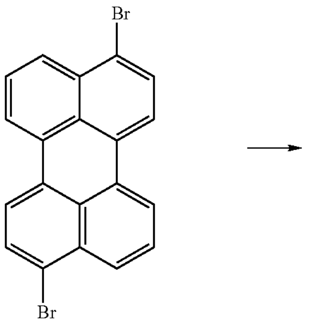

-continued

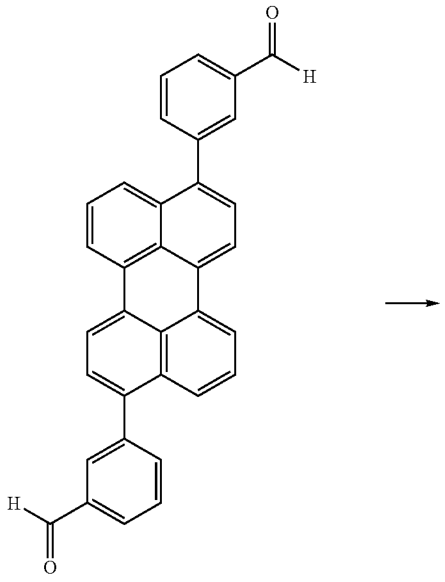

26a

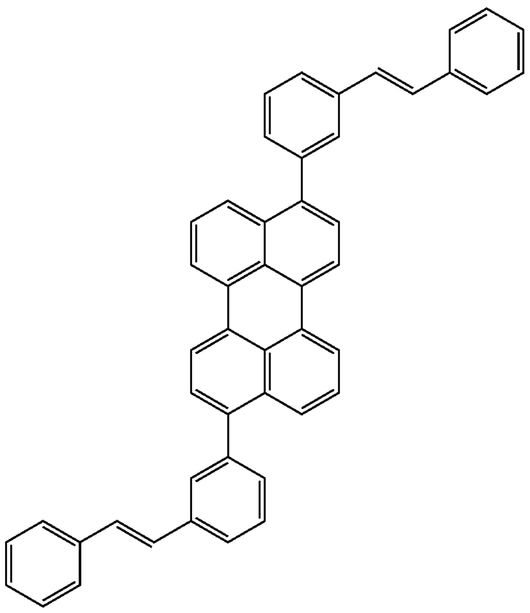

212

26-A Synthesis of Compound 26a 3,9-bromo phenylene (2 g, 4.86 mmol) was dissolved in THF (120 mL), and a solution obtained by dissolving 3-formyl benzene boronic acid (1.6 g, 10.69 mmol) in EtOH (50 mL) was added thereto, under nitrogen atmosphere. To the mixture, a solution obtained by dissolving $K_2CO_3$ (3.3 g, 24.3 mmol) in $H_2O$ (100 mL), and finally $Pd(PPh_3)_4$ (0.28 g, 0.24 mmol) was added thereto, and then the mixture was stirred under reflux for about 12 hours. After completion of reaction, the mixture was cooled to ambient temperature, and the organic phase was separated from the mixed reaction solution, and filtered to obtain a solid. This solid was dissolved in THF again, and purified by column chromatography. Then, the residue was recrystallized from THF and ethanol to obtain a compound 26a (1.9 g, 85%). MS [M+H]+=460

26-B Synthesis of Compound 212

Benzilphosphoric acid diethyl ether (1.8 mL, 8.8 mmol), sodium hydride (0.38 g, 16 mmol) and 18-crown-6 (0.1 g, 0.48 mmol) were added to THF (100 mL), and the compound 26a (1.8 g, 4.0 mmol) as prepared in the process of 26-A was added to the mixture at 0° C., under nitrogen atmosphere. The mixture was stirred at room temperature for about 12 hours. After completion of the reaction, THF and $H_2O$ were added to the mixed reaction solution. The organic phase was separated, dried over $MgSO_4$, and then concentrated. The residue was recrystallized from THF/EtOH to obtain a compound 212 (1.97 g, 81%). MS [M+H]+=608

Experimental Example 1

A glass substrate (Corning 7059 glass) on which a thin film of ITO (indium tin oxide) was coated to a thickness of 1000 Å was immersed in distilled water having a detergent dissolved therein, and the substrate washed with ultrasonic waves. The detergent was a product commercially available from Fisher Co. and the distilled water has been filtered previously by using a filter commercially available from Millipore Co. ITO washed with ultrasonic waves for 30 minutes, and then such washing was repeated twice for 10 minutes by using distilled water. After the completion of washing with distilled water, washing with ultrasonic waves was carried out by using isopropyl alcohol, acetone and methanol as the solvents in this order. The resultant product was dried.

On the ITO electrode thus prepared, 3,6-bis-2-naphthylphenylamino-N-[4-(2-naphthylphenyl)aminophenyl]carbazole (800 Å), 4,4'-bis[N-(1-naphthyl)-N-phenylamino]biphenyl(NPB) (300 Å), host materials as in the following Tables 7 and 8 (300 Å), and 9,10-bis-2-naphthyl-2-[4-(N-phenylbenzoimidazoyl)phenyl]anthracene (300 Å) were sequentially subject to thermal vacuum deposition, thereby forming a hole injecting layer, a hole transporting layer, a light emitting layer and an electron transporting layer in this order. As the material for the dopant in the light emitting layer, styrylamine compound (D1) and the compound 59 in Table 1 were used.

On the electron transporting layer, lithium fluoride (LiF) and aluminum were sequentially vacuum-deposited to a thickness of 12 Å and 2000 Å, respectively, to form a cathode. Thus, an organic light emitting diode was produced.

In the above process, deposition rate of each organic material was maintained at 0.4 to 0.7 Å/sec and deposition rates of lithium fluoride and aluminum of the cathode were maintained at 0.3 Å/sec and 2 Å/sec, respectively.

The vacuum degree during deposition was maintained at $2\times10^{-7}$ to $5\times10^{-8}$ torr.

(D1)

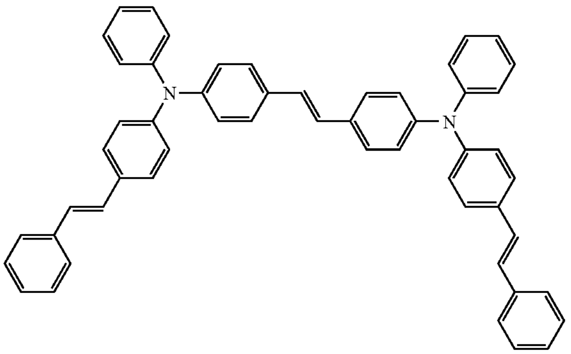

As currents were applied to the above-prepared device, the results in the following Tables 7 and 8 were obtained.

TABLE 7

| Experimental Ex. | Host material | Dopant material | Doping conc. (wt %) | Voltage (V) | Current efficiency (cd/A) | Luminous efficiency (lm/W) | Color coordinate (x, y) |
|---|---|---|---|---|---|---|---|
| 1-1 | Compound 1 | D1 | 8 | 8.5 | 5.4 | 2.0 | (0.140, 0.156) |
| 1-2 | Compound 1 | Compound 59 | 8 | 8.9 | 3.4 | 1.2 | (0.148, 0.118) |
| 1-3 | Compound 1 | Compound 59 | 10 | 8.8 | 3.7 | 1.3 | (0.148, 0.122) |
| 1-4 | Compound 1 | Compound 50 | 4 | 7.9 | 18.1 | 7.2 | (0.309, 0.638) |
| 1-5 | Compound 2 | D1 | 8 | 8.9 | 5.6 | 2.0 | (0.139, 0.149) |
| 1-6 | Compound 2 | Compound 59 | 10 | 8.8 | 3.9 | 1.4 | (0.147, 0.118) |
| 1-7 | Compound 5 | Compound 59 | 8 | 7.8 | 2.8 | 1.1 | (0.149, 0.120) |
| 1-8 | Compound 11 | Compound 59 | 8 | 7.9 | 3.1 | 1.3 | (0.148, 0.124) |
| 1-9 | Compound 12 | Compound 59 | 8 | 7.8 | 3.5 | 1.5 | (0.148, 0.120) |
| 1-10 | Compound 65 | D1 | 8 | 8.9 | 5.3 | 1.9 | (0.149, 0.226) |
| 1-11 | Compound 90 | Compound 59 | 10 | 8.5 | 3.8 | 1.4 | (0.147, 0.119) |
| 1-12 | Compound 50 | Compound 59 | 8 | 7.8 | 3.2 | 1.3 | (0.150, 0.132) |
| 1-13 | Comp. Compound 1 | Compound 59 | 8 | 8.8 | 2.5 | 0.9 | (0.150, 0.126) |

TABLE 7-continued

| Experimental Ex. | Host material | Dopant material | Doping conc. (wt %) | Voltage (V) | Current efficiency (cd/A) | Luminous efficiency (lm/W) | Color coordinate (x, y) |
|---|---|---|---|---|---|---|---|

[Comparative Compound 1]

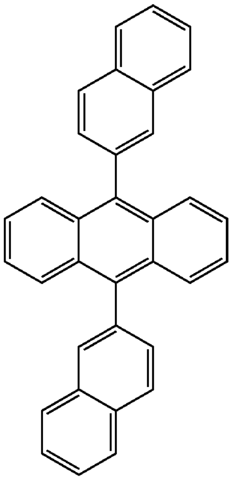

The values shown in the above Table 7 were those as measured at a current density of 100 mA/$cm^2$.

TABLE 8

| Experimental Ex. | Host material | Dopant material | Doping conc. (wt %) | Voltage (V) | Current efficiency (cd/A) | Luminous efficiency (lm/W) | Color Coordinate (x, y) | Lifetime ($T_{80}$) @ 50 mA/$cm^2$ |
|---|---|---|---|---|---|---|---|---|
| 1-14 | Compound 124 | Compound 174 | 4% | 7.45 | 19.6 | 8.25 | (0.316, 0.639) | 210 h |
| 1-15 | Compound 125 | Compound 174 | 4% | 7.55 | 20.5 | 8.52 | (0.322, 0.636) | 200 h |
| 1-16 | Compound 136 | Compound 174 | 4% | 7.62 | 18.5 | 7.63 | (0.311, 0.643) | 245 h |
| 1-17 | Comp. compound 2 | Compound 174 | 4% | 7.66 | 18.3 | 7.51 | (0.321, 0.636) | 95 h |

[Comparative Compound 2]

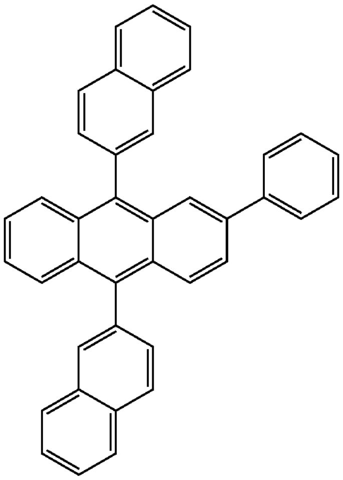

Experimental Example 2

The same procedure as in Experimental Example 1 was carried out, except that as the material for a hole injecting layer, hexanitrile hexaazatriphenylene was used instead of 3,6-bis-2-naphthylphenylamino-N-[4-(2-naphthylphenyl) aminophenyl]carbazole, and as the materials for a light emitting host dopant, the materials shown in the following Table 9 were used. The results are shown in the following Table 9.

TABLE 9

| Experimental Ex. | Host material | Dopant material | Doping conc. (wt %) | Voltage (V) | Current efficiency (cd/A) | Luminous efficiency (lm/W) | Color Coordinate (x, y) | Lifetime ($T_{80}$) @50 mA/cm$^2$ |
|---|---|---|---|---|---|---|---|---|
| 1-18 | Compound 124 | Compound 174 | 4% | 6.76 | 18.2 | 8.45 | (0.319, 0.639) | 520 h |
| 1-19 | Compound 125 | Compound 174 | 4% | 6.77 | 18.3 | 8.48 | (0.320, 0.637) | 550 h |
| 1-20 | Compound 136 | Compound 174 | 4% | 6.84 | 17.0 | 7.79 | (0.308, 0.642) | 450 h |
| 1-21 | Comp. compound 2 | Compound 174 | 4% | 6.91 | 17.4 | 7.92 | (0.323, 0.633) | 190 h |

The invention claimed is:

1. A compound selected from the group consisting of:

124

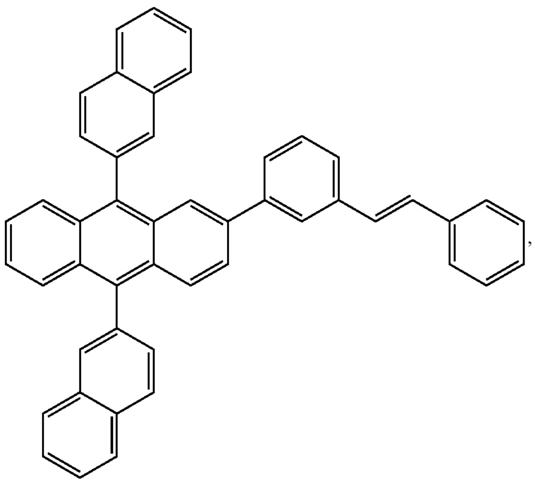

,

125

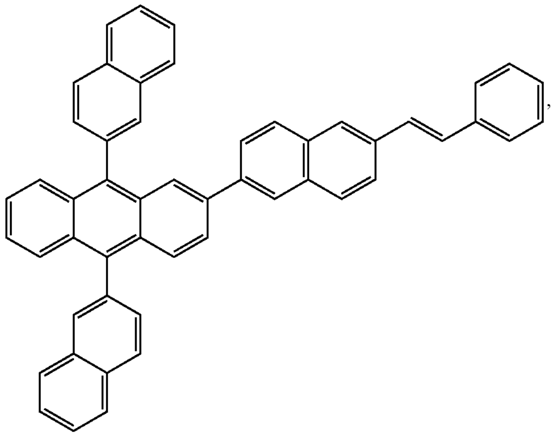

,

-continued

126

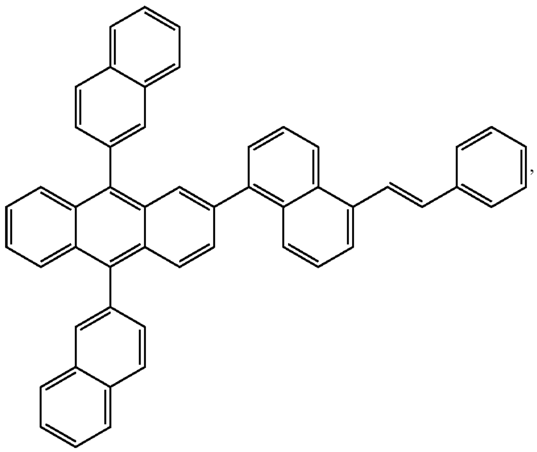

,

127

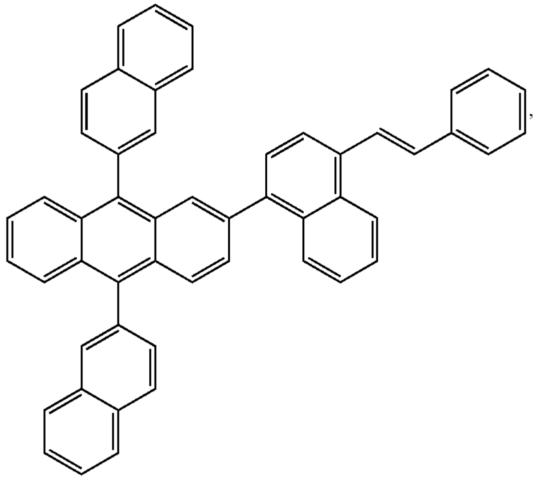

,

128
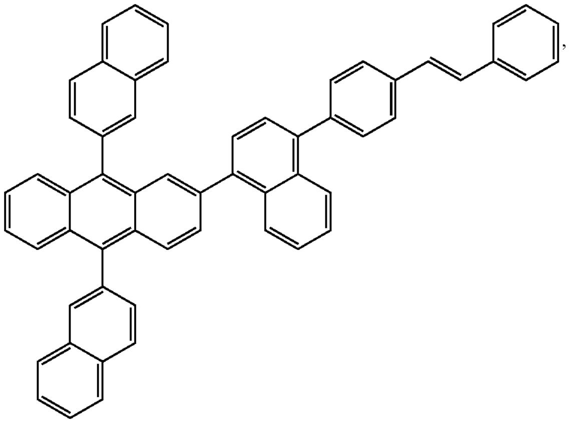
,
129
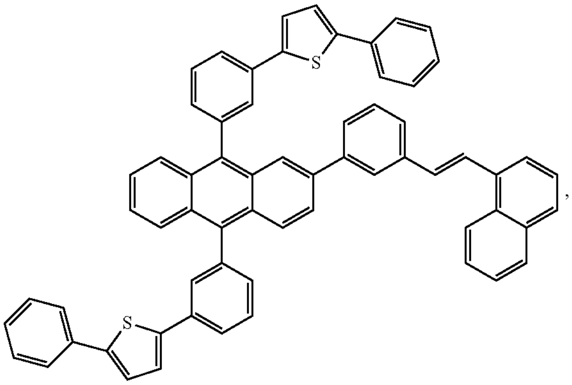
,
130
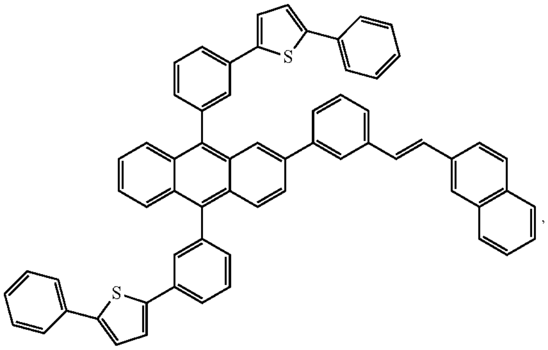
,
131
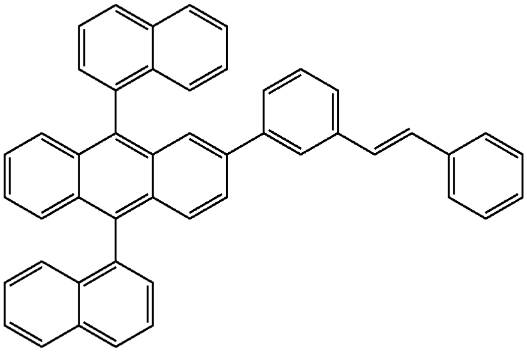
132
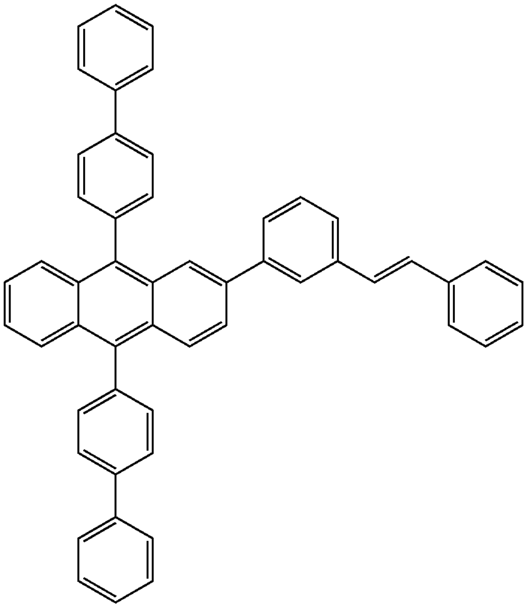
133
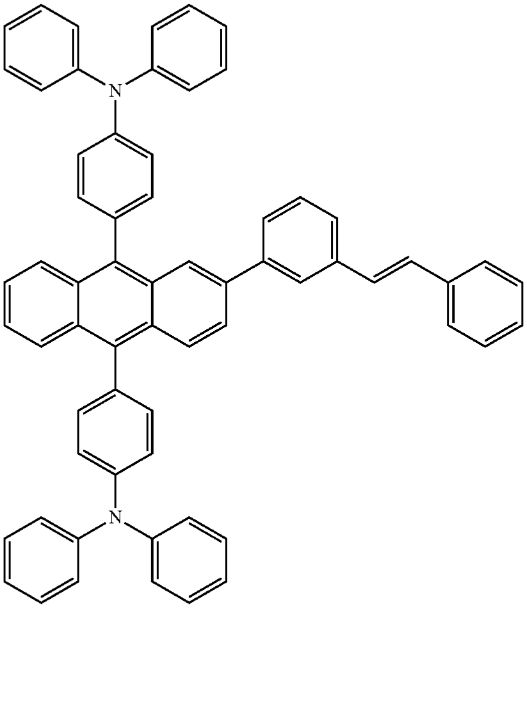
, -continued
134
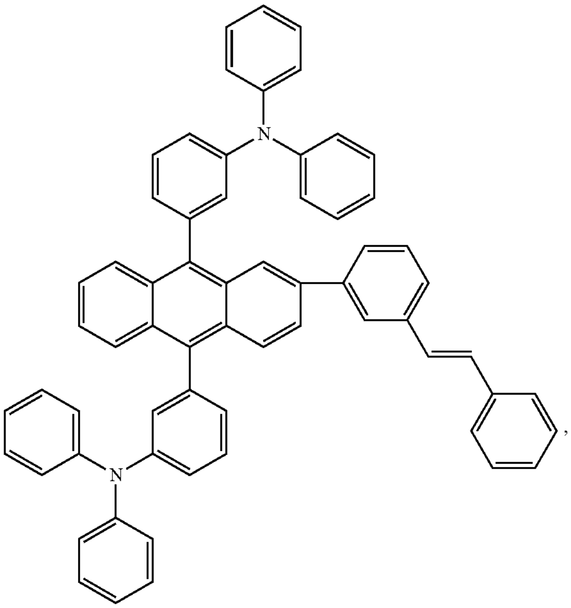
,
135
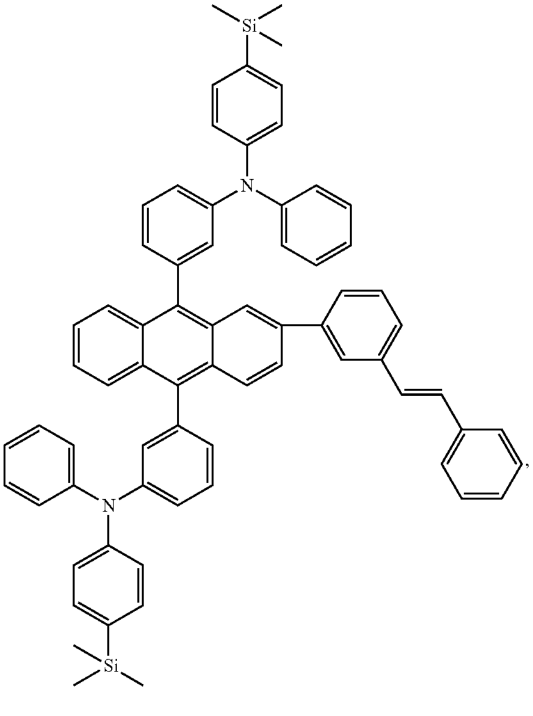
,
-continued
136
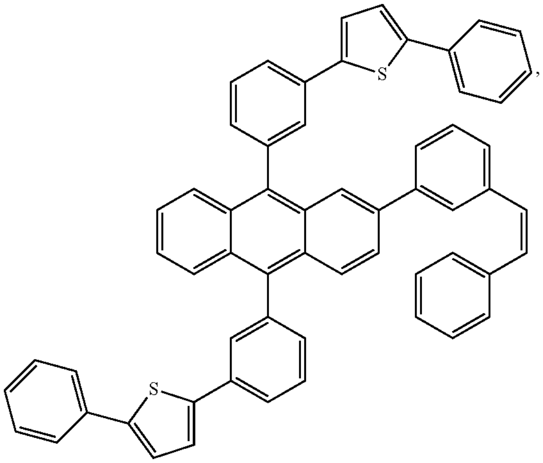
,
137
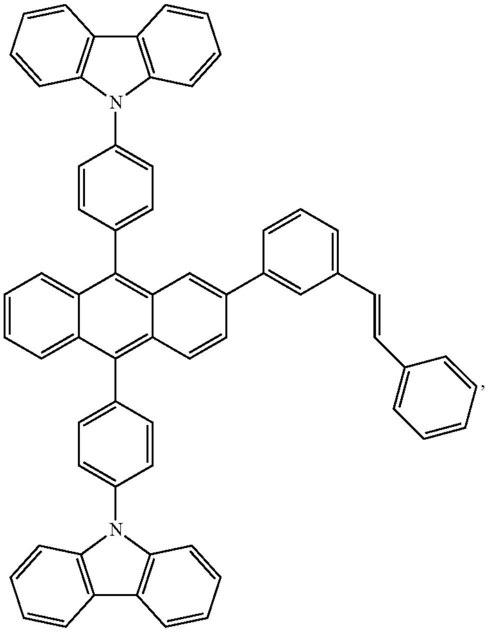
, -continued
138
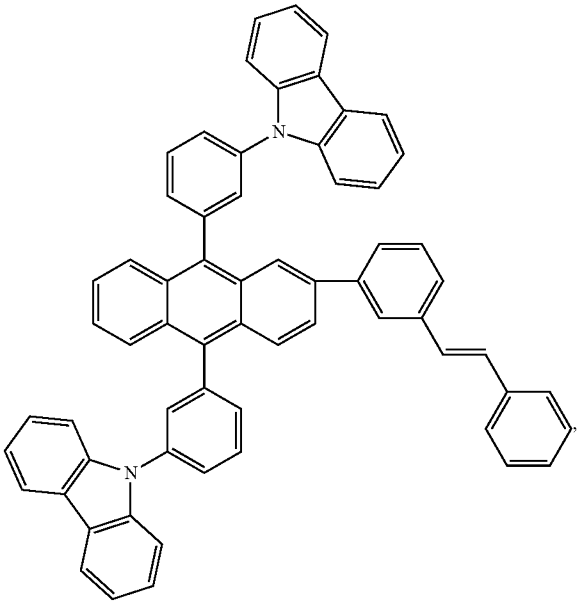
,
139
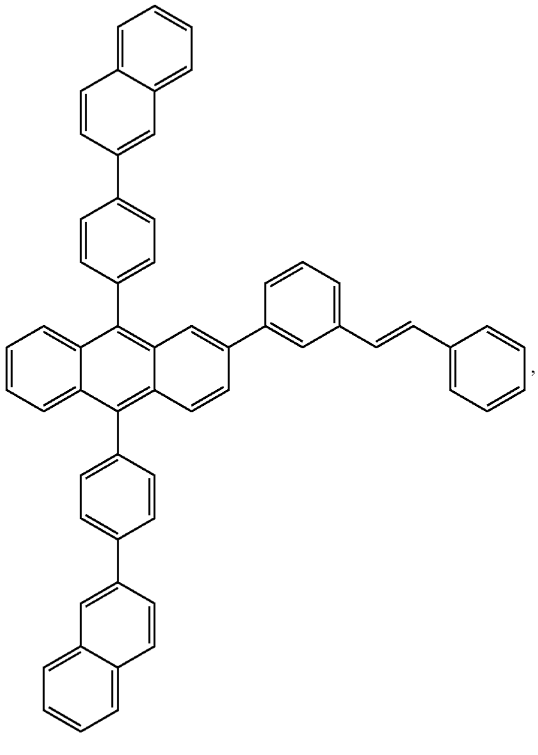
,
-continued
140
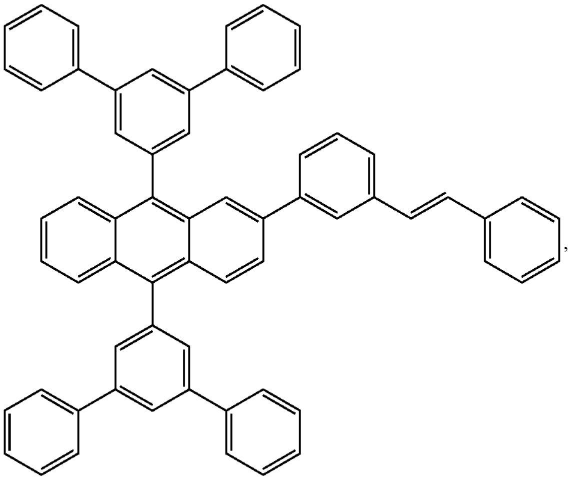
,
141
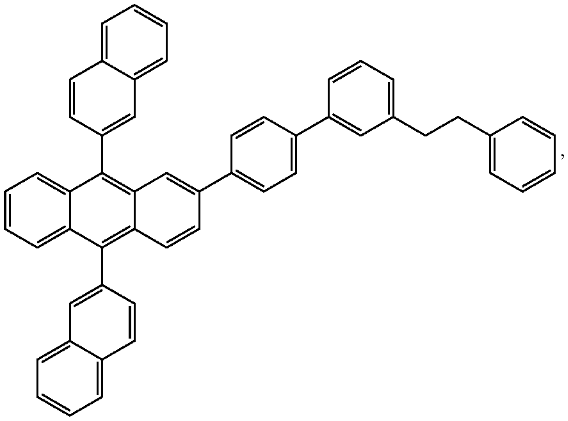
,
142
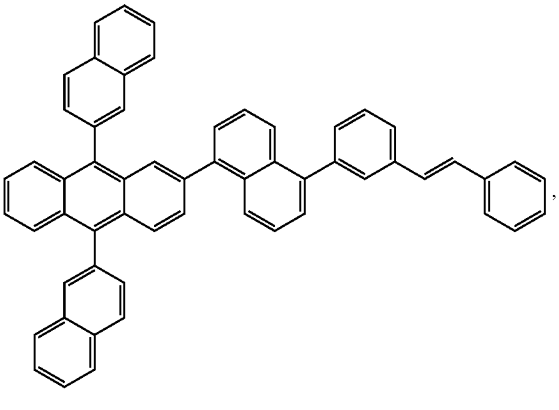
, -continued
143
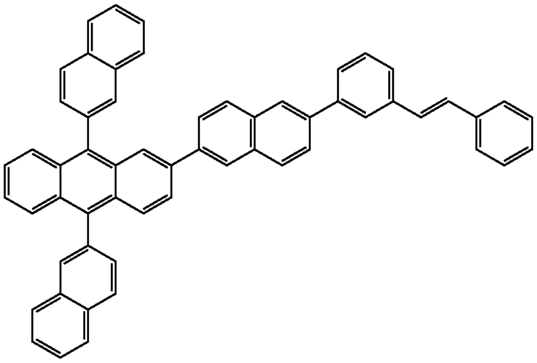
,
144
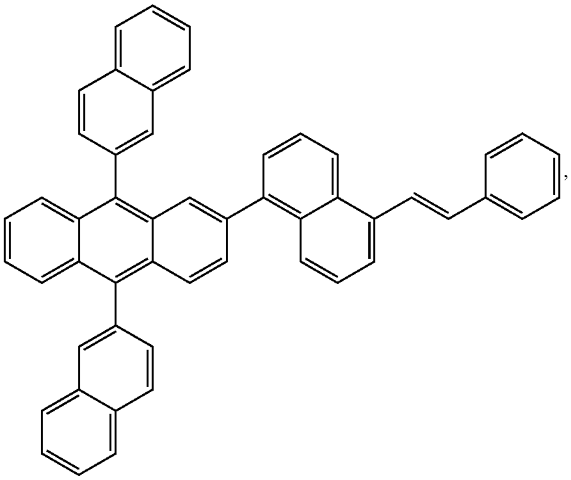
,
145
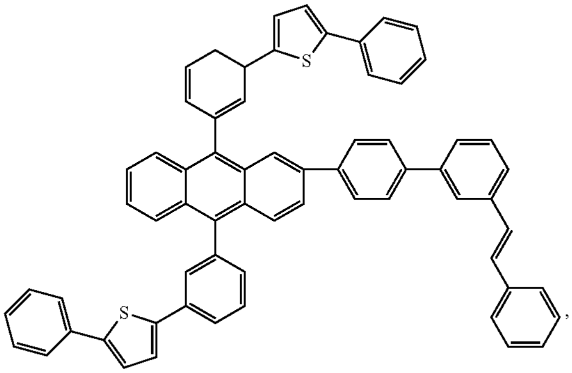
,
-continued
146
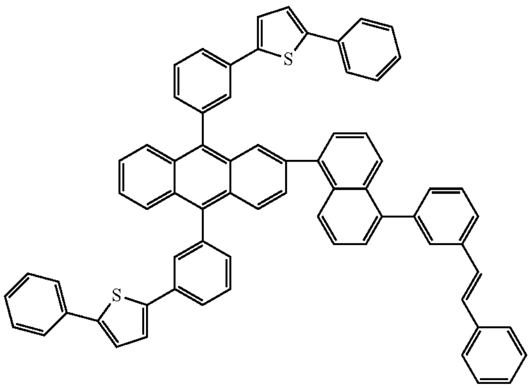
,
147
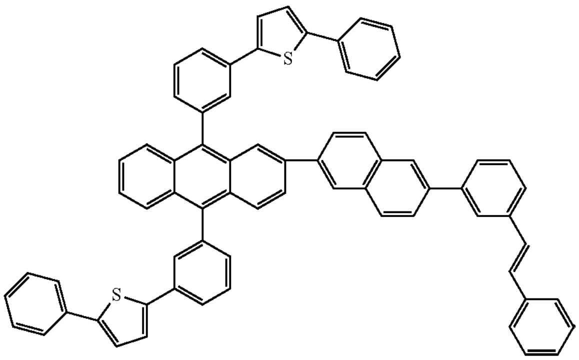
148
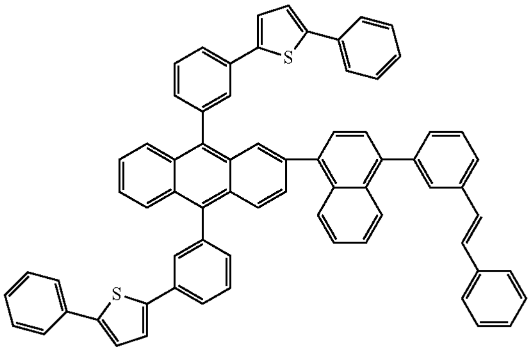
,
149
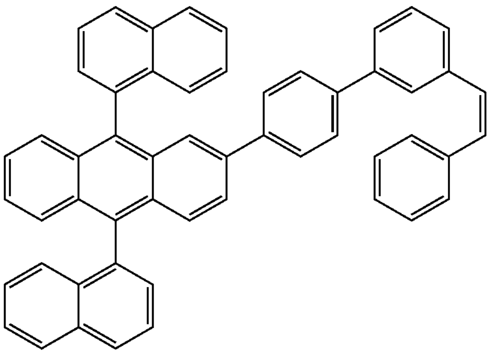
, -continued
150
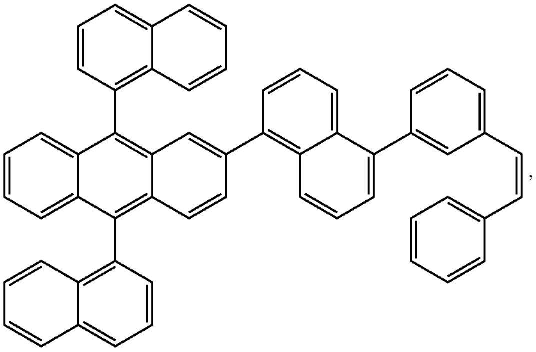
,
151
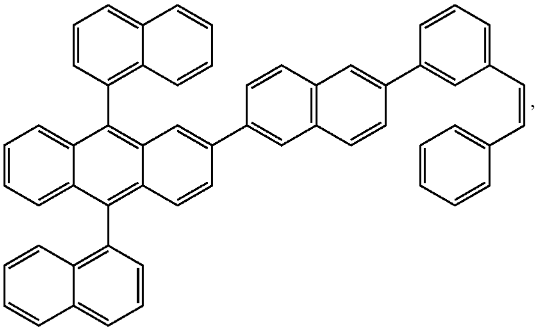
,
152
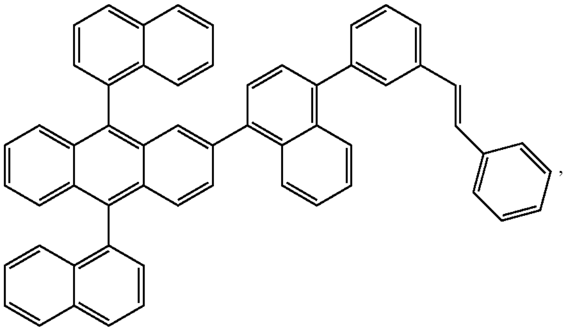
,
-continued
153
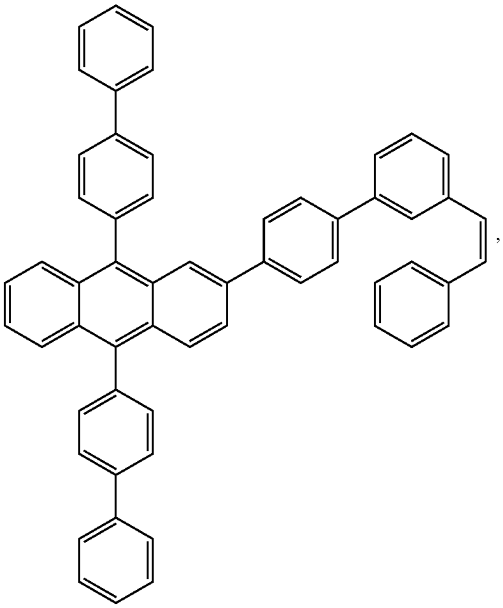
,
154
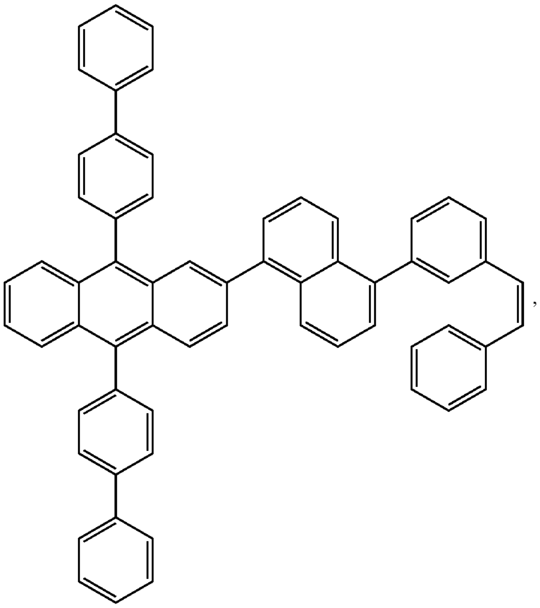
, -continued
155
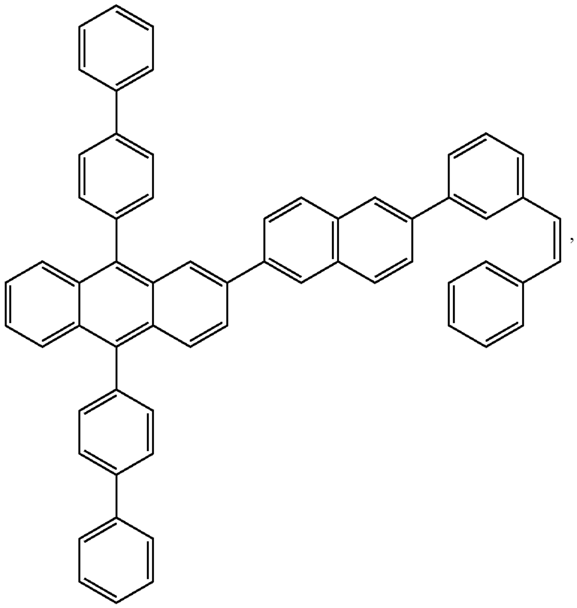
,
157
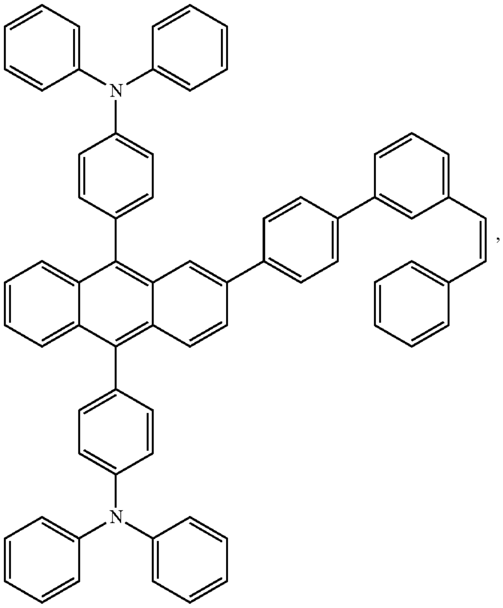
,
156
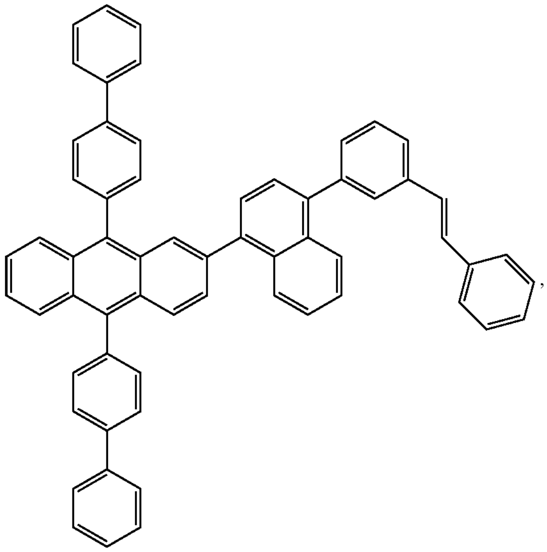
,
158
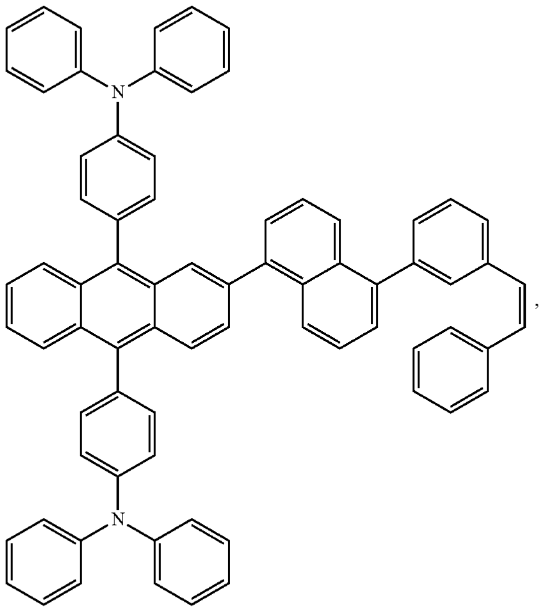
, -continued
159
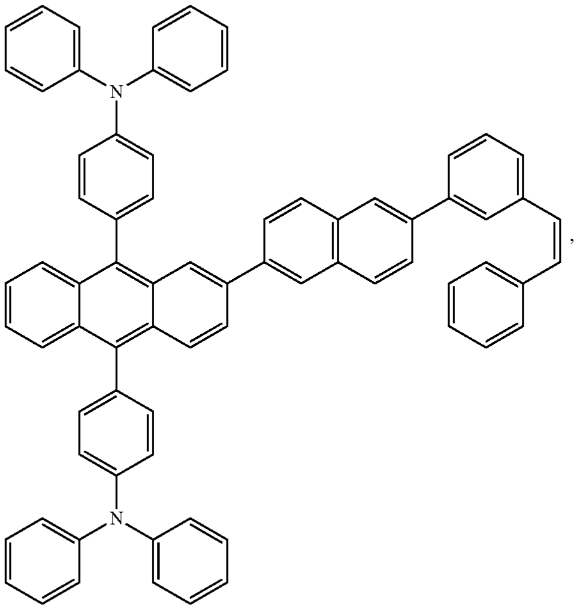
,
and
160
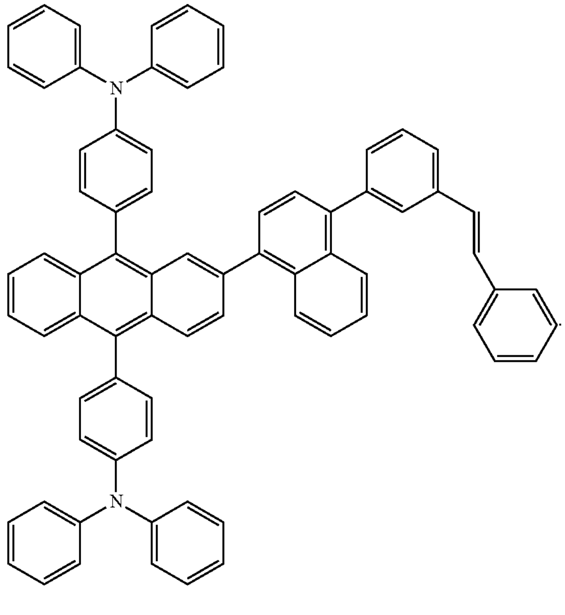
.
2. A compound selected from the group consisting of:
165
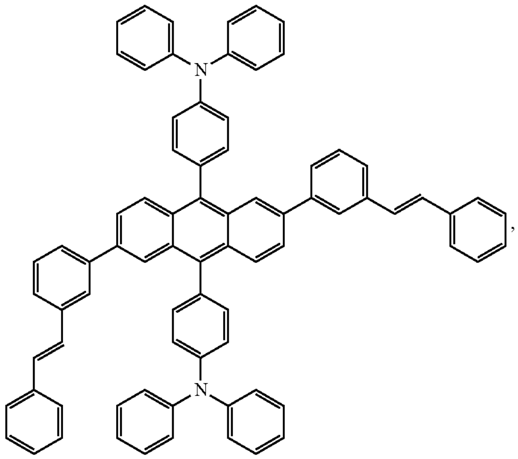
,
166
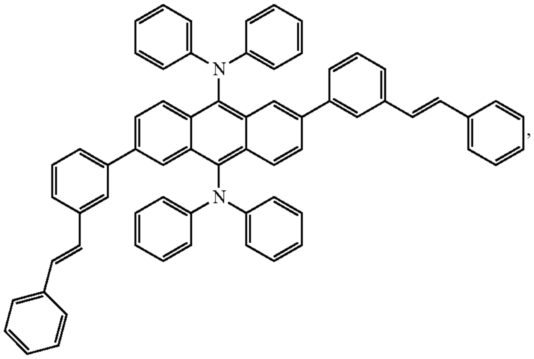
,
167
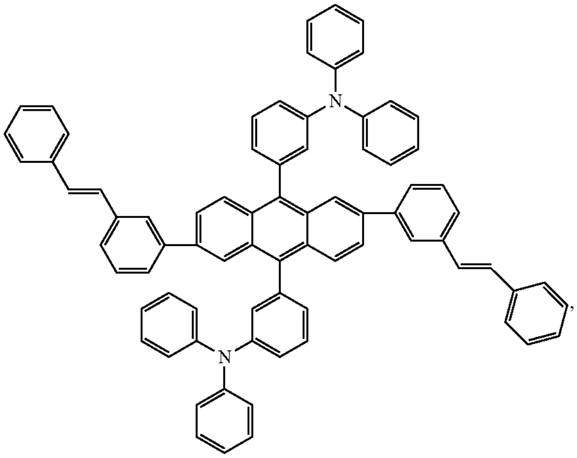
, -continued
168
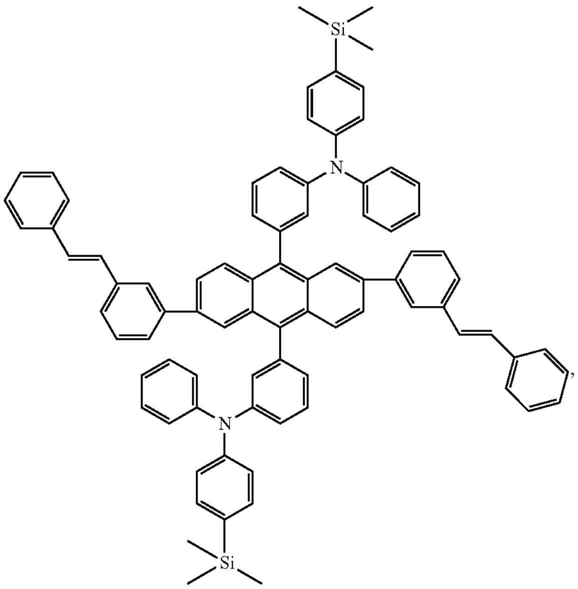
169
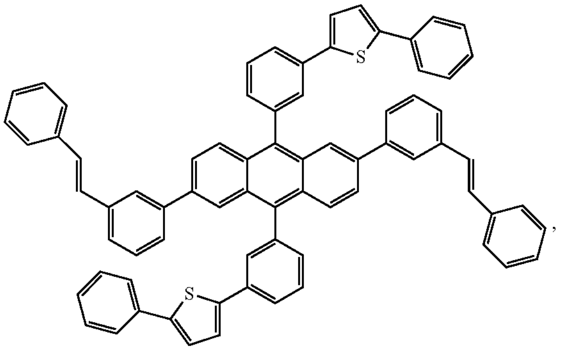
170
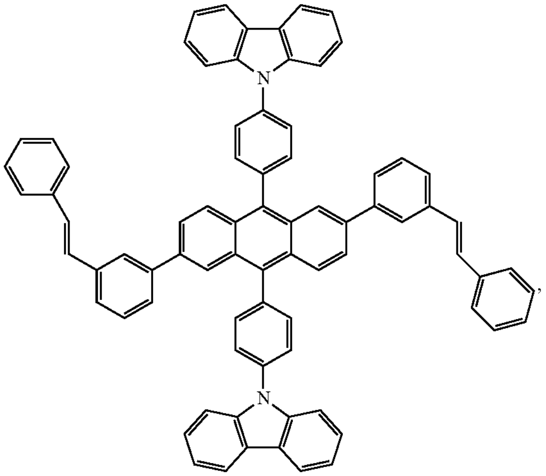
-continued
171
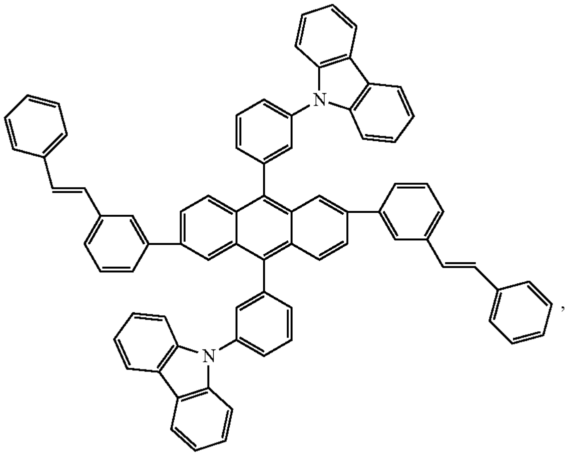
172
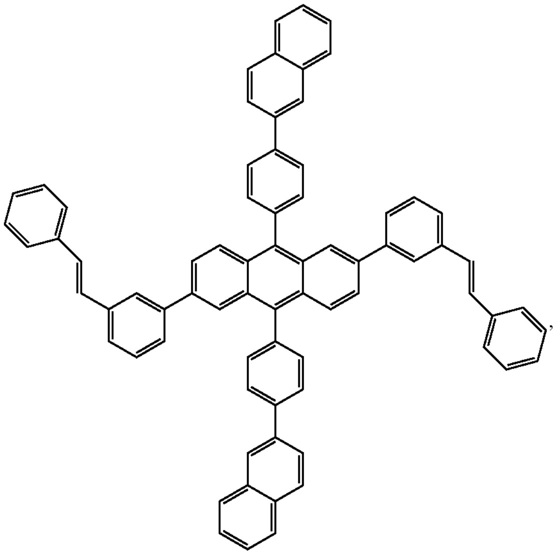

-continued
173
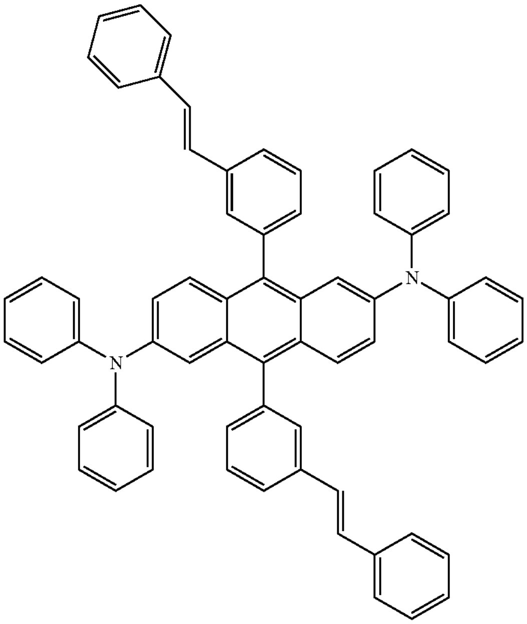
174
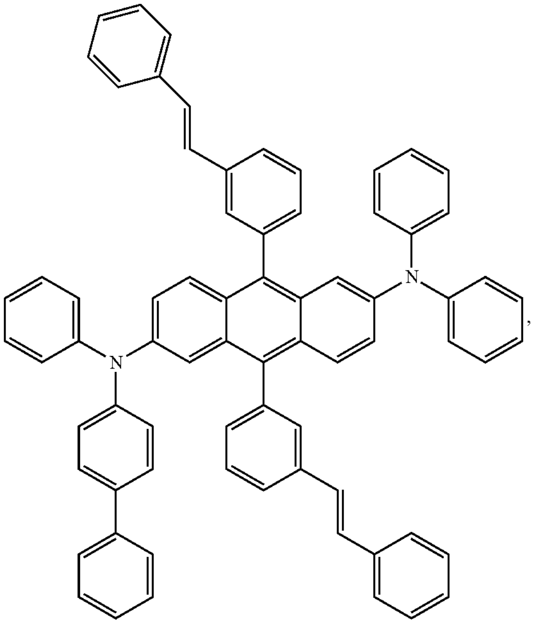
,
175
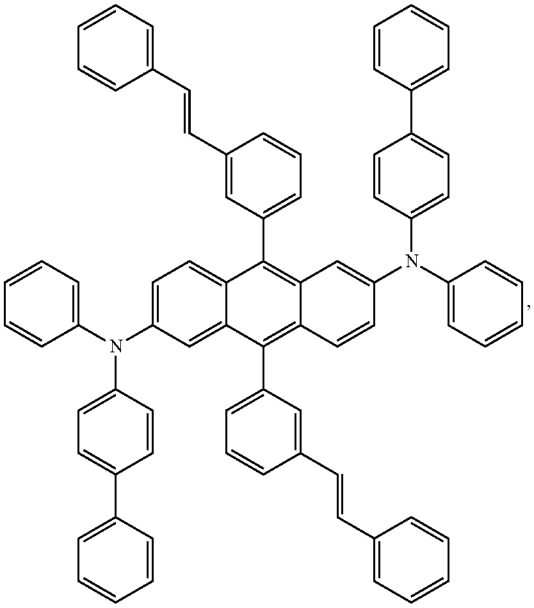
,
176
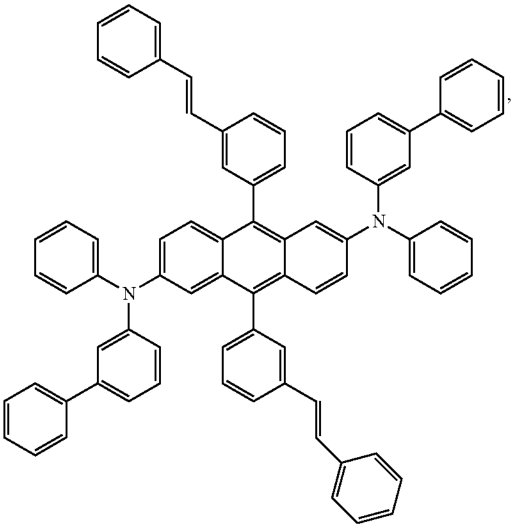
, -continued
177
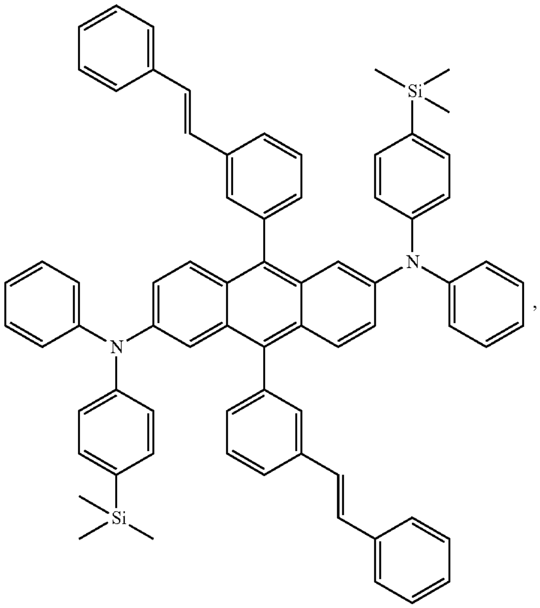
,
178
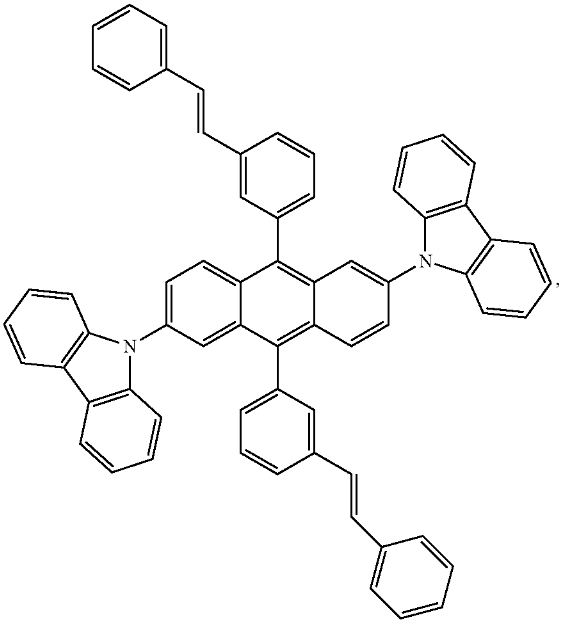
,
-continued
179
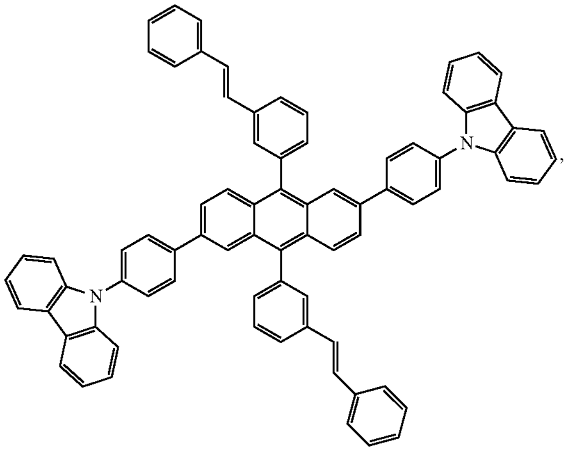
,
180
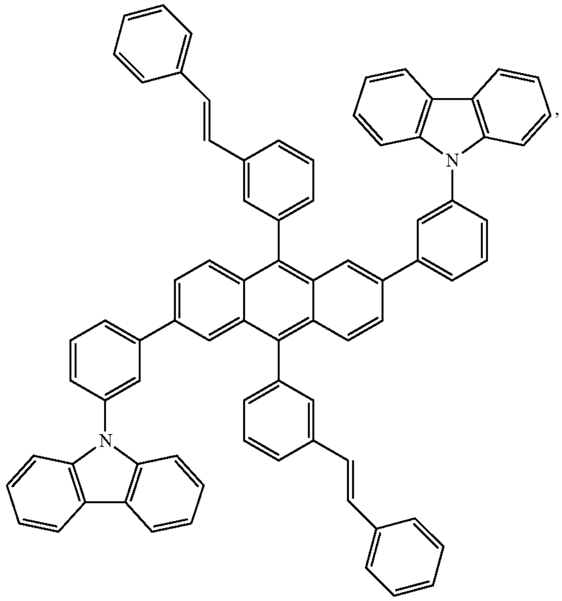
,
181
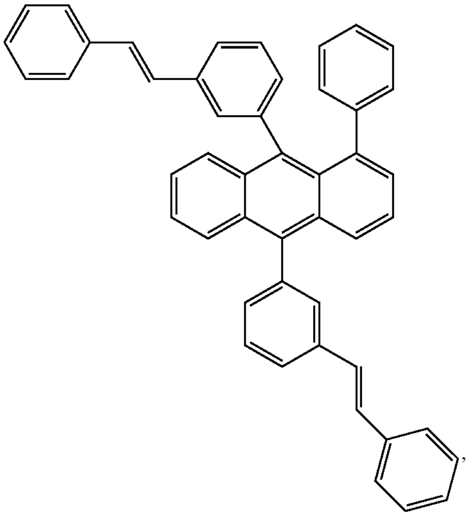
, 182
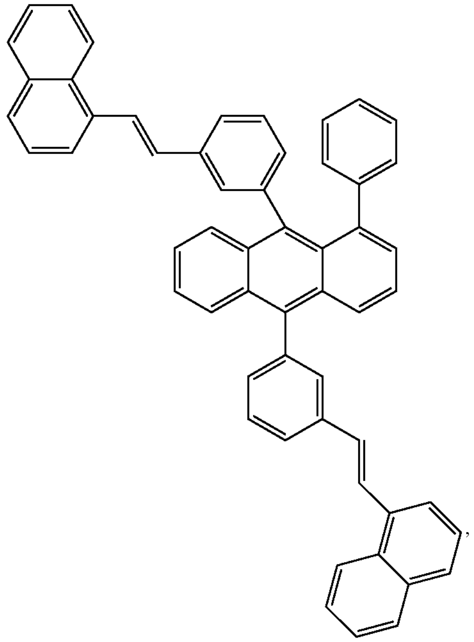
,
183
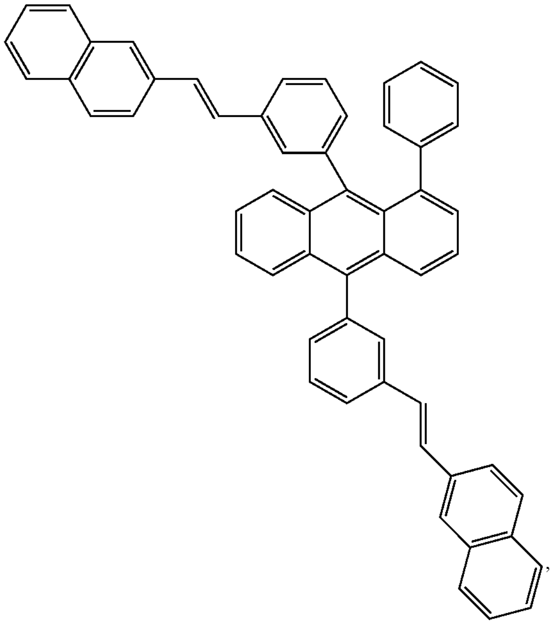
,
184
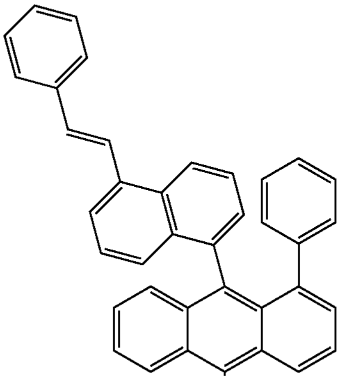
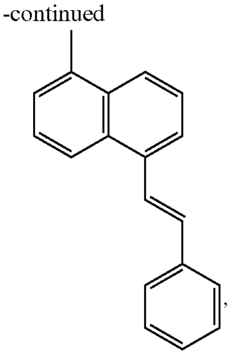
,
185
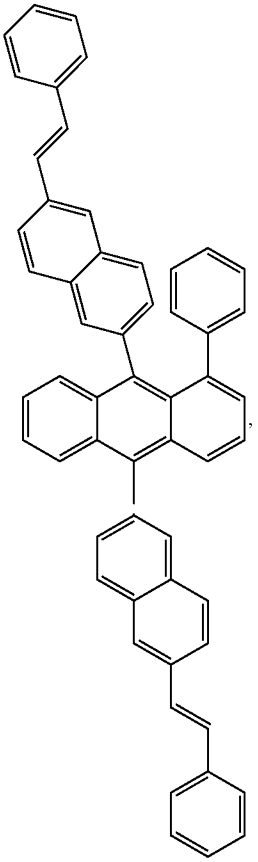
, -continued
186
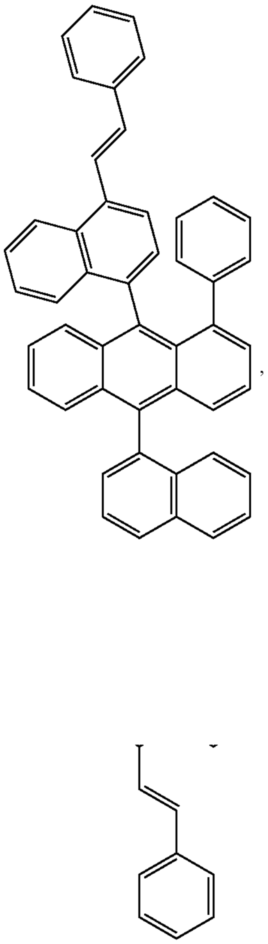
187
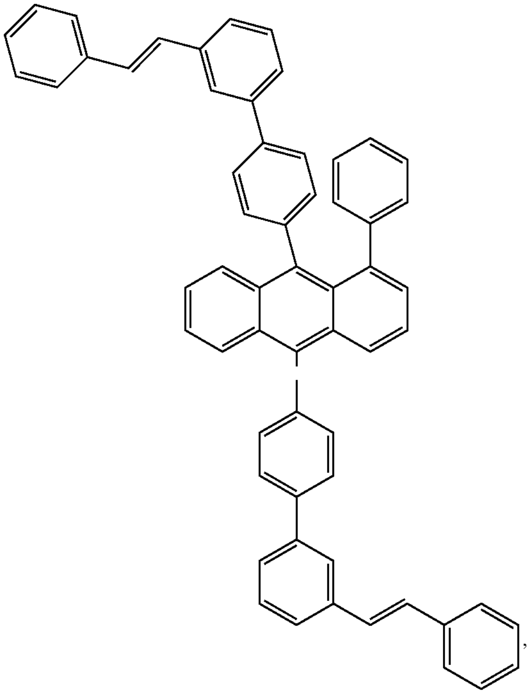
-continued
188
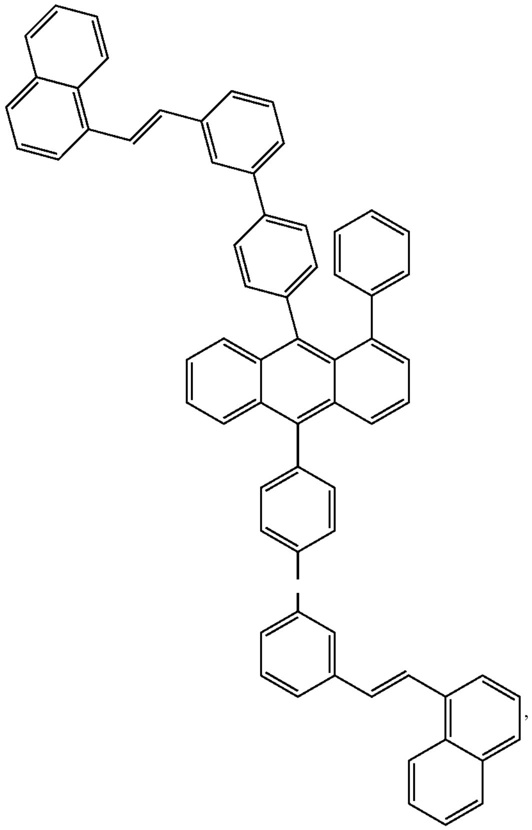
189
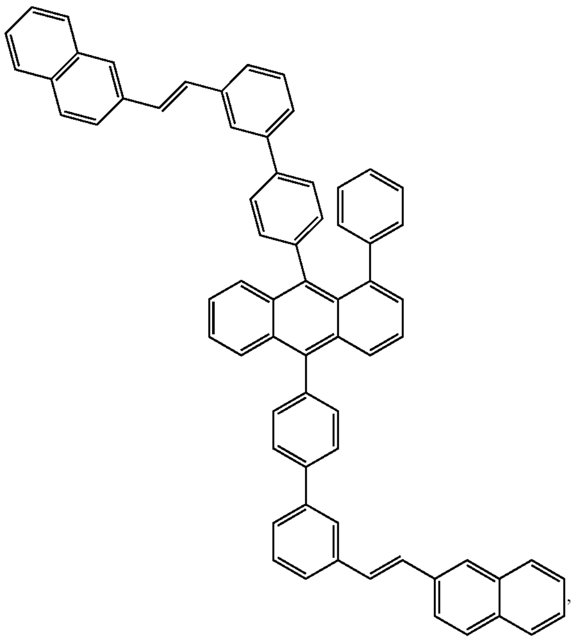

-continued
190
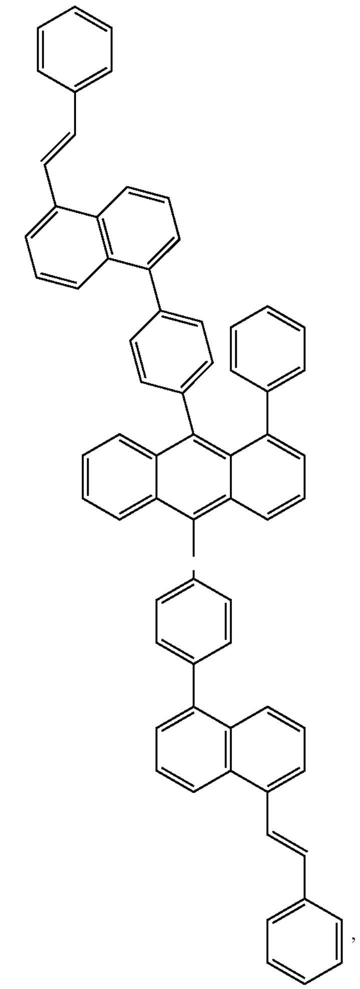
191
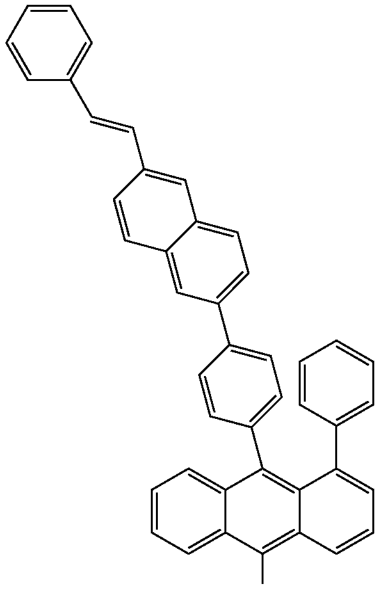
-continued
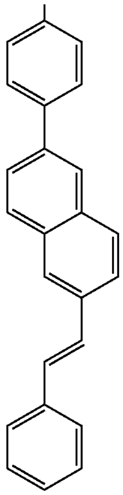
191
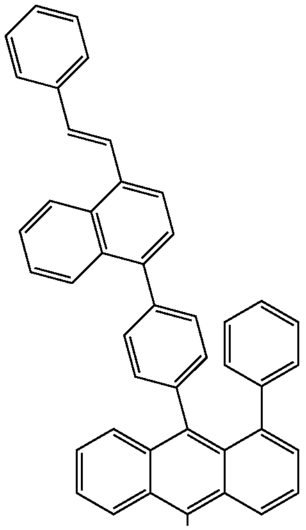
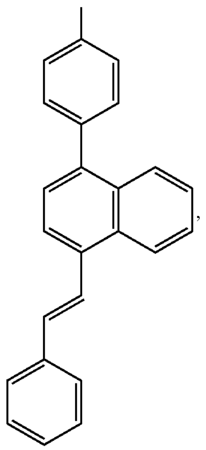

-continued
192
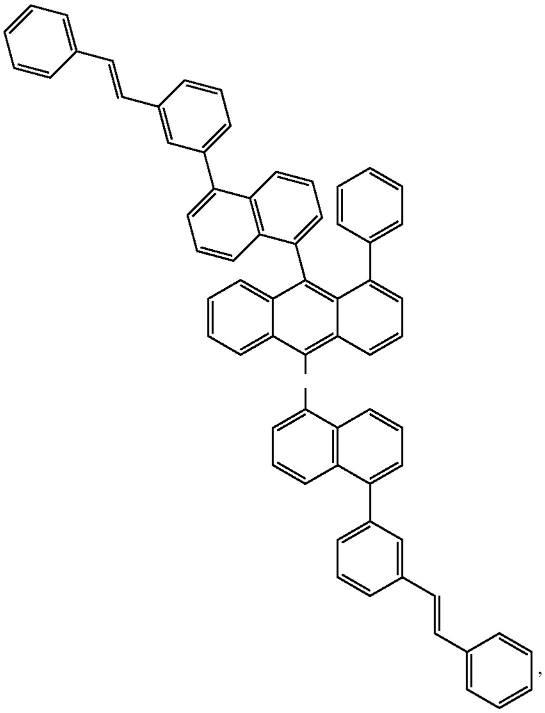
,
193
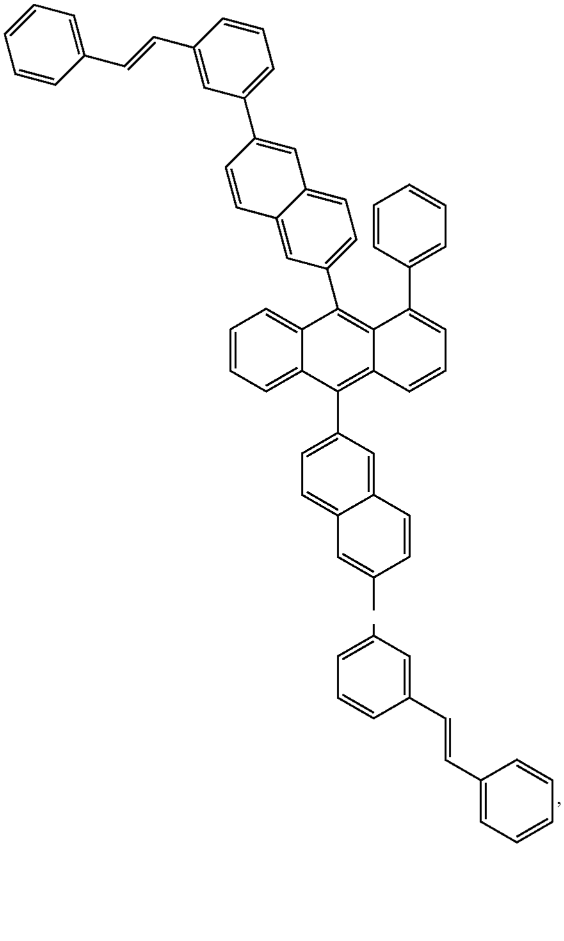
,
-continued
194
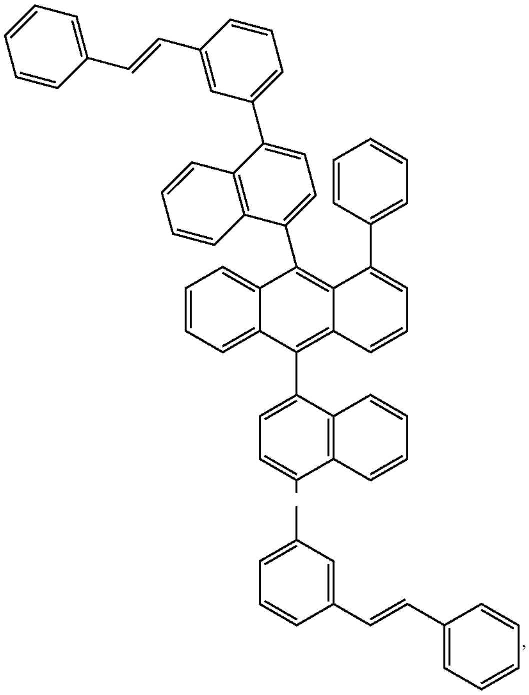
,
195
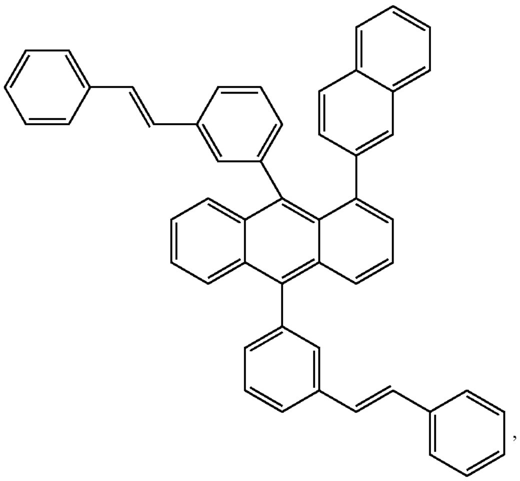
, 196
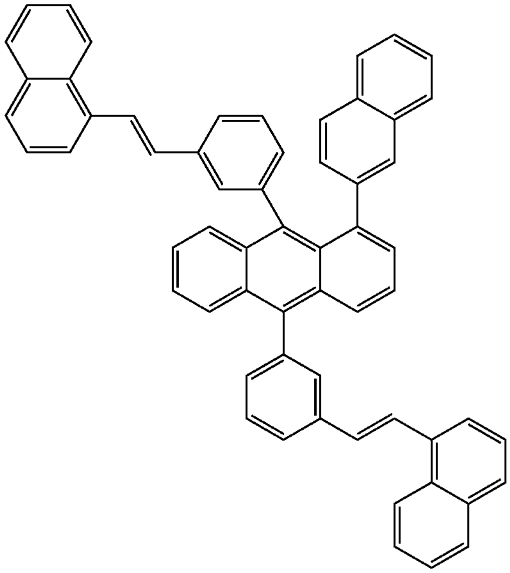
,
197
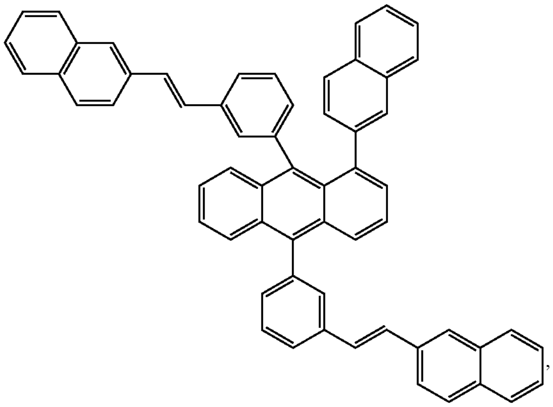
,
198
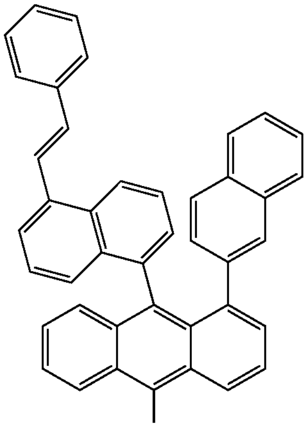
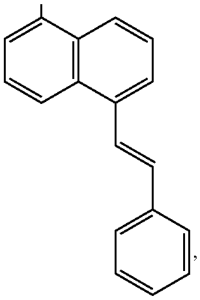
,
199
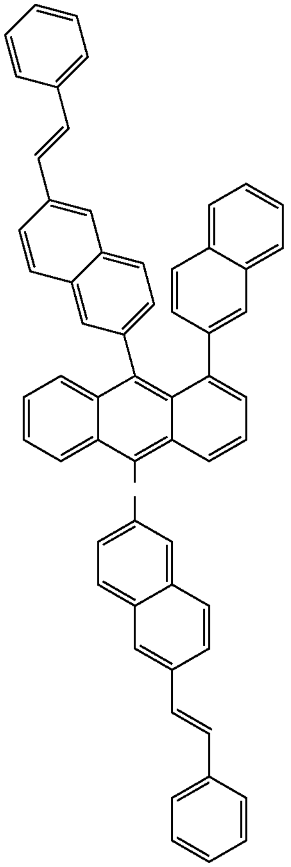
,
200
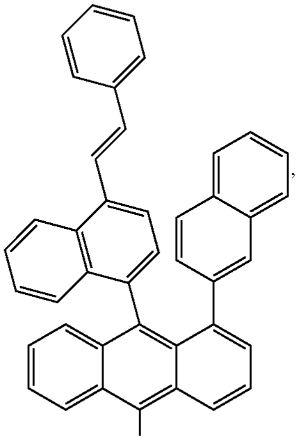
, -continued
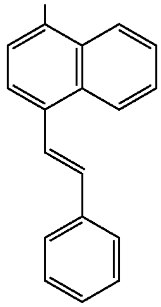
201
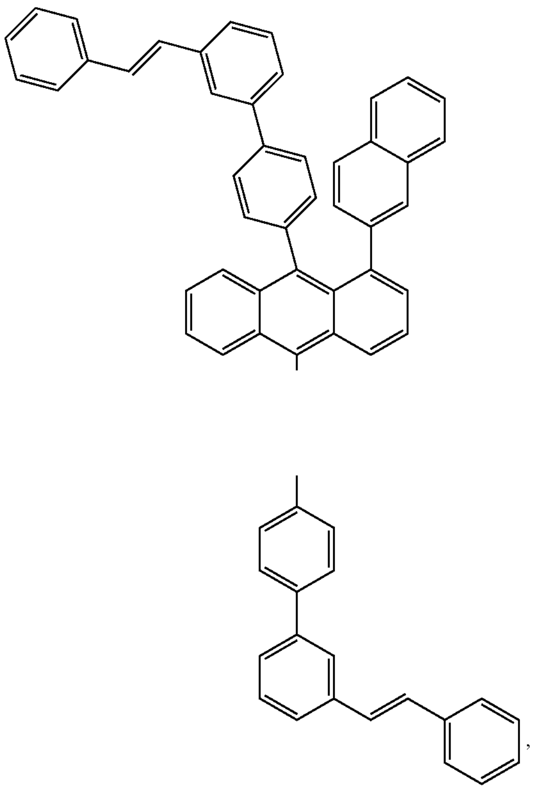
202
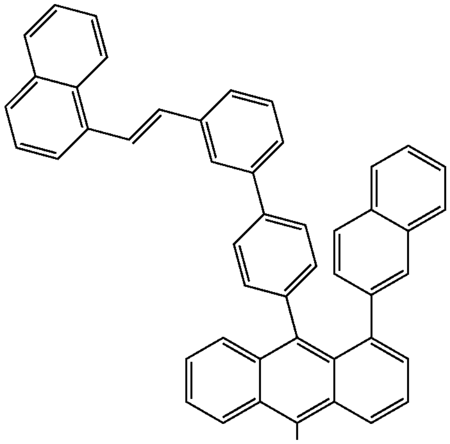
-continued
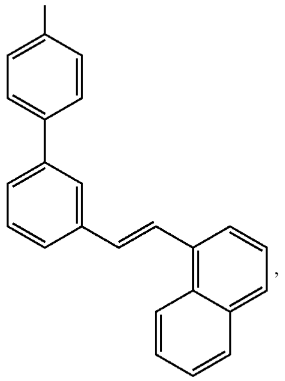
203
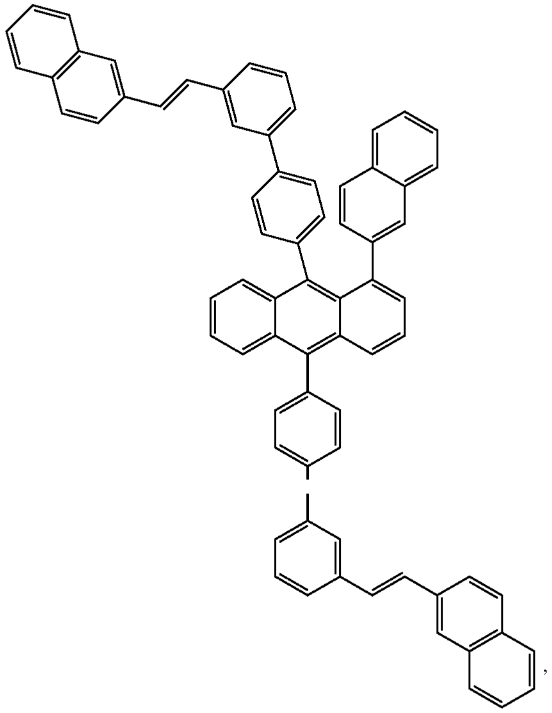
204
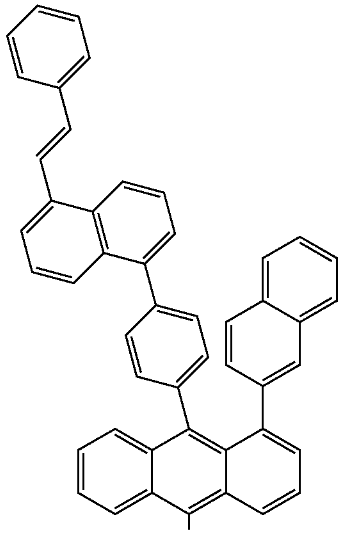

-continued
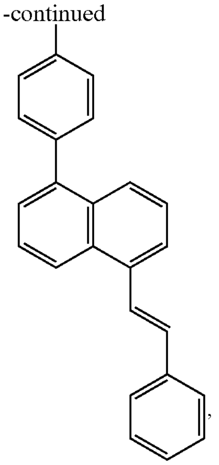
205
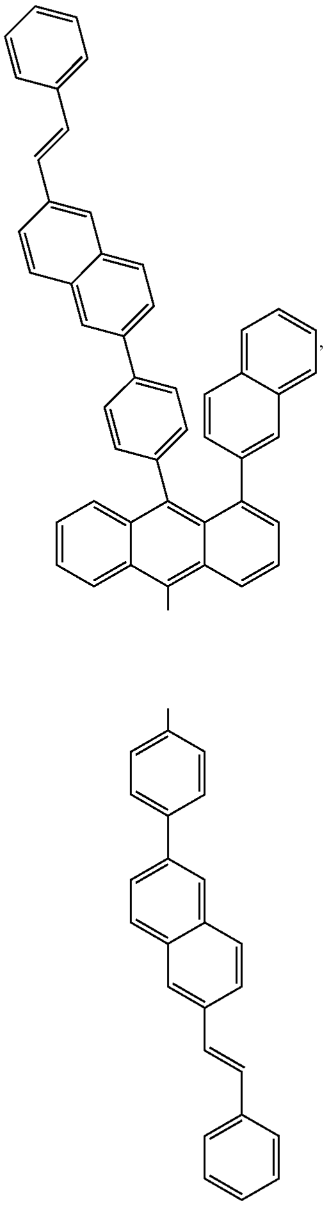
-continued
206
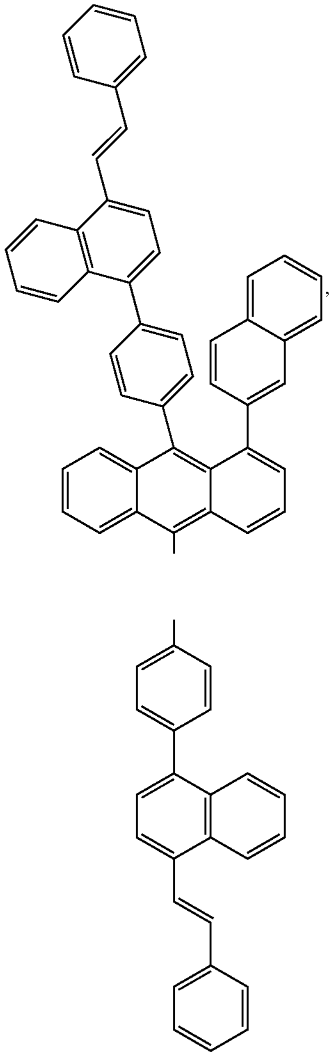
207
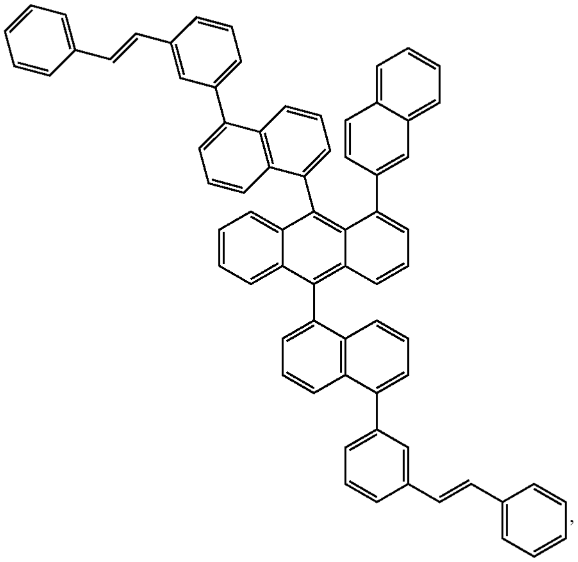

208
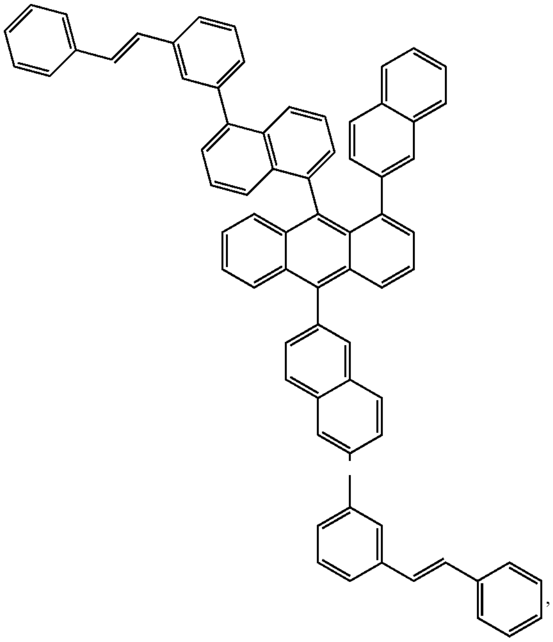
,
209
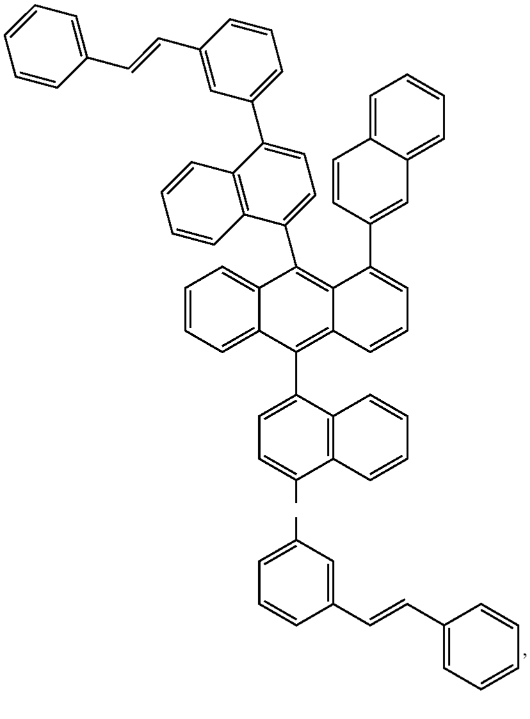
,
210
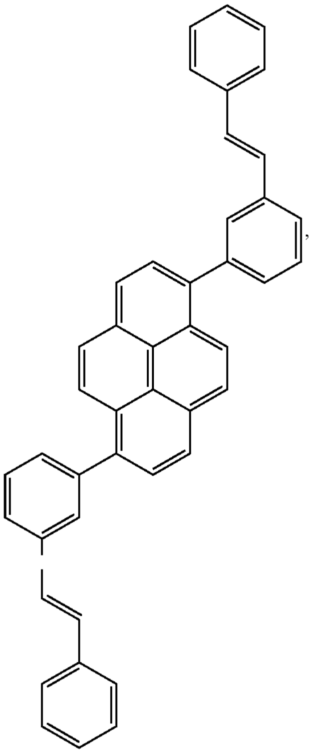
,
211
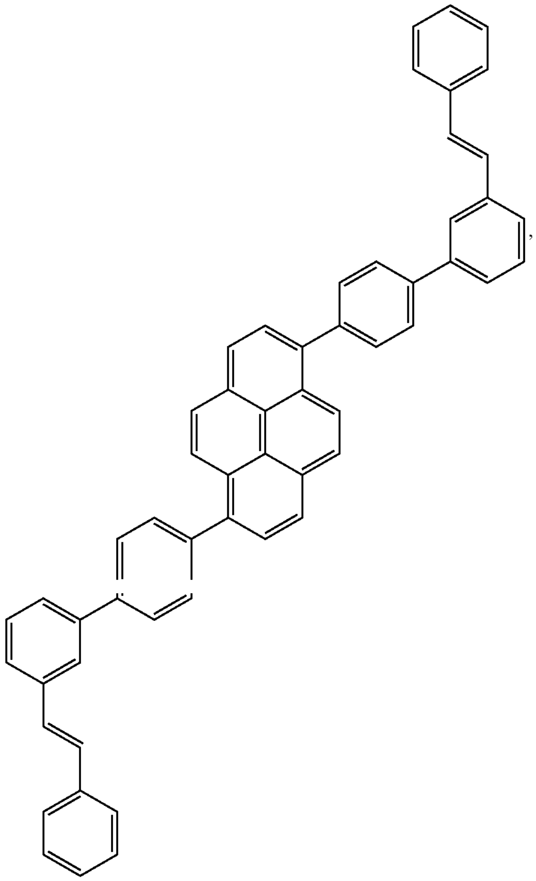
,

-continued

212

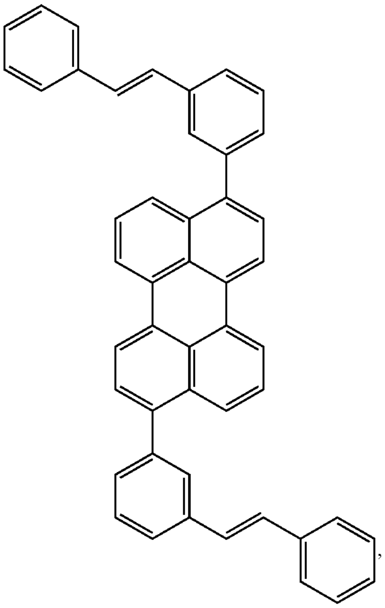

-continued

213

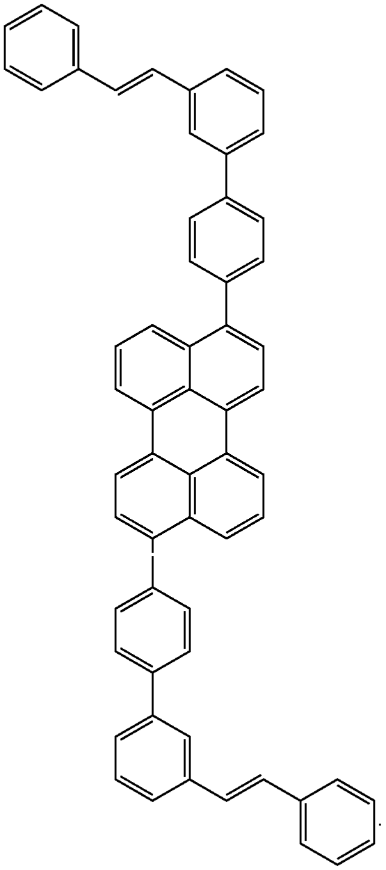

3. An organic light emitting diode comprising a first electrode, a second electrode, and at least one organic material layer disposed between the first electrode and the second electrode, wherein at least one layer of the organic material layer(s) comprises the compound according to any one of claims 1 and 2.

4. The organic light emitting diode according to 3, wherein the organic material layer comprises a light emitting layer, and the light emitting layer comprises the compound.

* * * * *